United States Patent
Bernate et al.

(10) Patent No.: US 10,435,713 B2
(45) Date of Patent: *Oct. 8, 2019

(54) FLOW THROUGH ELECTROPORATION INSTRUMENTATION

(71) Applicant: Inscripta, Inc., Boulder, CO (US)

(72) Inventors: Jorge Bernate, Boulder, CO (US); Don Masquelier, Boulder, CO (US)

(73) Assignee: Inscripta, Inc., Boulder, CO (US)

( * ) Notice: Subject to any disclaimer, the term of this patent is extended or adjusted under 35 U.S.C. 154(b) by 2 days.

This patent is subject to a terminal disclaimer.

(21) Appl. No.: 16/147,120

(22) Filed: Sep. 28, 2018

(65) Prior Publication Data

US 2019/0100720 A1    Apr. 4, 2019

Related U.S. Application Data

(60) Provisional application No. 62/566,374, filed on Sep. 30, 2017, provisional application No. 62/566,375, filed on Sep. 30, 2017, provisional application No. 62/566,688, filed on Oct. 2, 2017, provisional application No. 62/567,697, filed on Oct. 3, 2017, provisional application No. 62/620,370, filed on Jan. 22, 2018, provisional application No. 62/649,731, filed on Mar. 29, 2018, provisional application No. 62/671,385, filed on May 14, 2018, provisional application No. 62/648,130, filed on Mar. 26, 2018,
(Continued)

(51) Int. Cl.
| | | |
|---|---|---|
| *C12M 1/42* | (2006.01) | |
| *C12N 15/87* | (2006.01) | |
| *C12N 15/70* | (2006.01) | |
| *C12N 15/81* | (2006.01) | |
| *C12M 3/00* | (2006.01) | |
| *C12M 1/36* | (2006.01) | |

(52) U.S. Cl.
CPC ............. *C12N 15/87* (2013.01); *C12M 23/44* (2013.01); *C12M 35/02* (2013.01); *C12M 41/48* (2013.01); *C12N 15/70* (2013.01); *C12N 15/81* (2013.01)

(58) Field of Classification Search
CPC .............................. C12M 25/02; C12M 35/02
See application file for complete search history.

(56) References Cited

U.S. PATENT DOCUMENTS

| | | |
|---|---|---|
| 4,833,080 A | 5/1989 | Brent et al. |
| 4,959,317 A | 9/1990 | Sauer et al. |

(Continued)

FOREIGN PATENT DOCUMENTS

| | | |
|---|---|---|
| EP | 2240238 | 10/2010 |
| EP | 2395087 | 12/2011 |

(Continued)

OTHER PUBLICATIONS

Bao, et al., "Genome-scale engineering of *Saccharomyces cerevisiae* with single-nucleotide precision", Nature Biotechnology, doi:10.1038/nbt.4132, pp. 1-6 (May 7, 2018).
(Continued)

*Primary Examiner* — William H. Beisner
(74) *Attorney, Agent, or Firm* — Sarah Brashears; Dianna L. DeVore

(57) ABSTRACT

The present disclosure provides a flow-through electroporation device configured for use as a stand-alone module or as one module in an automated multi-module processing system.

9 Claims, 42 Drawing Sheets

Related U.S. Application Data provisional application No. 62/657,651, filed on Apr. 13, 2018, provisional application No. 62/657,654, filed on Apr. 13, 2018, provisional application No. 62/689,068, filed on Jun. 23, 2018.

(56) References Cited

U.S. PATENT DOCUMENTS

| | | |
|---|---|---|
| 5,464,764 A | 11/1995 | Capecchi et al. |
| 5,487,992 A | 1/1996 | Capecchi et al. |
| 5,627,059 A | 5/1997 | Capecchi et al. |
| 5,631,153 A | 5/1997 | Capecchi et al. |
| 5,654,182 A | 8/1997 | Wahl et al. |
| 5,677,177 A | 10/1997 | Wahl et al. |
| 5,885,836 A | 3/1999 | Wahl et al. |
| 5,888,732 A | 3/1999 | Hartley et al. |
| 6,074,605 A | 6/2000 | Meserol et al. |
| 6,143,527 A | 11/2000 | Pachuk et al. |
| 6,150,148 A | 11/2000 | Nanda et al. |
| 6,204,061 B1 | 3/2001 | Capecchi et al. |
| 6,277,608 B1 | 8/2001 | Hartley et al. |
| 6,482,619 B1 | 11/2002 | Rubinsky et al. |
| 6,509,156 B1 | 1/2003 | Stewart et al. |
| 6,654,636 B1 | 11/2003 | Dev et al. |
| 6,689,610 B1 | 2/2004 | Capecchi et al. |
| 6,746,441 B1 | 6/2004 | Hofmann et al. |
| 6,774,279 B2 | 8/2004 | Dymecki |
| 6,916,632 B2 | 7/2005 | Chesnut et al. |
| 6,956,146 B2 | 10/2005 | Wahl et al. |
| 7,029,916 B2 | 4/2006 | Dzekunov et al. |
| 7,112,715 B2 | 9/2006 | Chambon et al. |
| 7,141,425 B2 | 11/2006 | Dzekunov et al. |
| 7,422,889 B2 | 9/2008 | Sauer et al. |
| 8,110,122 B2 | 2/2012 | Alburty et al. |
| 8,110,360 B2 | 2/2012 | Serber et al. |
| 8,153,432 B2 | 4/2012 | Church et al. |
| 8,332,160 B1 | 12/2012 | Platt et al. |
| 8,569,041 B2 | 10/2013 | Church et al. |
| 8,584,535 B2 | 11/2013 | Page et al. |
| 8,584,536 B2 | 11/2013 | Page et al. |
| 8,667,839 B2 | 3/2014 | Kimura |
| 8,667,840 B2 | 3/2014 | Lee et al. |
| 8,677,839 B2 | 3/2014 | Page et al. |
| 8,677,840 B2 | 3/2014 | Page et al. |
| 8,697,359 B1 | 4/2014 | Zhang et al. |
| 8,726,744 B2 | 5/2014 | Alburty et al. |
| 8,758,623 B1 | 6/2014 | Alburty et al. |
| 8,921,332 B2 | 12/2014 | Choulika et al. |
| 8,932,850 B2 | 1/2015 | Chang et al. |
| 9,029,109 B2 | 5/2015 | Hur et al. |
| D731,634 S | 6/2015 | Page et al. |
| 9,063,136 B2 | 6/2015 | Talebpour et al. |
| 9,361,427 B2 | 6/2016 | Hillson |
| 9,534,989 B2 | 1/2017 | Page et al. |
| 9,546,350 B2 | 1/2017 | Dzekunov et al. |
| 9,593,359 B2 | 3/2017 | Page et al. |
| 9,738,918 B2 | 8/2017 | Alburty et al. |
| 9,790,490 B2 | 10/2017 | Zhang et al. |
| 9,896,696 B2 | 2/2018 | Begemann et al. |
| 9,982,279 B1 | 5/2018 | Gill et al. |
| 9,988,624 B2 | 6/2018 | Serber et al. |
| 10,017,760 B2 | 7/2018 | Gill et al. |
| 2003/0059945 A1 | 3/2003 | Dzekunov et al. |
| 2003/0073238 A1 | 4/2003 | Dzekunov et al. |
| 2003/0104588 A1* | 6/2003 | Orwar ............... A61K 9/127 435/173.6 |
| 2004/0115784 A1 | 6/2004 | Dzekunov et al. |
| 2004/0171156 A1 | 9/2004 | Hartley et al. |
| 2005/0064584 A1 | 3/2005 | Bargh |
| 2005/0118705 A1* | 6/2005 | Rabbitt ............. B01L 3/502761 435/287.1 |
| 2006/0224192 A1 | 10/2006 | Dimmer et al. |
| 2007/0105206 A1* | 5/2007 | Lu ..................... C12M 35/02 435/173.6 |
| 2007/0231873 A1 | 10/2007 | Ragsdale |
| 2007/0249036 A1 | 10/2007 | Ragsdale et al. |
| 2008/0138877 A1 | 6/2008 | Dzekunov et al. |
| 2010/0076057 A1 | 3/2010 | Sontheimer et al. |
| 2011/0009807 A1 | 1/2011 | Kjeken et al. |
| 2011/0061474 A1 | 3/2011 | Page et al. |
| 2011/0065171 A1 | 3/2011 | Dzekunov et al. |
| 2011/0082093 A1 | 4/2011 | Gregory et al. |
| 2011/0213288 A1 | 9/2011 | Choi et al. |
| 2011/0236962 A1 | 9/2011 | Loebbert et al. |
| 2012/0156786 A1 | 6/2012 | Bebee |
| 2012/0277120 A1 | 11/2012 | Serber et al. |
| 2013/0196441 A1 | 8/2013 | Rubinsky et al. |
| 2013/0253040 A1 | 9/2013 | Miller et al. |
| 2014/0121728 A1 | 5/2014 | Dhillon et al. |
| 2014/0350456 A1 | 11/2014 | Caccia |
| 2015/0297887 A1 | 10/2015 | Dhillon et al. |
| 2016/0018427 A1 | 1/2016 | Streibl et al. |
| 2016/0272961 A1 | 9/2016 | Lee |
| 2016/0281047 A1 | 9/2016 | Chen et al. |
| 2016/0298074 A1 | 10/2016 | Dai |
| 2016/0333302 A1 | 11/2016 | Im et al. |
| 2017/0029805 A1 | 2/2017 | Li et al. |
| 2017/0067007 A1 | 3/2017 | Miltenyi et al. |
| 2017/0218355 A1 | 8/2017 | Buie et al. |
| 2017/0283761 A1 | 10/2017 | Corso |
| 2017/0307606 A1 | 10/2017 | Hallock |
| 2017/0316353 A1 | 11/2017 | Frewen et al. |
| 2018/0023045 A1 | 1/2018 | Hallock et al. |
| 2018/0028567 A1 | 2/2018 | Li et al. |
| 2018/0051327 A1 | 2/2018 | Blainey et al. |
| 2018/0053547 A1 | 2/2018 | Juillerat et al. |
| 2018/0112235 A1 | 4/2018 | Li et al. |
| 2018/0169148 A1 | 6/2018 | Adair et al. |
| 2018/0179485 A1 | 6/2018 | Borenstein et al. |

FOREIGN PATENT DOCUMENTS

| | | |
|---|---|---|
| EP | 3030652 | 6/2016 |
| EP | 1766004 | 8/2016 |
| EP | 2459696 | 11/2017 |
| WO | WO2003/057819 | 7/2001 |
| WO | WO 2003087341 | 10/2003 |
| WO | WO 2009091578 | 7/2009 |
| WO | WO 2010079430 | 7/2010 |
| WO | WO 2011072246 | 6/2011 |
| WO | WO 2013/176772 | 11/2013 |
| WO | WO 2015021270 | 2/2015 |
| WO | WO 2016/003485 | 1/2016 |
| WO | WO 2016/145290 | 9/2016 |
| WO | WO 2017078631 | 5/2017 |
| WO | WO 2018015544 | 1/2018 |
| WO | WO 2018191715 | 10/2018 |

OTHER PUBLICATIONS

DiCarlo, et al., "Genome engineering in *Saccharomyces cervisiae* using CRISPR-Case systems", Nucleic Acids Research, 41(7):4336-43 (2013).

Eklund, et al., "Altered target site specificity variants of the I-Ppol His-Cys bis homing endonuclease" Nucleic Acids Research, 35(17):5839-50 (2007).

Garst, et al., "Genome-wide mapping of mutations at single-nucleotide resolution for protein, metabolic and genome engineering", Nature Biotechnology, 35(1):48-59 (2017).

Boles, et al., "Digital-to-biological converter for on-demand production of biologics", Nature Biotechnology, doi:10.1038/nbt.3859 (May 29, 2017).

Hsu, et al., "DNA targeting specificity of RNA-guided Cas9 nucleases", Nature Biotechnology, 31(9):827-32 (2013).

Jiang, et al., "RNA-guided editing of bacterial genomes using CRISPR-Cas systems", Nature Biotechnology, 31(3):233-41 (2013).

Jinek, et al., "A Programmable Dual-RNA-Guided DNA Endonuclease in Adaptive Bacterial Immunity", Science, 337:816-20 (2012).

Pines, et al., "Codon Compression Algorithms for Saturation Mutagenesis", ACS Synthetic Biology, 4:604-14 (2015).

Verwaal, et al., "CRISPR/Cpfl enables fast and simple genome editing of *Saccharamyces cerevisiae*", Yeast, 35:201-11 (2018).

(56) References Cited

OTHER PUBLICATIONS

Lian, et al., "Combinatorial metabolic engineering using an orthogonal tri-functional DRISPR system", Nature Communications, DOI:1038/s41467-017-01695-x/www.nature.com/naturecommunications, pp. 1-9 (2017).
Roy, et cl., "Multiplexed precision genome editing with trackable genomic barcodes in yeast", Nature Biotechnolgy, doi:10.1038/nbt.4137, pp. 1-16 (2018).
Bessa et al., "Improved gap repair cloning in yeast: treatment of the gapped vector with Taq DNA polymerase avoids vector self-ligation," Yeast, 29(10):419-23 (2012).
Boch, "TALEs of genome targeting," Nature Biotechnology vol. 29, pp. 135-136 (2011).
Campbell et al., "Targeting protein function: the expanding toolkit for conditional disruption," Biochem J., 473(17):2573-2589 (2016).
Casini et al., "Bricks and blueprints: methods and standards for DNA assembly," Nat Rev Mol Cell Biol., (9):568-76 (2015).
Chica et al., "Semi-rational approaches to engineering enzyme activity: combining the benefits of directed evolution and rational design," Current Opinion in Biotechnology, 16(4): 378-384 (2005).
Cramer et al., "Functional association between promoter structure and transcript alternative splicing," PNAS USA, 94(21):11456-60 (1997).
Dalphin et al., "Transterm: A Database of Translational Signals," Nucl. Acids Res., 24(1): 216-218 (1996).
Datsenko and Wanner, "One-step inactivation of chromosomal genes in *Escherichia coli* K-12 using PCR products", PNAS USA, 97(12):6640-5 (2000).
De Kok et al., "Rapid and reliable DNA assembly via ligase cycling reaction," ACS Synth Biol., 3(2):97-106 (2014).
Desmet et al., "Human Splicing Finder: an online bioinformatics tool to predict splicing signals," Nucleic Acids Res., 37(9):e67 (2009).
Divina et al., "Ab Initio prediction of mutation-induced cryptic splice-site activation and exon skipping," European Journal of Human Genetics, 17:759-765 (2009).
Dong, "Establishment of a highly efficient virus-inducible CRISPR/Cas9 system in insect cells," Antiviral Res., 130:50-7(2016).
Durai et al., "Zinc finger nucleases: custom-designed molecular scissors for genome engineering of plant and mammalian cells", Nucleic Acids Res., 33(18):5978-90 (2005).
Engler et al., "PLoS One, A One Pot, One Step, Precision Cloning Method with High Throughput Capability," 3(11):e3647 (2008).
Epinat et al., "A novel engineered meganuclease induces homologous recombination in eukaryotic cells, e.g., yeast and mammalian cells", Nucleic Acids Research, 31(11): 2952-2962.
Faber et al., "Genome-wide prediction of splice-modifying SNPs in human genes using a new analysis pipeline called AASsites," BMC Bioinformatics, 12(suppl 4):S2 (2011).
Farasat et al., "A Biophysical Model of CRISPR/Cas9 Activity for Rational Design of Genome Editing and Gene Regulation," PLoS Comput Biol., 29:12(1):e1004724 (2016).
International Search Report and Written Opinion for International Application No. PCT/US2018/040519, dated Sep. 26, 2018.
Greger et al., "Balancing transcriptional interference and initiation on the GAL7 promoter of *Saccharomyces cerevisiae*," PNAS, 97(15):8415-20 (2000).

Juan et al., "Histone deacetylases specifically down-regulate p53-dependent gene activation", Journal of Biological Chemistry 275.27 (2000): 20436-20443.
Kadonaga et al., "Regulation of RNA polymerase II transcription by sequence-specific DNA binding factors", Cell, 116(2):247-57 (2004).
Lee et al., "Targeted chromosomal deletions in human cells using zinc finger nucleases", Genome Res., 20 (1): 81-9 (2009).
Lefevre et al., "Alanine-stretch scanning mutagenesis: a simple and efficient method to probe protein structure and function," Nucleic Acids Research, vol. 25(2):447-448 (1997).
Liu et al., "A chemical-inducible CRISPR-Cas9 system for rapid control of genome editing", Nature Chemical Biology, 12:980-987(2016).
Miller et al., "A TALE nuclease architecture for efficient genome editing", Nature Biotechnology, 29 (2): 143-8 (2011).
Mittelman et al., "Zinc-finger directed double-strand breaks within CAG repeat tracts promote repeat instability in human cells", PNAS USA, 106 (24): 9607-12 (2009).
Mullick et al., "The cumate gene-switch: a system for regulated expression in mammalian cells", BMC Biotechnology, 6:43 (2006).
Nalla et al., "Automated splicing mutation analysis by information theory," Hum. Mutat., 25:334-342 (2005).
No et al., "Ecdysone-inducible gene expression in mammalian cells and transgenic mice," PNAS, 93(8):3346-3351 (1996).
Ohtsuka, "Recombinant DNA Technologies for Construction of Precisely Designed Transgene Constructs," Curr Pharm Biotechnol, 10(2):244-51 (2009).
Patron, "DNA assembly for plant biology: techniques and tools," Curr Opinion Plant Biol., 19:14-9 (2014).
Sands et al., "Overview of Post Cohen-Boyer Methods for Single Segment Cloning and for Multisegment DNA Assembly," Curr Protoc Mol Biol., 113:3.26.1-3.26.20 (2016)
Shivange, "Advances in generating functional diversity for directed protein evolution", Current Opinion in Chemical Biology, 13(1): 19-25 (2009).
Udo, "An Alternative Method to Facilitate cDNA Cloning for Expression Studies in Mammalian Cells by Introducing Positive Blue White Selection in Vaccinia Topoisomerase I-Mediated Recombination," PLoS One, 10(9):e0139349 (2015).
Urnov et al., "Genome editing with engineered zinc finger nucleases", Nature Reviews Genetics, 11:636-646 (2010).
West et al., "Molecular Dissection of Mammalian RNA Polymerase II Transcriptional Termination," Mol Cell. 29(5):600-10 (2008).
West et al., "Transcriptional Termination Enhances Protein Expression in Human Cells," Mol Cell.; 33(3-9); 354-364 (2009).
Adamo, et al., "Flow-trough comb electroporation device for delivery of macromolecules", Analytical Chemistry, 85(3):1637-41 (2015).
International Search Report and Written Opinion for International Application No. PCT/US2018/53608, dated Dec. 13, 2018, p. 1-9.
International Search Report and Written Opinion for International Application No. PCT/US2018/053670, dated Jan. 3, 2019, p. 1-11.
International Search Report and Written Opinion for International Application No. PCT/US2018/053671, dated Nov. 23, 2018, p. 1-12.
Nonfinal Office Action dated Apr. 30, 2019 for U.S. Appl. No. 16/147,353, pp. 1-17.

\* cited by examiner

FLOW THROUGH ELECTROPORATION INSTRUMENTATION

RELATED APPLICATIONS

This application claims priority to U.S. Patent Application Ser. No. 62/566,374, entitled "Electroporation Device," filed Sep. 30, 2017; U.S. Patent Application Ser. No. 62/566,375, entitled "Electroporation Device," filed Sep. 30, 2017; U.S. Patent Application Ser. No. 62/566,688, entitled "Introduction of Exogenous Materials into Cells," filed Oct. 2, 2017; U.S. Patent Application Ser. No. 62/567,697, entitled "Automated Nucleic Acid Assembly and Introduction of Nucleic Acids into Cells," filed Oct. 3, 2017; U.S. Patent Application Ser. No. 62/620,370, entitled "Automated Filtration and Manipulation of Viable Cells," filed Jan. 22, 2018; U.S. Patent Application Ser. No. 62/649,731, entitled "Automated Control of Cell Growth Rates for Induction and Transformation," filed Mar. 29, 2018; U.S. Patent Application Ser. No. 62/671,385, entitled "Automated Control of Cell Growth Rates for Induction and Transformation," filed May 14, 2018; U.S. Patent Application Ser. No. 62/648,130, entitled "Genomic Editing in Automated Systems," filed Mar. 26, 2018; U.S. Patent Application Ser. No. 62/657,651, entitled "Combination Reagent Cartridge and Electroporation Device," filed Apr. 13, 2018; U.S. Patent Application Ser. No. 62/657,654, entitled "Automated Cell Processing Systems Comprising Cartridges," filed Apr. 13, 2018; and U.S. Patent Application Ser. No. 62/689,068, entitled "Nucleic Acid Purification Protocol for Use in Automated Cell Processing Systems," filed Jun. 23, 2018. All above identified applications are hereby incorporated by reference in their entireties for all purposes.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

The cell membrane constitutes the primary barrier for the transport of molecules and ions between the interior and the exterior of a cell. Electroporation, also known as electropermeabilization, substantially increases cell membrane permeability in the presence of a pulsed electric field. Traditional electroporation systems have been widely used; however, traditional systems require high voltage input and suffer from adverse environmental conditions such as electric field distortion, local pH variation, metal ion dissolution and excess heat generation, all of which may contribute to low electroporation efficiency and/or cell viability. Further, traditional electroporation systems are not easily automated or incorporated into automated cell processing systems where electroporation is but one process performed. There is thus a need for automated multi-module cell processing systems and components thereof capable of transforming multiple cells in an efficient and automated fashion. The present invention addresses this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure provides an electroporation device configured both for use as a stand-alone electroporation device and for use in an automated multi-module cell processing environment. The device comprises a flow-through electroporation (FTEP) device for introducing exogenous materials into cells in a liquid medium, where the device comprises an inlet and an inlet channel for introducing cells and exogenous materials into the FTEP device, an outlet channel and an outlet for removing transformed cells from the FTEP device, a flow channel positioned between the inlet and outlet channels where the flow channel optionally decreases in width between the point where the inlet channel enters the flow channel and the outlet channel exits the flow channel, and two electrodes. In some embodiments, the two electrodes form a portion of the wall of the flow channel where the flow channel decreases in width. In other embodiments, the electrodes may be positioned such that a first electrode channel fluidically connects the first electrode to the flow channel between the inlet channel and the narrow portion of the flow channel, and a second electrode channel fluidically connects the second electrode to the flow channel between the narrow portion of the flow channel and the outlet channel.

Thus, in certain embodiments a flow-through electroporation (FTEP) device for introducing an exogenous material into cells in a fluid is provided, where the FTEP device comprises at least a first inlet and at least a first inlet channel for introducing a fluid comprising cells and exogenous material into the FTEP device; an outlet and an outlet channel for removing a fluid comprising transformed cells and exogenous material from the FTEP device; a flow channel intersecting and positioned between the first inlet channel and the outlet channel, wherein the flow channel decreases in width between the first inlet channel and the center of the flow channel and the outlet channel and the center of the flow channel; and two electrodes positioned in electrode channels between the intersection of the flow channel with the first inlet channel and the intersection of the flow channel with the outlet channel and on either end of where the flow channel decreases in width; wherein the electrodes are in fluid communication with fluid in the flow channel; and wherein the electrodes apply one or more electric pulses to the cells in the fluid as they pass through the flow channel, thereby introducing the exogenous material into the cells in the fluid.

In some aspects of this embodiment, the FTEP device further comprises a reservoir connected to the at least first inlet for introducing the cells in fluid into the FTEP device and a reservoir connected to the outlet for removing transformed cells from the FTEP device. In some aspects of this embodiment, the reservoirs coupled to the inlet(s) and outlet range in volume from 100 µL, to 10 ml, or from 0.5 ml to 7 ml, or from 1 ml to 5 ml.

In some aspects of this embodiment, the FTEP device comprises two inlets and two inlet channels and further comprises a reservoir connected to the second inlet for introducing the exogenous material into the FTEP device. In some configurations of this aspect, the second inlet and second inlet channel are located between the first inlet and first inlet channel and the electrodes; and in some configurations, the second inlet and second inlet channel are located between the electrodes and the outlet channel and outlet.

In some aspects of this embodiment, the two electrodes in the FTEP device are located from 0.5 mm to 10 mm apart, or from 1 mm to 8 mm apart, or from 3 mm and 7 mm apart, or from 4 mm to 6 mm apart. In some aspects of this embodiment, the FTEP device is between 3 cm to 15 cm in length, or between 4 cm to 12 cm in length, or from 4.5 cm to 10 cm in length, or from 5 cm to 8 cm in length. In some aspects of this embodiment, this embodiment of the FTEP device is between 0.5 cm to 5 cm in width, or from 0.75 cm to 3 cm in width, or from 1 cm to 2.5 cm in width, or from 1 cm to 1.5 cm in width. In some aspects of this embodiment, the narrowest part of the channel width in the FTEP device is from 10 µM to 5 mm.

In some aspects of this embodiment, the flow rate in the FTEP ranges from 0.1 ml to 5 ml per minute, or from 0.5 ml to 3 ml per minute, or from 1 ml to 2.5 ml per minute.

In some aspects of this embodiment the electrodes are configured to deliver 1-25 Kv/cm, or 10-20 Kv/cm.

In some aspects of this embodiment, the FTEP device further comprises one or more filters between the one or more inlet channels and the outlet channel. In some aspects, there are two filters, one between the inlet channel and the narrowed portion of the flow channel, and one between the narrowed portion of the flow channel and the outlet channel. In some aspects of this embodiment, the filters are graduated in pore size with the larger pores proximal to the inlet chamber or outlet chamber, and the small pores proximal to the narrowed portion of the flow channel. In some aspects, the small pores are the same size or larger than the size of the narrowed portion of the flow channel. In some aspects of this embodiment, the filter is formed separately from the body of the FTEP device and placed into the FTEP device as it is being assembled. Alternatively, in some aspects of this embodiment, the filter may be formed as part of and integral to the body of the FTEP device.

In some aspects of this embodiment, the FTEP devices can provide a cell transformation rate of $10^3$ to $10^{12}$ cells per minute, or $10^4$ to $10^{10}$ per minute, or $10^5$ to $10^9$ per minute, or $10^6$ to $10^8$ per minute. Typically, $10^8$ yeast cells may be transformed per minute, and $10^{10}$-$10^{11}$ bacterial cells may be transformed per minute.

In some aspects of this embodiment, the transformation of cells results in at least 90% viable cells, or 95% viable cells, and up to 99% viable cells.

In some aspects of this embodiment, the FTEP device is manufactured by injection molding from crystal styrene, cyclo-olefin polymer, or cyclo-olefin co-polymer, and in some aspects of this embodiment the electrodes are fabricated from stainless steel.

Yet another embodiment provides a flow-through electroporation (FTEP) device for introducing an exogenous material into cells in a fluid, the device comprising: at least one inlet and at least one inlet channel for introducing a fluid comprising cells and exogenous material to the FTEP device; an outlet and an outlet channel for removing transformed cells and exogenous material from the FTEP device; a flow channel positioned between a first inlet channel and the outlet channel where the flow channel intersects with the first inlet channel and the outlet channel and where a portion of the flow channel narrows between the inlet channel intersection with the flow channel and the outlet channel intersection with the flow channel; and an electrode positioned on either side of the flow channel and in direct contact with the fluid in the flow channel, and where the electrodes define the narrowed portion of the flow channel; and wherein the electrodes apply one or more electric pulses to the cells in the fluid as they pass through the flow channel, thereby introducing the exogenous material into the cells in the fluid.

In some aspects, the FTEP device further comprises a reservoir connected to the inlet for introducing the cells in fluid into the FTEP device and a reservoir connected to the outlet for removing transformed cells from the FTEP device, and in some aspects, the FTEP device comprises two inlets and two inlet channels and further comprises a reservoir connected to a second inlet for introducing the exogenous material into the FTEP device. In some aspects of this embodiment, the reservoirs coupled to the inlet(s) and outlet range in volume from 100 µL, to 10 ml, or from 0.5 ml to 7 ml, or from 1 ml to 5 ml.

In some aspects of this embodiment, the second inlet and second inlet channel are located between the first inlet and first inlet channel and the electrodes, and in some aspects the second inlet and second inlet channel are located between the electrodes and the outlet channel and outlet.

In some aspects of this embodiment, the two electrodes in the FTEP device are located from 10 µm to 1 mm apart, or from 25 µm to 3 mm apart, or from 50 µm and 2 mm apart, or from 75 µm to 1 mm apart. In some aspects of this embodiment, the FTEP device is between 3 cm to 15 cm in length, or between 4 cm to 12 cm in length, or between 4.5 cm to 10 cm in length, or between 0.5 cm to 8 cm in length. In some aspects of this embodiment, the FTEP device is between 0.5 cm to 5 cm in width, or from 0.75 cm to 3 cm in width, or from 1 cm to 2.5 cm in width, or from 1 cm to 1.5 cm in width. In some aspects of this embodiment, the narrowest part of the channel width of the FTEP device is from 10 µM to 5 mm, and in some aspects the narrowest part of the channel width is from 10 µM to 1 mm.

In some aspects of this embodiment, the flow rate in the FTEP ranges from 0.1 ml to 5 ml per minute, or from 0.5 ml to 3 ml per minute, or from 1 ml to 2.5 ml per minute.

In some aspects of this embodiment the electrodes are configured to deliver 1-25 Kv/cm, or 10-20 Kv/cm.

In some aspects of this embodiment, the FTEP device further comprises one or more filters between the one or more inlet channels and the outlet channel. In some aspects, there are two filters, one between the inlet channel and the narrowed portion of the flow channel, and one between the narrowed portion of the flow channel and the outlet channel. In some aspects of this embodiment, the filters are graduated in pore size with the larger pores proximal to the inlet chamber or outlet chamber, and the small pores proximal to the narrowed portion of the flow channel. In some aspects, the small pores are the same size or larger than the size of the narrowed portion of the flow channel. In some aspects of this embodiment, the filter is formed separately from the body of the FTEP device and placed into the FTEP device as it is being assembled. Alternatively, in some aspects of this embodiment, the filter may be formed as part of and integral to the body of the FTEP device.

In some aspects of this embodiment, the FTEP devices can provide a cell transformation rate of $10^3$ to $10^{12}$ cells per minute, or $10^4$ to $10^{10}$ per minute, or $10^5$ to $10^9$ per minute, or $10^6$ to $10^8$ per minute. Typically, $10^8$ yeast cells may be transformed per minute, and $10^{10}$-$10^{11}$ bacterial cells may be transformed per minute.

In some aspects of this embodiment, the transformation of cells results in at least 90% viable cells, or 95% viable cells, and up to 99% viable cells.

In some aspects of this embodiment, the FTEP device is manufactured by injection molding from crystal styrene, cyclo-olefin polymer, or cyclo-olefin co-polymer, and in some aspects the electrodes are fabricated from stainless steel.

In some aspects of either embodiment, the FTEP devices are fabricated as multiple FTEP devices in parallel on a single substrate where the FTEP devices are then separated for use.

In some aspects of either embodiment, the FTEP device is part of a reagent cartridge, and in some aspects the reagent cartridge comprises a script providing operating instructions for the FTEP device.

In some aspects of either embodiment, the FTEP device is comprised in a module that is part of an automated multi-module cell processing system, wherein the automated multi-module cell processing system comprises one or more of a receptacle for cells, one or more receptacles for nucleic acids or other material to be electroporated into the cells, a growth module, a filtration module, a recovery module, a nucleic acid assembly module, a purification module, an editing module, a singulation and growth module, a selection module, storage module, and a processor.

In addition, there is presented another embodiment of a flow-through electroporation (FTEP) device for introducing an exogenous material into cells in a fluid, the FTEP device comprising: at least a first inlet for receiving a fluid comprising cells or exogenous materials; a flow channel having a narrowed region area fluidically coupled to the first inlet for receiving the fluid, wherein the narrowed region confines a flow the fluid; at least two electrodes positioned in electrical communication with the fluid in the narrowed region of the flow channel, the electrodes being configured to apply an electric field to the cells or exogenous materials as they traverse the narrowed region of the flow channel, the electric field electroporating the cells thereby forming transformed cells; and at least one outlet coupled to the narrowed region of the flow channel and configured to receive the transformed cells. In some aspects, the at least two electrodes are configured to be in direct contact with the fluid. In some aspects of this embodiment the flow channel follows a non-linear path that imparts momentum to the cells such that at least a portion of the cells flow around an object positioned in the channel. In some aspects, the FTEP device further comprises at least one aperture proximate to the narrowed region of the flow channel for receiving a proximal end of a first electrode, whereby the first electrode is placed in direct contact with the fluid. Moreover, in some aspects, the aperture comprises a rounded edge. In some aspects of this embodiment, the narrowed region of the flow channel has a first cross sectional dimension and the at least two electrodes extend only partially across the narrowed region of the flow channel along that dimension.

As with the other embodiments, the FTEP device further comprises a reservoir connected to the inlet for introducing the cells in fluid into the FTEP device and a reservoir connected to the outlet for removing transformed cells from the FTEP device.

In some aspects of all embodiments, the FTEP device further comprises a seal to permit pressurization of FTEP device and provision of a pressure-driven flow. In some aspects, the FTEP device further comprises a pump to drive the fluid through the flow channel such that at least a plurality of the cells traverse the narrowed region of the flow channel more than once.

In some aspects of all embodiments, the FTEP device further comprises a voltage supply to apply time-varying voltage to the at least two electrodes.

As with earlier-described embodiments, one aspect of this embodiment of an FTEP further comprises a first reservoir connected to the first inlet for receiving and retaining the fluid and a second reservoir connected to the outlet for receiving the transformed cells, and in some aspects, the FTEP device further comprises a second inlet to receive exogenous material to be introduced into cells in the FTEP device, said inlet being in fluid communication with the narrowed area of the flow channel. Also in some aspects, the FTEP device further comprises a filter element configured to prevent transmission of any object substantially larger than the cells to the narrowed region of the flow channel, and in some aspects of this embodiment, the filter element is integrally formed with the structure forming the narrowed region of the flow channel, and in some aspects the filter element has progressively smaller apertures at locations closer to the narrowed region of the flow channel.

In other embodiments, a flow-through electroporation (FTEP) device for introducing an exogenous material into cells in a fluid is provided, the device comprising at least one inlet and at least one inlet channel for introducing a fluid comprising cells and exogenous material to the FTEP device; an outlet and an outlet channel for removing transformed cells and exogenous material from the FTEP device; a flow channel positioned between a first inlet channel and the outlet channel, wherein the flow channel intersects with the first inlet channel and the outlet channel and wherein a portion of the flow channel narrows between the inlet channel intersection and the outlet channel intersection; and an electrode positioned on either side of the narrowed portion of the flow channel and in direct contact with the fluid in the flow channel, the electrodes defining the narrowed portion of the flow channel; and wherein the electrodes apply one or more electric pulses to the cells in the fluid as they pass through the flow channel, thereby introducing the exogenous material into the cells in the fluid.

Yet other embodiments provide a flow-through electroporation (FTEP) device for introducing an exogenous material into cells in a fluid, the FTEP device comprising at least a first inlet and at least a first inlet channel for receiving a fluid comprising cells and/or exogenous material into the FTEP device; an outlet and an outlet channel for removing a fluid comprising transformed cells and exogenous material from the FTEP device; a flow channel intersecting and positioned between the at least first inlet channel and the outlet channel; two electrodes positioned in electrode channels between the intersection of the flow channel with the first inlet channel and the intersection of the flow channel with the outlet channel; wherein the electrodes are in fluid and electrical communication with fluid in the flow channel; and wherein the electrodes apply one or more electric pulses to the cells in the fluid as they pass through the flow channel, thereby introducing exogenous material into the cells in the fluid; and a filter positioned between the at least first inlet channel and the electrode channels.

In some aspects, the filter is integrally-formed as part of the FTEP device, and in some aspects, the filter and FTEP device are formed by injection-molding. In some aspects, the filter is a gradient filter, and in some aspects, the gradient comprises large pores proximal to the at least first inlet channel, and small pores proximal to the electrode channels. In some aspects of FTEP devices with filters, there is a second filter positioned between the electrodes and the outlet channel, and in some aspects, both filters are integrally formed as part of the FTEP device. In some aspects of this embodiment, both filters are gradient filters, and in some aspects, one gradient filter comprises large pores proximal to the at least first inlet channel and small pores proximal to the electrode channels, and wherein the other gradient filter comprises large pores proximal to the outlet channel and small pores proximal to the electrode channels.

In some aspects of this embodiment, the flow channel decreases in width between the first inlet channel and the center of the flow channel and the outlet channel and the center of the flow channel, and in some aspects of this embodiment, the two electrodes are positioned in electrode channels between the intersection of the flow channel with the first inlet channel and the intersection of the flow channel with the outlet channel and on either end of where the flow channel decreases in width.

In aspects of the embodiments of the FTEP device that comprises a filter, the filter elements include "pegs" or "protrusions", and the "pegs" or "protrusions" may be round, oval, elliptical, or polygonal in shape.

Yet another embodiment provides a method of electroporating cells comprising: providing a flow-through electroporation (FTEP) device, wherein the flow-through electroporation device comprises an inlet and at least an inlet channel for receiving a fluid comprising electrocompetent cells and exogenous material into the FTEP device; an outlet and an outlet channel for removing a fluid comprising transformed cells and exogenous material from the FTEP device; a flow channel intersecting and positioned between the inlet channel and the outlet channel; and two electrodes positioned between the intersection of the flow channel with the inlet channel and the intersection of the flow channel with the outlet channel; wherein the electrodes are in fluid and electrical communication with fluid in the flow channel; flowing the cells comprising the electrocompetent cells and exogenous material into the inlet and the inlet channel; flowing the cells through the flow channel and past the two electrodes; providing electrical pulses to the cells in the fluid as the cells flow through the flow channel past the electrodes producing electroporated cells; and removing the electroporated cells from the outlet channel and outlet.

In some aspects the flow channel in the FTEP device decreases in width between the inlet channel and a mid-region of the flow channel and the outlet channel and the mid-region of the flow channel, and in some aspects of this embodiment, the flow channel decreases in width to between 10 μm and 5 mm, or to between 50 μm and 2 mm, or to a dimension no smaller than at least 2× diameters of the cells being electroporated.

In some aspect, the electrodes are configured to deliver a voltage of 1-25 Kv/cm, or a voltage of 5-20 Kv/cm, or a voltage of 10-20 Kv/cm. In some aspects the flow rate of the FTEP device is between 0.1 mL to 5 mL per minute, or between 0.5 mL to 3 mL per minute.

In some aspects of this embodiment, the two electrodes are each disposed within an electrode channel, and one electrode is located between the inlet channel and the mid-region of the flow channel and one electrode is located between the outlet channel and the mid-region of the flow channel. In some configurations of this aspect, in the electrodes are between 0.5 mm to 10 mm apart, or between 3 mm to 7 mm apart.

In some aspects of this embodiment, the electrodes are positioned on either side of the flow channel, are in direct contact with the fluid in the flow channel and define the decrease in width of the flow channel. In some configurations of this aspect, the electrodes are between 10 μm to 5 mm apart, or between 25 μm to 2 mm apart.

In some aspects of this embodiment, the FTEP device further comprises at least one filter disposed within the flow channel, and in some configurations of this aspect, the filter is integrally-formed as part of the FTEP device. In some configurations, the filter is a gradient filter, and in some configurations, the gradient comprises large pores proximal to the inlet channel, and small pores proximal to the electrodes. Further, in some configurations the FTEP device further comprises a second filter positioned between the electrodes and the outlet channel, and in some configurations both filters are integrally formed as part of the FTEP device. Also, in some configurations where there are two filters, one gradient filter comprises large pores proximal to the inlet channel and small pores proximal to the electrodes, and wherein the second gradient filter comprises large pores proximal to the outlet channel and small pores proximal to the electrodes.

Additionally provided is a method of electroporating cells comprising: providing a flow-through electroporation (FTEP) device, wherein the flow-through electroporation device comprises an inlet and an inlet channel for receiving a fluid comprising electrocompetent cells and exogenous material into the FTEP device; an outlet and an outlet channel for removing a fluid comprising transformed cells and exogenous material from the FTEP device; a flow channel intersecting and positioned between the inlet channel and the outlet channel; and two electrodes positioned between the intersection of the flow channel with the channel and the intersection of the flow channel with the outlet channel; wherein the electrodes are in fluid and electrical communication with fluid in the flow channel; flowing the cells comprising the electrocompetent cells and exogenous material into the inlet and the inlet channel; flowing the cells through the flow channel and past the two electrodes; providing electrical pulses to the cells in the fluid as the cells flow through the flow channel past the electrodes producing electroporated cells; flowing the electroporated cells to the outlet channel and outlet; reversing the flow of the cells to flow the cells from the outlet, through the outlet channel, through the flow channel and past the two electrodes; providing electrical pulses to the cells in the fluid as the cells flow through the flow channel; and flowing the electroporated cells into the inlet channel and inlet.

Some aspects of this embodiment further comprise, after the flowing the electroporated cells into the inlet step, again reversing the flow of the cells to flow the cells from the inlet, through the inlet channel, through the flow channel and past the two electrodes, providing electrical pulses to the cells in the fluid as the cells flow through the flow channel past the two electrodes; and removing the electroporated cells from the outlet channel and outlet.

In some aspects of this embodiment, the flow channel in the FTEP device decreases in width between the inlet channel and a mid-region of the flow channel and the outlet channel and the mid-region of the flow channel, and in some aspects the flow channel decreases in width to a dimension no smaller than at least 2× diameters of the cells being electroporated.

These aspects and other features and advantages of the invention are described below in more detail.

BRIEF DESCRIPTION OF THE DRAWINGS

The foregoing and other features and advantages of the present invention will be more fully understood from the following detailed description of illustrative embodiments taken in conjunction with the accompanying drawings in which.

It should be understood that the drawings are not necessarily to scale, and that like reference numbers refer to like features.

DETAILED DESCRIPTION

Figure 1A:
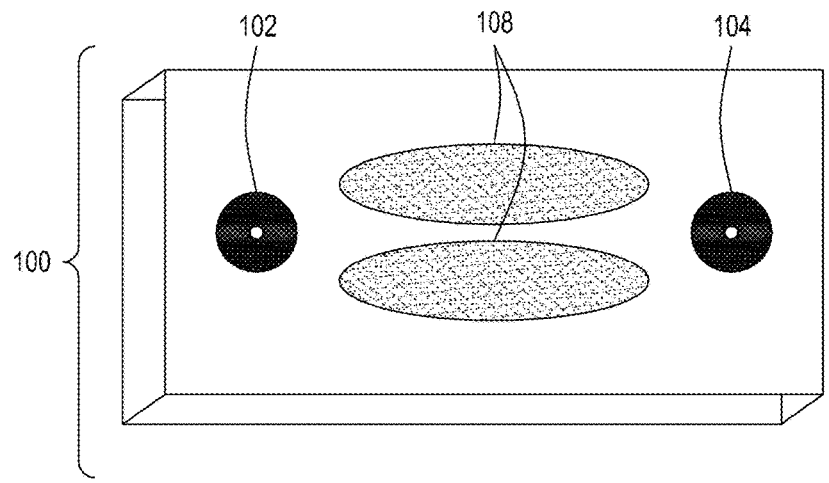
FIG. 1A is an illustration of a top view of one aspect of the FTEP devices of the disclosure.

All of the functionalities described in connection with one embodiment are intended to be applicable to the additional embodiments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions molecular biology (including recombinant techniques), cell biology, biochemistry, and genetic engineering technology, which are within the skill of those who practice in the art. Such conventional techniques and descriptions can be found in standard laboratory manuals such as Green and Sambrook, *Molecular Cloning: A Laboratory Manual.* 4th, ed., Cold Spring Harbor Laboratory Press, Cold Spring Harbor, N.Y., (2014); *Current Protocols in Molecular Biology*, Ausubel, et al. eds., (2017); Neumann, et al., *Electroporation and Electrofusion in Cell Biology*, Plenum Press, New York, 1989; and Chang, et al., *Guide to Electroporation and Electrofusion*, Academic Press, California (1992), all of which are herein incorporated in their entirety by reference for all purposes.

Note that as used herein and in the appended claims, the singular forms "a," "an," and "the" include plural referents unless the context clearly dictates otherwise. Thus, for example, reference to "an oligo" refers to one or more oligos that serve the same function, to "the methods" includes reference to equivalent steps and methods known to those skilled in the art, and so forth. That is, unless expressly specified otherwise, as used herein the words "a," "an," "the" carry the meaning of "one or more." Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Additionally, the terms "approximately," "proximate," "minor," and similar terms generally refer to ranges that include the identified value within a margin of 20%, 10% or preferably 5% in certain embodiments, and any values therebetween.

Unless defined otherwise, all technical and scientific terms used herein have the same meaning as commonly understood by one of ordinary skill in the art to which this invention belongs. All publications mentioned herein are incorporated by reference for all purposes, including the purpose of describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in smaller ranges, and are also encompassed within the invention, subject to any specifically excluded limit in the stated range. Where the stated range includes one or both of the limits, ranges excluding either or both of those included limits are also included in the invention.

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention. The terms used herein are intended to have the plain and ordinary meaning as understood by those of ordinary skill in the art.

The Invention in General

Electroporation is a widely-used method for permeabilization of cell membranes that works by temporarily generating pores in the cell membranes with electrical stimulation. The applications of electroporation include the delivery of DNA, RNA, siRNA, peptides, proteins, antibodies, drugs or other substances to a variety of cells such as mammalian cells (including human cells), plant cells, archaea, yeasts, other eukaryotic cells, bacteria, and other cell types. Further, mixtures of cell types can also be electroporated in a single run; e.g., mixtures of *E. coli* strains, mixtures of bacterial strains, mixtures of yeast strains, mixtures of mammalian cells. Electrical stimulation may also be used for cell fusion in the production of hybridomas or other fused cells. During a typical electroporation procedure, cells are suspended in a buffer or medium that is favorable for cell survival. For bacterial cell electroporation, low conductance mediums, such as water, glycerol solutions and the like, are often used to reduce the heat production by transient high current. The cells and material to be electroporated into the cells (collectively "the cell sample") is then placed in a cuvette embedded with two flat electrodes for an electrical discharge. For example, Bio-Rad (Hercules, Calif.) makes the GENE PULSER XCELL™ line of products to electroporate cells in cuvettes. Traditionally, electroporation requires high field strength.

Generally speaking, microfluidic electroporation—using cell suspension volumes of less than approximately 20 ml and as low as 1 µl—allows more precise control over a transfection or transformation process and permits flexible integration with other cell processing tools compared to bench-scale electroporation devices. Microfluidic electroporation thus provides unique advantages for, e.g., single cell transformation, processing and analysis; multi-unit FTEP device configurations; and integrated, automated multi-module cell processing and analysis.

The present disclosure provides electroporation devices, electroporation systems and methods that achieve high efficiency cell electroporation with low toxicity where the electroporation devices and systems can be integrated with other automated cell processing tools. Further, the electroporation device of the disclosure allows for multiplexing where two to many electroporation units are constructed and used in parallel, which allows for particularly easy integration with robotic liquid handling instrumentation. Such automated instrumentation includes, but is not limited to, off-the-shelf automated liquid handling systems from Tecan (Mannedorf, Switzerland), Hamilton (Reno, Nev.), Beckman Coulter (Fort Collins, Colo.), etc.

During the electroporation process, it is important to use voltage sufficient for achieving electroporation of material into the cells, but not too much voltage as too much power will decrease cell viability. For example, to electroporate a suspension of a human cell line, 200 volts is needed for a 0.2 ml sample in a 4 mm-gap cuvette with exponential discharge from a capacitor of about 1000 µF. However, if the same 0.2 ml cell suspension is placed in a longer container with 2 cm electrode distance (5 times of cuvette gap distance), the voltage required would be 1000 volts, but a capacitor of only 40 µF (1/25 of 1000 µF) is needed because the electric energy from a capacitor follows the equation of:

$$E=0.5U^2C$$

where E is electric energy, U is voltage and C is capacitance. Therefore a high voltage pulse generator is easy to manufacture because it needs a much smaller capacitor to store a similar amount of energy. Similarly, it would not be difficult to generate other wave forms of higher voltages.

The electroporation devices of the disclosure can allow for a high rate of cell transformation in a relatively short amount of time. The rate of cell transformation is dependent on the cell type and the number of cells being transformed. For example, for *E. coli*, the electroporation devices can provide a cell transformation rate of $10^3$ to $10^{12}$ cells per minute, $10^4$ to $10^{10}$ per minute, $10^5$ to $10^9$ per minute, or $10^6$ to $10^8$ per minute. Typically, $10^8$ yeast cells may be transformed per minute, and $10^{10}$-$10^{11}$ bacterial cells may be transformed per minute. The electroporation devices also allow transformation of batches of cells ranging from 1 cell to $10^{11}$ cells in a single transformation procedure using parallel devices.

Exemplary FTEP Embodiments

Figure 1B:
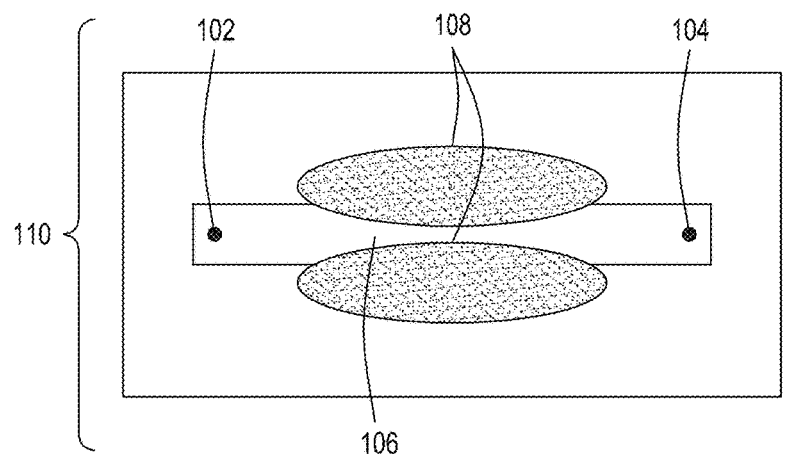
FIG. 1B is an illustration of the top view of a cross section of the aspect of the device shown in FIG. 1A.
Figure 1C:
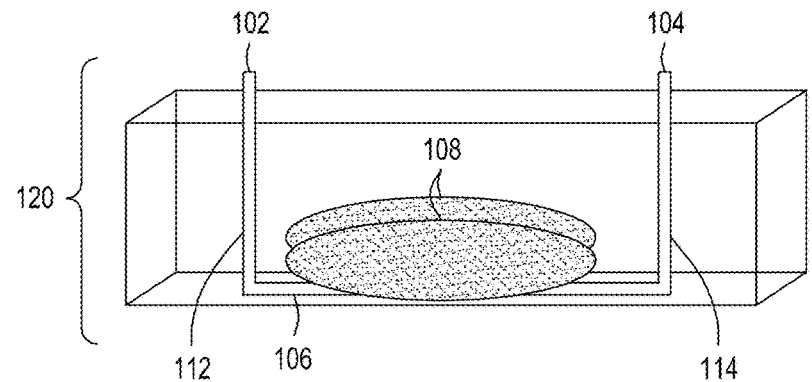
FIG. 1C is an illustration of a side view of a cross section of the aspect of the device shown in FIGS. 1A and 1B.

A first aspect of the invention described herein is illustrated in FIGS. 1A-1C. FIG. 1A shows a planar top view of an FTEP device 100 having an inlet 102 for introducing a fluid containing cells and exogenous material to be delivered to the cells into the FTEP device 100 and an outlet 104 for removing the transformed cells following electroporation. Oval electrodes 108 are positioned so as to define a center portion of the flow channel (not shown) where the channel narrows based on the curvature of the electrodes. FIG. 1B shows a cutaway view 110 from the top of the device 100, with the inlet 102, outlet 104, and electrodes 108 positioned with respect to a flow channel 106. Note that the electrodes 108 define a narrowing of flow channel 106. FIG. 1C shows a side cutaway view 120 of the device 100 with the inlet 102 and inlet channel 112, and outlet 104 and outlet channel 114. The electrodes 108 are oval in shape and positioned so that they define a narrowed portion of the flow channel 106.

In the FTEP devices of the disclosure, the toxicity level of the transformation results in greater than 30% viable cells after electroporation, preferably greater than 35%, 40%, 45%, 50%, 55%, 60%, 70%, 75%, 80%, 85%, 90%, 95%, or even 99% viable cells following transformation, depending on the cell type and the nucleic acids being introduced into the cells.

The housing of the FTEP device can be made from many materials depending on whether the FTEP device is to be reused, autoclaved, or is disposable, including stainless steel, silicon, glass, resin, polyvinyl chloride, polyethylene, polyamide, polystyrene, polyethylene, polypropylene, acrylonitrile butadiene, polycarbonate, polyetheretheketone (PEEK), polysulfone and polyurethane, co-polymers of these and other polymers. Similarly, the walls of the channels in the device can be made of any suitable material including silicone, resin, glass, glass fiber, polyvinyl chloride, polyethylene, polyamide, polyethylene, polypropylene, acrylonitrile butadiene, polycarbonate, polyetheretheketone (PEEK), polysulfone and polyurethane, co-polymers of these and other polymers. Preferred materials include crystal styrene, cyclo-olefin polymer (COP) and cyclic olephin co-polymers (COC), which allow the device to be formed entirely by injection molding in one piece with the exception of the electrodes and, e.g., a bottom sealing film if present (see, e.g., FIG. 16B(v)).

The FTEP devices described herein (or portions of the FTEP devices) can be created or fabricated via various techniques, e.g., as entire devices or by creation of structural layers that are fused or otherwise coupled. For example, for metal FTEP devices, fabrication may include precision mechanical machining or laser machining; for silicon FTEP devices, fabrication may include dry or wet etching; for glass FTEP devices, fabrication may include dry or wet etching, powderblasting, sandblasting, or photostructuring; and for plastic FTEP devices, fabrication may include thermoforming, injection molding, hot embossing, or laser machining. The components of the FTEP devices may be manufactured separately and then assembled, or certain components of the FTEP devices (or even the entire FTEP device except for the electrodes) may be manufactured (e.g., using 3D printing) or molded (e.g., using injection molding) as a single entity, with other components added after molding. For example, housing and channels may be manufactured or molded as a single entity, with the electrodes later added to form the FTEP unit (see, e.g., FIG. 16F). In some embodiments, a film or a flat substrate may be used to seal the bottom of the device, as shown in FIG. 16B(v). The film, in some embodiments, is made from the same material as the FTEP device, in this case, e.g., crystal styrene, cyclo-olefin polymer (COP) or cyclic olephin co-polymers (COC). The FTEP device may also be formed in two or more parallel layers, e.g., a layer with the horizontal channel and filter, a layer with the vertical channels, and a layer with the inlet and outlet ports, which are manufactured and/or molded individually and assembled following manufacture. (See, e.g., FIG. 13A.)

In specific aspects, the FTEP device can be manufactured using a circuit board as a base, with the electrodes, filter and/or the flow channel formed in the desired configuration on the circuit board, and the remaining housing of the device containing, e.g., the one or more inlet and outlet channels and/or the flow channel formed as a separate layer that is then sealed onto the circuit board. The sealing of the top of the housing onto the circuit board provides the desired configuration of the different elements of the FTEP devices of the disclosure. Also, two to many FTEP devices (up to 48 or more) may be manufactured in parallel on a single substrate, then separated from one another thereafter or used in parallel. In certain embodiments, the FTEP devices are reusable and, in some embodiments, the FTEP devices are disposable. In additional embodiments, the FTEP devices may be autoclavable.

The electrodes 108 can be formed from any suitable metal, such as copper, stainless steel, titanium, aluminum, brass, silver, rhodium, gold or platinum, or graphite. One preferred electrode material is alloy 303 (UNS330300) austenitic stainless steel. An applied electric field can destroy electrodes made from of metals like aluminum. If a multiple-use (e.g., non-disposable) flow-through FTEP device is desired—as opposed to a disposable, one-use flow-through FTEP device—the electrode plates can be coated with metals resistant to electrochemical corrosion. Conductive coatings like noble metals, e.g., gold, can be used to protect the electrode plates.

Additionally, the FTEP devices may comprise push-pull pneumatic means to allow multi-pass electroporation procedures; that is, cells to electroporated may be "pulled" from the inlet toward the outlet for one pass of electroporation, then be "pushed" from the outlet end of the flow-through FTEP device toward the inlet end to pass between the electrodes again for another pass of electroporation. This process may be repeated one to many times.

Depending on the type of cells to be electroporated (e.g., bacterial, yeast, mammalian) and the configuration of the electrodes, the distance between the electrodes in the flow channel can vary widely. For example, in the embodiments shown in FIGS. 1A-1C, 2A-2C, 3A-3C, 4A-4E, 5A-5C, 6, and 7A-7E where the electrodes form a portion of the wall of the flow channel where the flow channel decreases in width, the distance between the electrodes in the flow channel may be between 10 μm and 5 mm, or between 25 μm and 3 mm, or between 50 μm and 2 mm, or between 75 μm and 1 mm. In other embodiments such as those depicted in FIGS. 8A-8E, 9A-9C, 10A-10E, 11A-11E, 12A-12C, 13A-13B, 14, and 16A-16D where the electrodes are positioned on either end of the channel narrowing, the distance between the electrodes in the flow channel may be between 1 mm and 10 mm, or between 2 mm and 8 mm, or between 3 mm and 7 mm, or between 4 mm and 6 mm. The overall size of the FTEP device may be from 3 cm to 15 cm in length, or 4 cm to 12 cm in length, or 4.5 cm to 10 cm in length. The overall width of the FTEP device may be from 0.5 cm to 5 cm, or from 0.75 cm to 3 cm, or from 1 cm to 2.5 cm, or from 1 cm to 1.5 cm.

The region of the flow channel that is narrowed is typically wide enough so that at least two cells can fit in the narrowed portion side-by-side. For example, a typical bacterial cell is 1 μm in diameter; thus, the narrowed portion of the flow channel of the FTEP device used to transform such bacterial cells will be at least 2 μm wide. In another example, if a mammalian cell is approximately 50 μm in diameter, the narrowed portion of the flow channel of the FTEP device used to transform such mammalian cells will be at least 100 μm wide. That is, the narrowed portion of the FTEP device will not physically contort or "squeeze" the cells being transformed.

In embodiments of the FTEP device where reservoirs are used to introduce cells and exogenous material into the FTEP device, the reservoirs range in volume from 100 μL, to 10 mL, or from 500 μL, to 75 mL, or from 1 mL to 5 mL. The flow rate in the FTEP ranges from 0.1 mL to 5 mL per minute, or from 0.5 mL to 3 mL per minute, or from 1.0 mL to 2.5 mL per minute. The pressure in the FTEP device ranges from 1-30 psi, or from 2-10 psi, or from 3-5 psi.

To avoid different field intensities between the electrodes, the electrodes should be arranged in parallel. Furthermore, the surface of the electrodes should be as smooth as possible without pin holes or peaks. Electrodes having a roughness Rz of 1 to 10 μm are preferred. In another embodiment of the invention, the flow-through electroporation device comprises at least one additional electrode which applies a ground potential to the FTEP device.

The electrodes are configured to deliver 1-25 Kv/cm, or 5-20 Kv/cm, or 10-20 Kv/cm. The further apart the electrodes are, the more voltage needs to be supplied; in addition, the voltage delivered of course depends on the types of cells being porated, the medium in which the cells are suspended, the size of the electroporation channel, and the length and diameter of the electrodes. There are many different pulse forms that may be employed with the FTEP device, including exponential decay waves, square or rectangular waves, arbitrary wave forms, or a selected combination of wave forms. One type of common pulse form is the exponential decay wave, typically made by discharging a loaded capacitor to the cell sample. The exponential decay wave can be made less steep by linking an inductor to the cell sample so that the initial peak current can be attenuated. When multiple waveforms in a specified sequence are used, they can be in the same direction (direct current) or different directions (alternating current). Using alternating current can be beneficial in that two topical surfaces of a cell instead of just one can be used for molecular transport, and alternating current can prevent electrolysis. The pulse generator can be controlled by a digital or analog panel. In some embodiments, square wave forms are preferred, and in other embodiments, an initial wave spike before the square wave is preferred.

The FTEP device may be configured to electroporate cell sample volumes between 1 μl to 5 ml, 10 μl to 2 ml, 25 μl to 1 ml, or 50 μl to 750 μl. The medium or buffer used to suspend the cells and material (reagent) to be electroporated into the cells for the electroporation process may be any suitable medium or buffer for the type of cells being transformed or transfected, such as SOC, MEM, DMEM, IMDM, RPMI, Hanks', PBS and Ringer's solution, where the media may be provided in a reagent cartridge as part of a kit. Further, because the cells must be made electrocompetent prior to transformation or transfection, the buffer also may comprise glycerol or sorbitol, and may also comprise a surfactant. For electroporation of most eukaryotic cells the medium or buffer usually contains salts to maintain a proper osmotic pressure. The salts in the medium or buffer also render the medium conductive. For electroporation of very small prokaryotic cells such as bacteria, sometimes water or 10% glycerol is used as a low conductance medium to allow a very high electric field strength. In that case, the charged molecules to be delivered still render water-based medium more conductive than the lipid-based cell membranes and the medium may still be roughly considered as conductive particularly in comparison to cell membranes.

The compound to be electroporated into the cells can be any compound known in the art to be useful for electroporation, such as nucleic acids, oligonucleotides, polynucleotides, DNA, RNA, peptides, proteins and small molecules like hormones, cytokines, chemokines, drugs, or drug precursors.

Figure 2A:
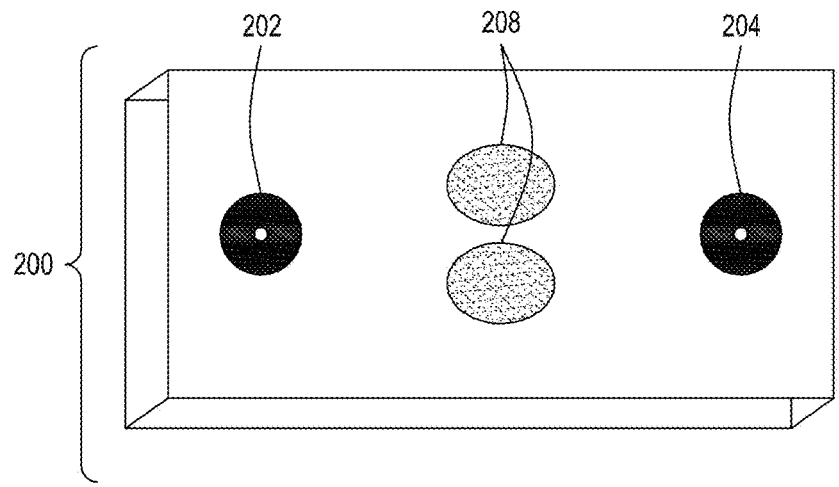
FIG. 2A is an illustration of a top view of another aspect of the FTEP devices of the disclosure.
Figure 2B:
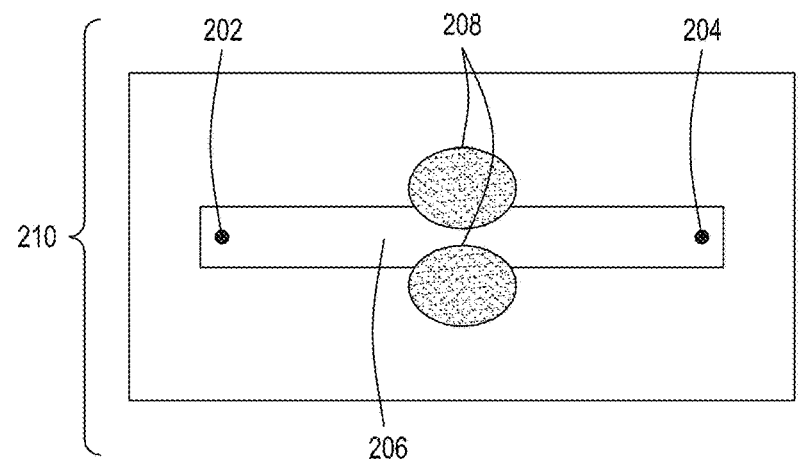
FIG. 2B is an illustration of the top view of a cross section of the aspect of the device shown in FIG. 2A.
Figure 2C:
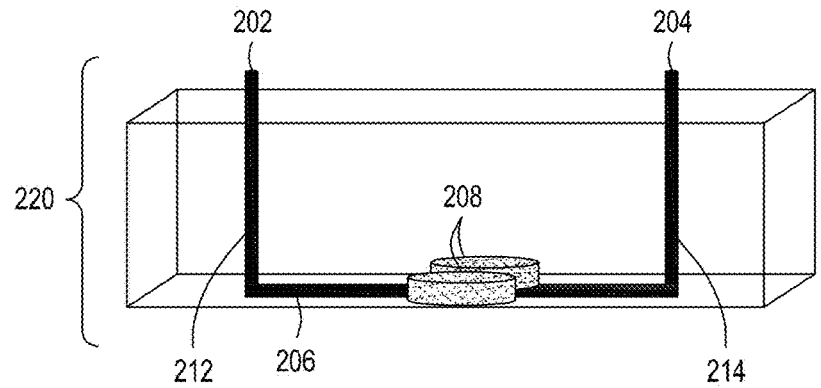
FIG. 2C is an illustration of a side view of a cross section of the aspect of the device shown in FIGS. 2A and 2B.

A second aspect of the FTEP devices described herein are illustrated in FIGS. 2A-2C. FIG. 2A shows a top planar view of an FTEP device 200 having an inlet 202 for introducing a fluid containing cells and exogenous material into the FTEP device 200 and an outlet 204 for removing the transformed cells following electroporation. Cylindrical electrodes 208 are positioned so as to define a center portion of the flow channel (not shown) where the flow channel narrows as a result of the curvature of the electrodes. FIG. 2B shows a cutaway view 210 from the top of the FTEP device 200, with the inlet 202, outlet 204, and electrodes 208 positioned with respect to a flow channel 206. Again, note that the electrodes 208 define a narrowed portion or region of flow channel 206. FIG. 2C shows a side cutaway view 220 of the device 200 with the inlet 202 and inlet channel 212, and outlet 204 and outlet channel 214. The electrodes 208 are cylindrical and positioned in the flow channel 206 defining a narrowed portion of the flow channel 206.

Figure 3A:
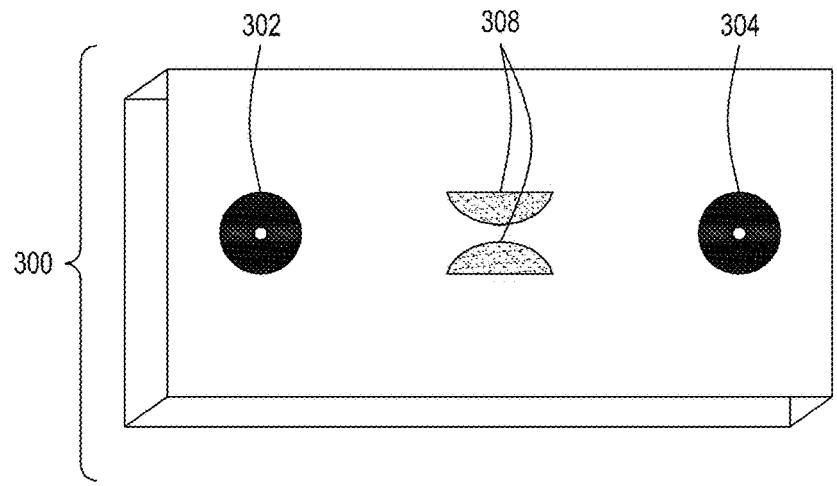
FIG. 3A is an illustration of a top view of yet another aspect of the FTEP devices of the disclosure.
Figure 3B:
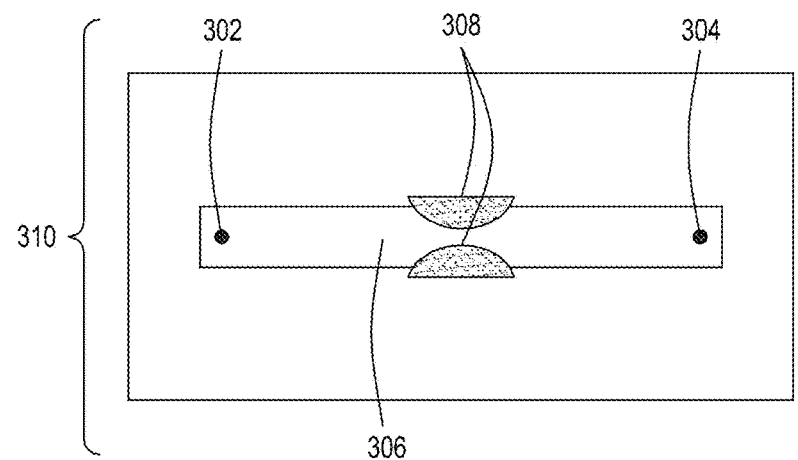
FIG. 3B is an illustration of the top view of a cross section of the aspect of the device shown in FIG. 3A.
Figure 3C:
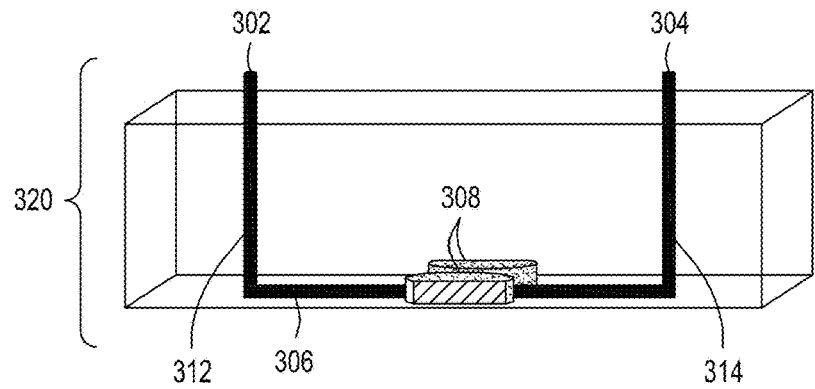
FIG. 3C is an illustration of a side view of a cross section of the aspect of the device shown in FIGS. 3A and 3B.

A third aspect of the FTEP devices of the disclosure are illustrated in FIGS. 3A-3C. FIG. 3A shows a top planar view of an FTEP device 300 having an inlet 302 for introducing a fluid containing cells and exogenous material into FTEP device 300, and an outlet 304 for removing the transformed cells following electroporation. The semi-cylindrical electrodes 308 are positioned so as to define a narrowed portion of a flow channel (not shown) where the channel narrows from both ends based on the curvature of the electrodes. FIG. 3B shows a cutaway view 310 from the top of the device 300, with the inlet 302, outlet 304, and electrodes 308 positioned with respect to a flow channel 306. FIG. 3C shows a side cutaway view 320 of the device 300 with the inlet 302 and inlet channel 312, and outlet 304 and outlet channel 314. The semi-cylindrical electrodes 308 are positioned in the flow channel 306 so that they define a narrowed portion of the flow channel 306. It should be noted that the devices depicted in FIGS. 1A-1C, 2A-2C, and 3A-3C show the electrodes positioned substantially mid-way along the flow channel; however, in other aspects of the devices, the electrodes may be positioned in narrowed regions of the flow channel more toward the inlet of the device or more toward the outlet of the device.

Figure 4A:
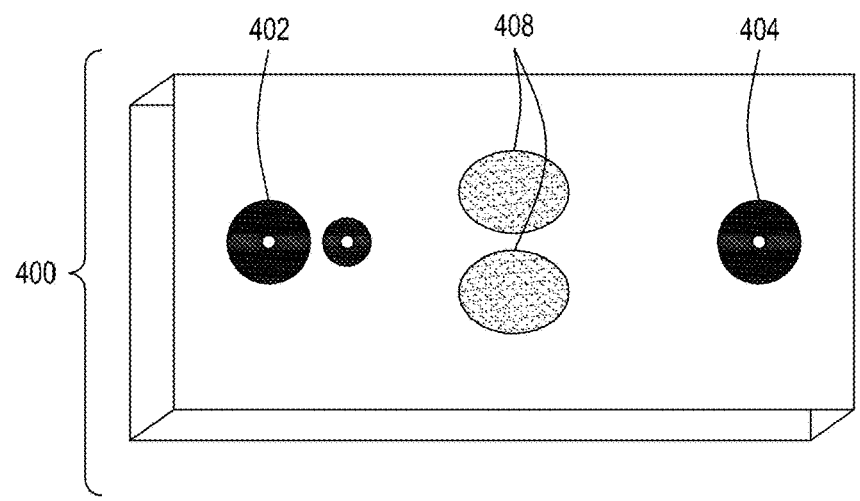
FIG. 4A is an illustration of the top view of a cross section of a further aspect of the FTEP devices described herein with separate inlets for the cells and the exogenous materials.
Figure 4B:
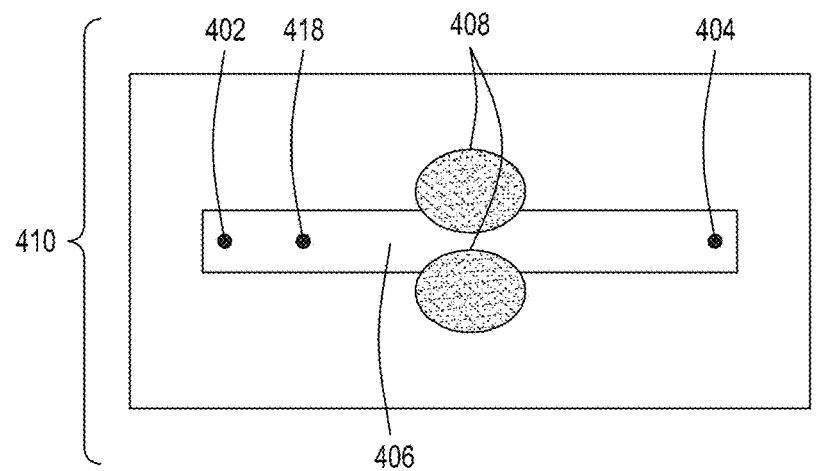
FIG. 4B is an illustration of the top view of a cross section of the aspect of the device shown in FIG. 4A.

FIGS. 4A-4E show aspects of the FTEP devices of the disclosure with separate inlets for the cells and the exogenous material. FIG. 4A shows a top planar view of an FTEP device 400 having a first inlet 402 for introducing a fluid containing cells into FTEP device 400; a second inlet 418 for introducing a fluid containing exogenous materials to be electroporated into the cells into FTEP device 400; electrodes 408; and an outlet 404 for removing the transformed cells following electroporation. Although these aspects are illustrated with cylindrical electrodes, as shown in FIG. 4A, other shaped electrodes with a curved edge—e.g., oval, semi-cylindrical, and the like as shown in relation to FIGS. 1A-1C and 3A-3C—may be used to define the flow channel as described in more detail herein. FIG. 4B shows a cutaway view 410 from the top of the device 400, with the first inlet 402, second inlet 418, outlet 404, and electrodes 408 positioned with respect to the flow channel 406.

Figure 4C:
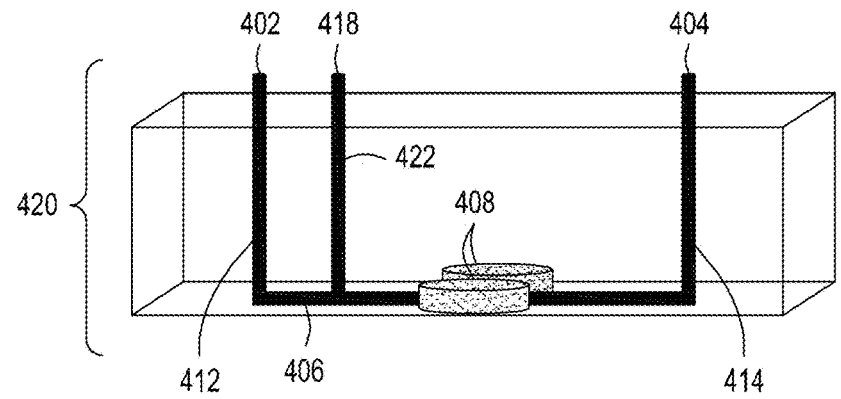
FIG. 4C is an illustration of a side view of a cross section of the aspect of the device shown in FIG. 4C.
Figure 4D:
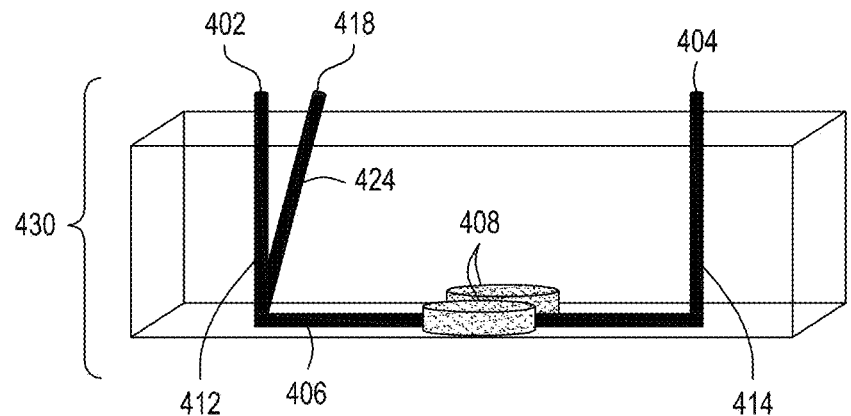
FIG. 4D is an illustration of a side view of a cross section of a variation on the aspect of the device shown in FIG. 4D.
Figure 4E:
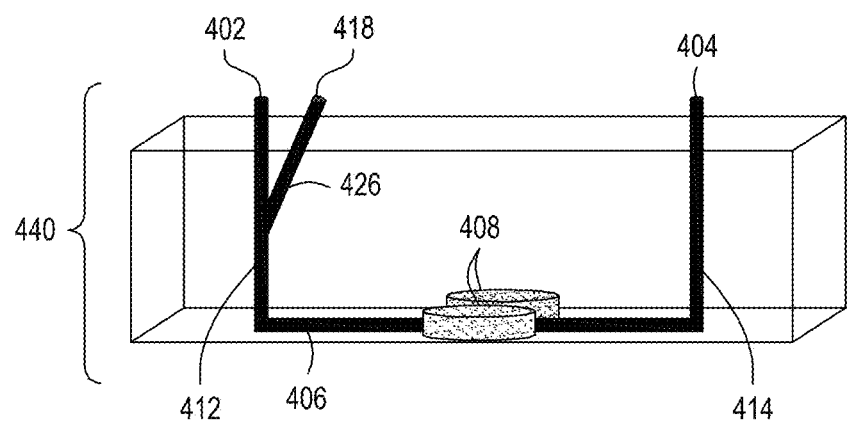
FIG. 4E is an illustration of a side view of a cross section of another variation on the aspect of the device shown in FIGS. 4C and 4D.

FIG. 4C shows a first side cutaway view 420 of the aspect of FTEP device 400 with the first inlet 402 and second inlet 418 positioned as shown in FIGS. 4A and 4B. In FIG. 4C, the first inlet channel 412 and second inlet channel 422 meet independently with flow channel 406, and the liquid (cells and material to be porated or delivered to the cells) flows through the flow channel 406 to the outlet channel 414 and outlet 404 where the transformed cells are removed from the FTEP device. The electrodes 408 are positioned in the flow channel 406 so that they define a narrowed portion of the flow channel 406. FIG. 4D shows a side cutaway view 430 of a variation on the aspect of the FTEP device 400 depicted in FIG. 4C. Here, the first inlet channel 412 and second inlet channel 424 intersect with the flow channel 406 at a three-way junction, and the liquid (cells and material to be porated or delivered to the cells) flows through the flow channel 406 to the outlet channel 414 and outlet 404 where the transformed cells are removed from the FTEP device. The electrodes 408 are positioned in the flow channel 406 defining a narrowed portion of the flow channel 406. FIG. 4E shows a first side cutaway view 440 of a yet another variation of the FTEP device 400 shown in FIGS. 4A and 4B. Here, the first inlet 402 and second inlet 418 intersect at a junction 426 where the cells and exogenous materials mix prior to introduction of the combined fluids to the flow channel 406. The fluids flow through the flow channel 406 to the outlet channel 414 and outlet 404 where the transformed cells are removed from the FTEP device. Electrodes 408 are positioned in the flow channel 406 so that they define a narrowed portion of the flow channel 406.

Figure 5A:
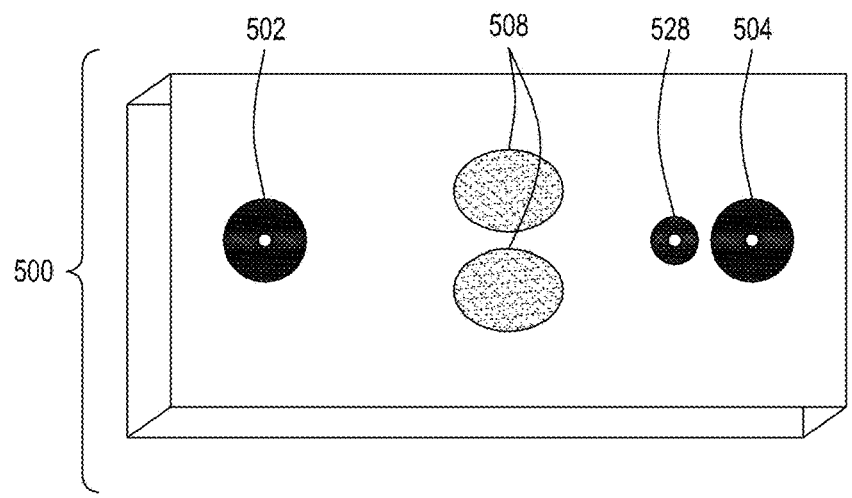
FIG. 5A is an illustration of the top view of a cross section of yet another aspect of the FTEP devices of the disclosure where the FTEP comprises two separate inlets for the cells and the exogenous materials.
Figure 5B:
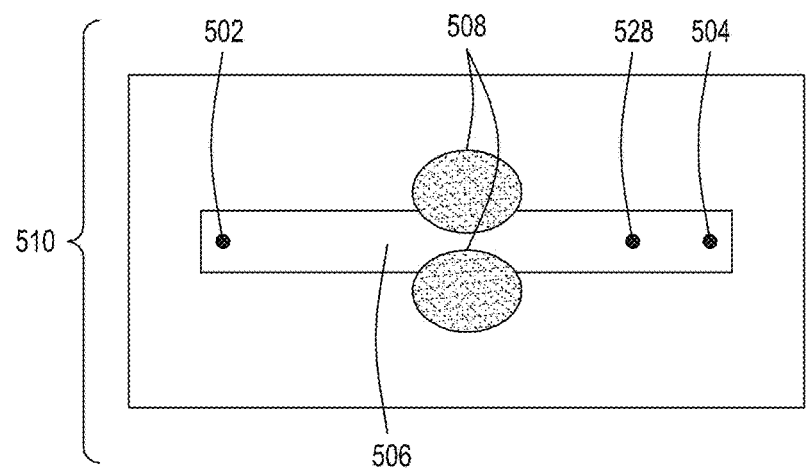
FIG. 5B is an illustration of a side view of a cross section of the aspect of the device shown in FIG. 5A.
Figure 5C:
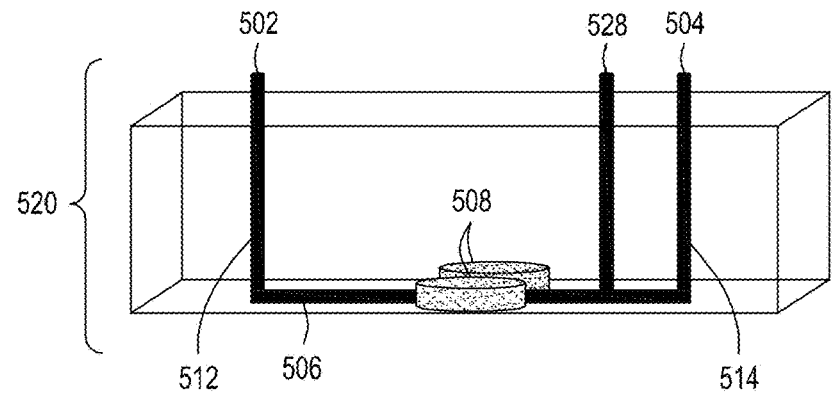
FIG. 5C is an illustration of a side view of a cross section of the aspect of the device shown in FIGS. 5A and 5B.

FIGS. 5A-5C show another aspect of the FTEP devices of the disclosure with separate inlets for the cells and the exogenous material. FIG. 5A shows a top planar view of an electroporation device 500 having a first inlet 502 for introducing a fluid containing cells, a second outlet 518 for introducing exogenous materials to be electroporated into the cells, and an outlet 504 for removing the transformed cells following electroporation. The electrodes 508 are positioned between the first inlet 502 where the cells are introduced into the FTEP device and the second inlet 528 where the exogenous materials are introduced into the FTEP device. FIG. 5B shows a cutaway view 510 from the top of the FTEP device 500, with the first inlet 502, second inlet 528, outlet 504, and the electrodes 508 positioned between the first inlet channel 502 and the second inlet channel 528, where the electrodes 508 form a narrowed portion of flow channel 506. FIG. 5C shows a side cutaway view 520 of the FTEP device 500 with the first inlet 502 where the cells are introduced into the FTEP device and first inlet channel 512, the second inlet 528 where the exogenous materials are introduced into the FTEP device and second inlet channel 532, and an outlet channel 514 and outlet 504 where the transformed cells are removed from the outlet 504 and device. The electrodes 508 are positioned in the flow channel 506 defining a narrow portion of the flow channel 506 and are positioned between the first inlet channel 512 and the second inlet channel 532 such that the material to be introduced into the cells is added to the fluid comprising the cells after the cells have been electroporated.

Figure 6:
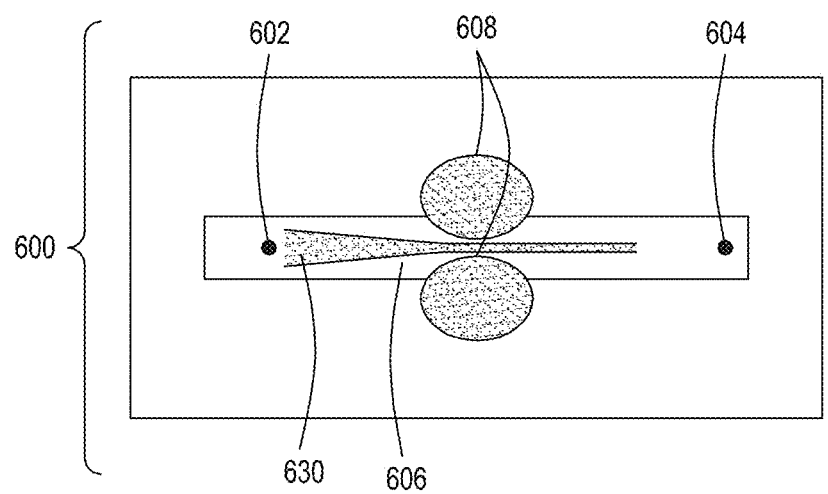
FIG. 6 is an illustration of a top view of a cross section of yet an additional aspect of the FTEP devices of the disclosure, here including flow focusing of fluid from the input channels.

FIG. 6 illustrates an FTEP device in which the flow of the fluid introduced into the flow channel from the input channel (s) is focused, e.g., using an immiscible fluid such as an oil or a stream of air to narrow the stream of the fluid containing the cells and the exogenous materials as it passes by the electrodes. FIG. 6 shows a cutaway view from the top of the FTEP device 600, with the first inlet 602, second inlet 630, outlet 604, and the electrodes 608 positioned between the first inlet channel 602 and outlet 604. The flow focusing is created using the immiscible fluid, where the electrodes 608 form a narrowed portion of flow channel 606. (For example, see, e.g., US Pub. No. 2010/0184928 to Kumacheva.)

Figure 7A:
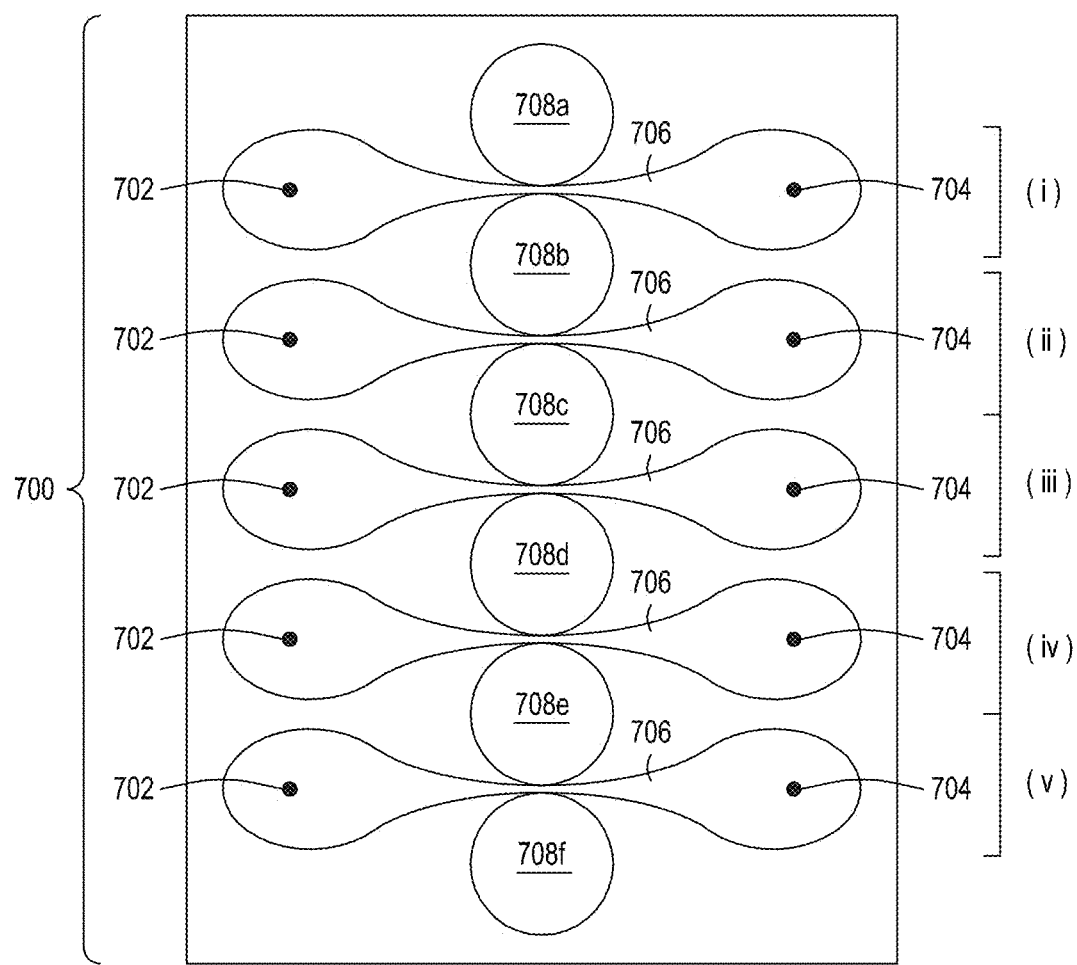
FIG. 7A is an illustration of a top view of a cross section of a first multiplexed aspect of the FTEP devices of the disclosure.
Figure 7B:
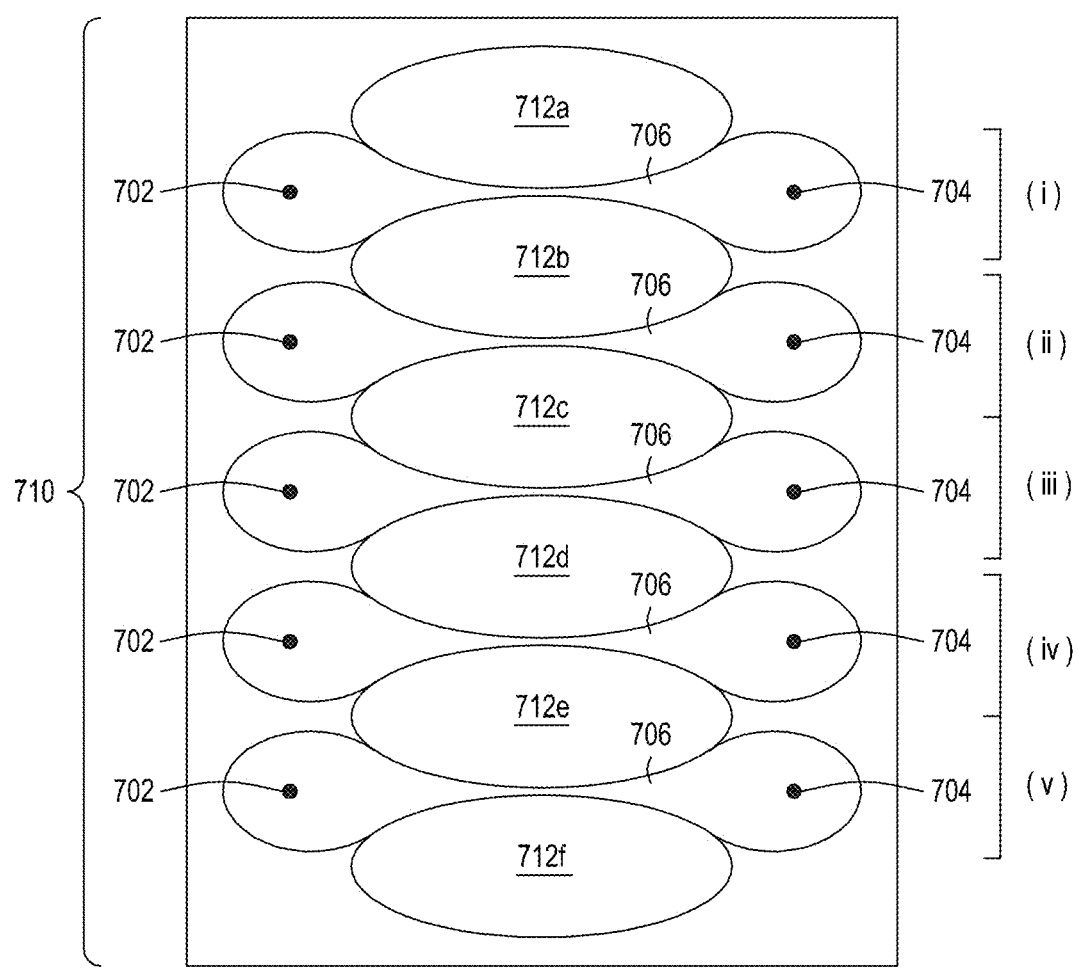
FIG. 7B is an illustration of a top view of a cross section of a second multiplexed aspect of the devices of the disclosure.

Multiplexed aspects of exemplary FTEP devices are illustrated in FIGS. 7A-7E. FIG. 7A illustrates a top view of a cross section of a first multiplexed aspect of the FTEP devices of the disclosure. The FTEP device in FIG. 7A is a multiplexed FTEP device 700 in which parallel flow channels 706 for each FTEP unit are defined in part by shared cylindrical electrodes 708a-708f forming devices (i), (ii), (iii), (iv), and (v). Each flow channel 706 has an inlet 702 for introducing different sets of cells and/or exogenous materials into the FTEP units and an outlet 704 for removing the transformed cells from the FTEP units. Adjacent units share electrodes, where the electrodes alternate charge, e.g., +/−/+/−/+(that is, if electrode 708a is +, electrode 708b is −, electrode 708c is +, electrode 708d is −, and so on). FIG. 7B is an illustration of a top view of a cross section of a second multiplexed aspect of the FTEP devices 710 of the disclosure. This is a multiplexed device 710 in which parallel flow channels 706 are defined in part by shared oval electrodes 708a-708f. Each flow channel 706 has an inlet 702 for introducing different sets of cells and/or exogenous materials into the flow channels 706, and an outlet for removing the transformed cells from FTEP units (i), (ii), (iii), (iv), and (v). Again, adjacent devices share electrodes, where the electrodes alternate charge, e.g., +/−/+/−/+.

Figure 7C:
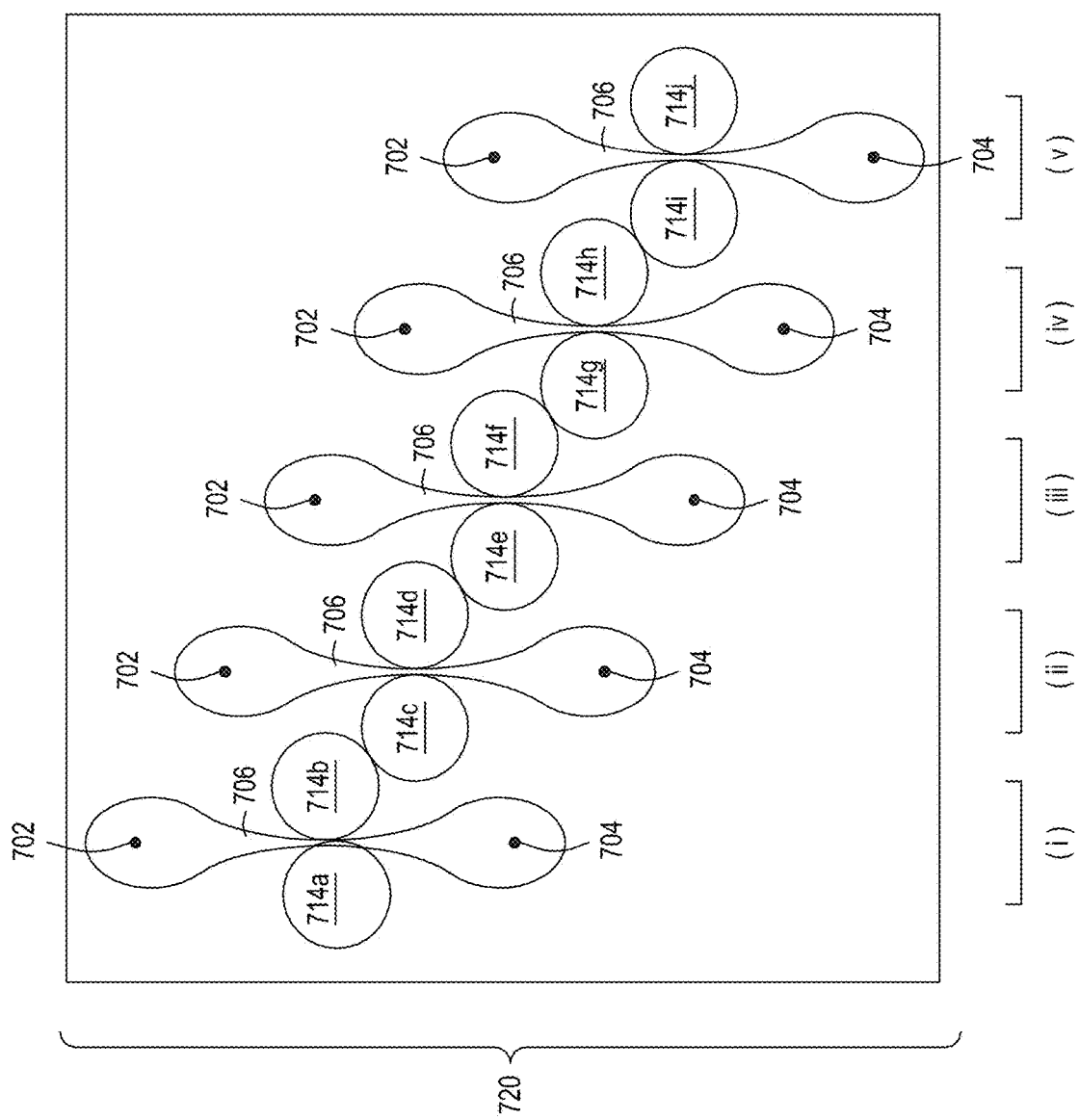
FIG. 7C is an illustration of a top view of a cross section of a third multiplexed aspect of the devices of the disclosure.
Figure 7D:
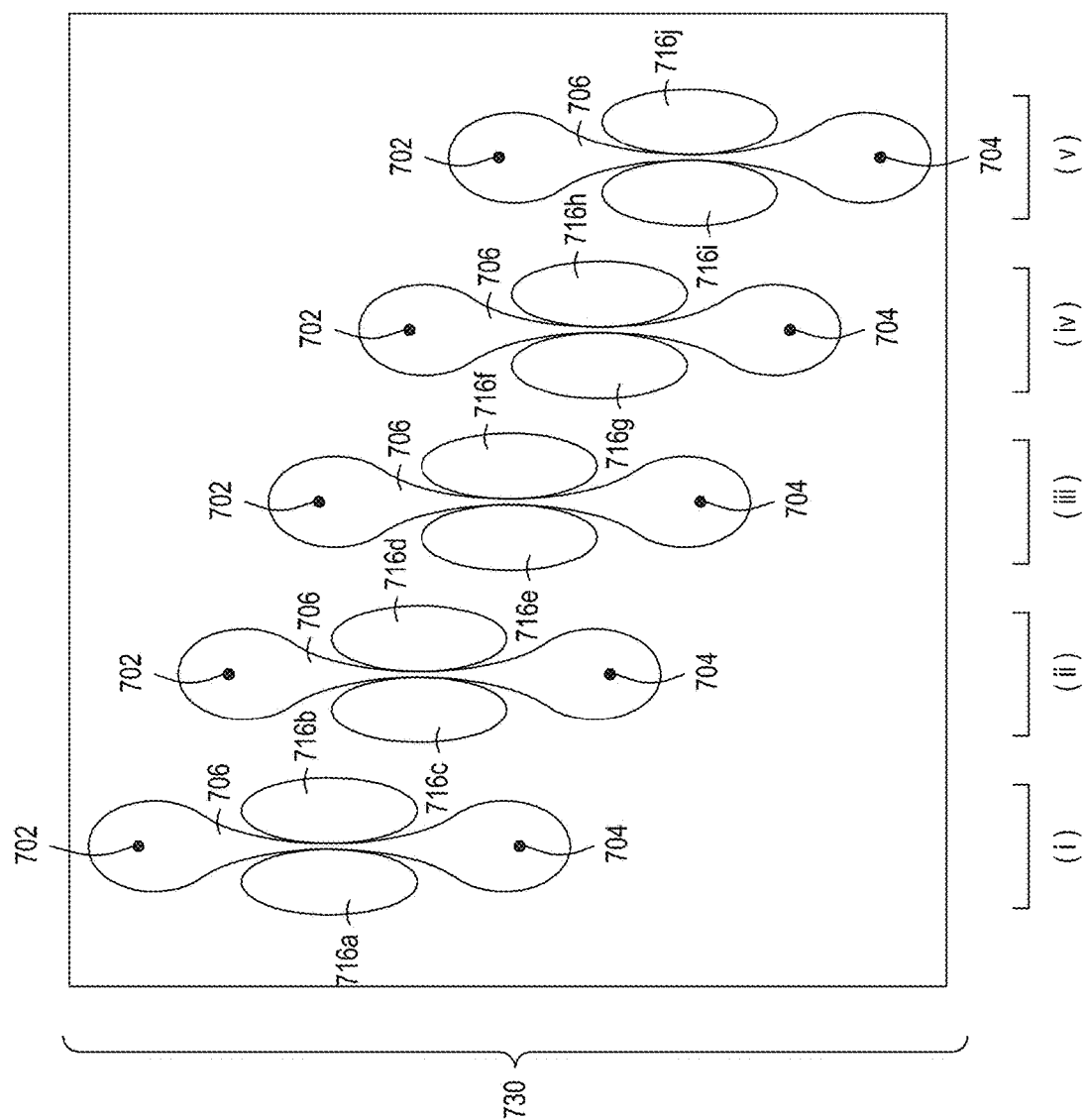
FIG. 7D is an illustration of a top view of a cross section of a fourth multiplexed aspect of the devices of the disclosure.
Figure 7E:
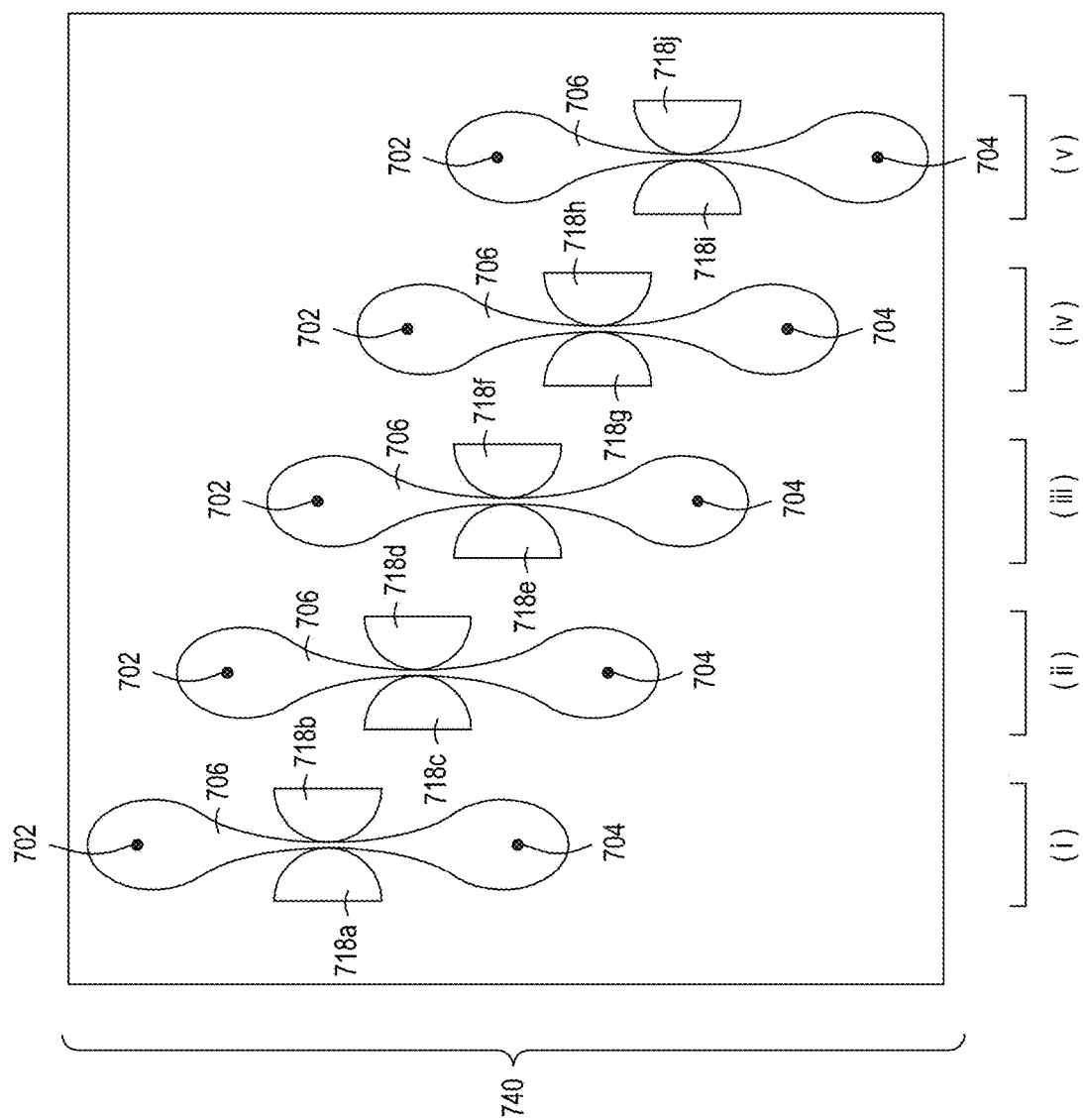
FIG. 7E is an illustration of a top view of a cross section of a fifth multiplexed aspect of the devices of the disclosure.

FIG. 7C is an illustration of a top view of a cross section of a third multiplexed aspect of the FTEP devices of the disclosure. In this exemplary multiplexed FTEP device 720, the individual FTEP units are staggered. The parallel flow channels 706 are defined in part by individual cylindrical electrodes 714a-714j that are not shared as shown in FIGS. 7A and 7B. Each flow channel 706 has its own pair of electrodes 708, an inlet 702 for introducing different sets of cells and/or exogenous materials into the FTEP device, and an outlet for removing transformed cells from the FTEP units (i), (ii), (iii), (iv), and (v). FIG. 7D is an illustration of a top view of a cross section of another exemplary multiplexed FTEP device. In this multiplexed FTEP device 730, staggered, parallel flow channels 706 are defined in part by individual oval electrodes 716a-716j. Each flow channel 706 has its own un-shared pair of electrodes 716 (e.g., 716a/716b, 716c/716d, 716e/716f, 716g/716h, and 716i/716j), an inlet 702 for introducing different sets of cells and/or exogenous materials into the FTEP units, and an outlet 704 for removing transformed cells from the FTEP units. FIG. 7E is an illustration of a top view of a cross section of another exemplary multiplexed FTEP device. In this exemplary multiplexed device 740, staggered, parallel flow channels 706 are defined in part by individual half-cylindrical electrodes 716a-716j. Each flow channel 706 has its own pair of electrodes 716, a separate inlet 702 for introducing different sets of cells and/or exogenous materials into the FTEP unit, and an outlet 704 for removing the transformed cells from the FTEP unit.

Figure 8A:
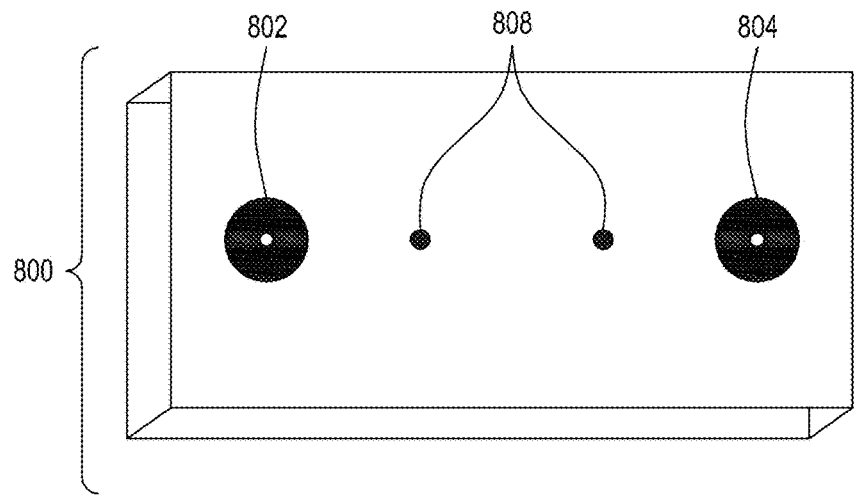
FIG. 8A is an illustration of a top view of yet another aspect of the FTEP devices of the disclosure.
Figure 8B:
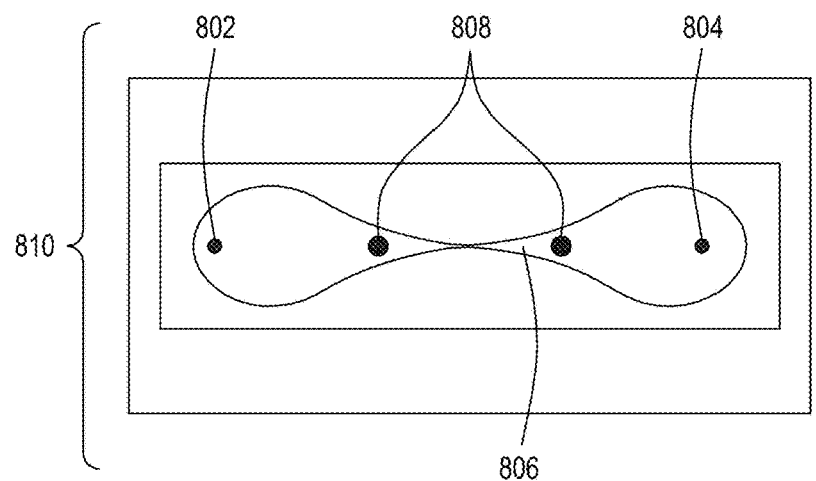
FIG. 8B is an illustration of the top view of a cross section of the aspect of the device shown in FIG. 8A.
Figure 8C:
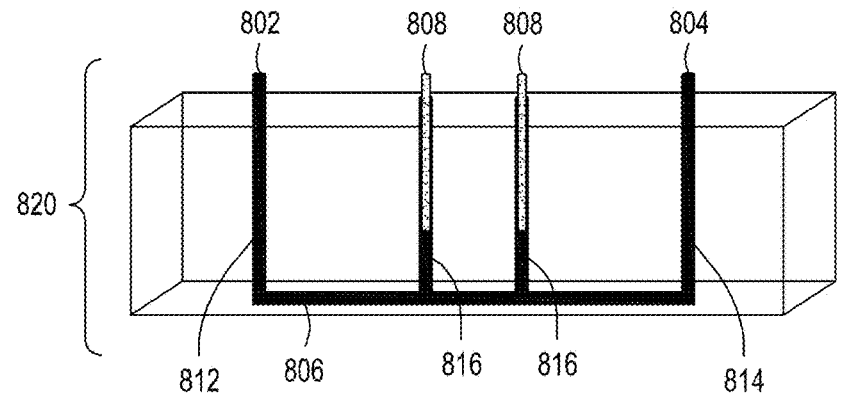
FIG. 8C is an illustration of a side view of a cross section of the aspect of the device shown in FIGS. 8A and 8B.
Figure 8D:
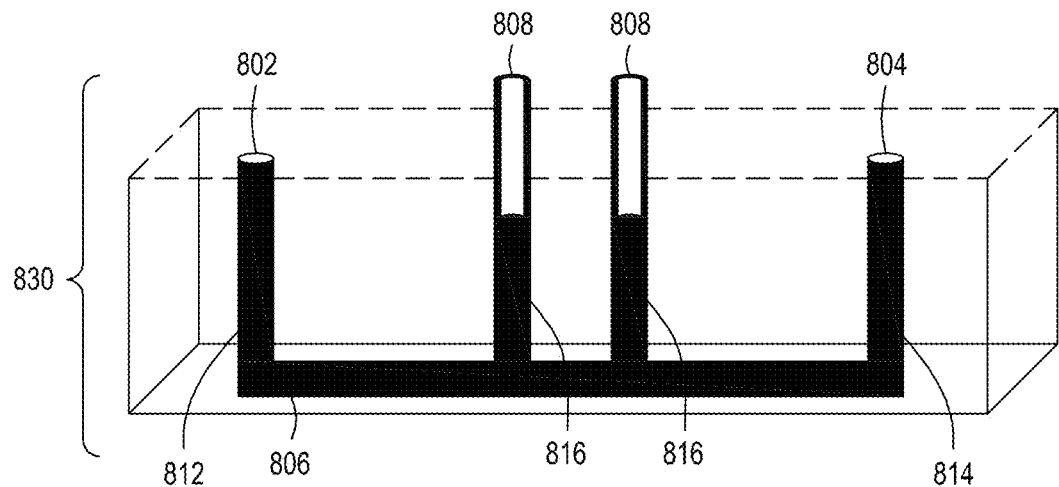
FIG. 8D is an illustration of a side view of a cross section of the bottom half of the aspect of the devices shown in FIGS. 8A, 8B and 8C.

Additional aspects of the FTEP devices of the disclosure are illustrated in FIGS. 8A-8E. Note that in the FTEP devices in FIGS. 8A-8E (and in FIGS. 9-14), the electrodes are not positioned on either side of the flow channel to narrow the flow channel; instead, the electrodes are placed such that a first electrode is placed between the inlet and the narrowed region of the flow channel, and the second electrode is placed between the narrowed region of the flow channel and the outlet. FIG. 8A shows a top planar view of an FTEP device 800 having an inlet 802 for introducing a fluid containing cells and exogenous material into FTEP device 800 and an outlet 804 for removing the transformed cells from the FTEP following electroporation. The electrodes 808 are introduced through channels (not shown) in the device. FIG. 8B shows a cutaway view 810 from the top of the device 800, with the inlet 802, outlet 804, and electrodes 808 positioned with respect to a flow channel 806. FIG. 8C shows a side cutaway view 820 of the device 800 with the inlet 802 and inlet channel 812, and outlet 804 and outlet channel 814. The electrodes 808 are positioned in electrode channels 816 so that they are in fluid communication with the flow channel 806, but not directly in the path of the cells traveling through the flow channel 806. Again, note that the first electrode is placed between the inlet and the narrowed region of the flow channel, and the second electrode is placed between the narrowed region of the flow channel and the outlet An expanded side cutaway view 830 of the bottom portion of the device 800 in FIG. 8D shows that the electrodes 808 in this first aspect of the device 830 are positioned in the electrode channels 816 which are generally perpendicular to the flow channel 806 such that the fluid containing the cells and exogenous material flows from the inlet channel 812 through the flow channel 806 to the outlet channel 814, and in the process fluid flows into the electrode channels 816 to be in contact with the electrodes 808. In this aspect, the inlet channel, outlet channel and electrode channels all originate from the same planar side of the device, as shown in FIGS. 8C and 8D. In certain aspects, however, such as that shown in FIG. 8E, the electrodes are introduced from a different planar side of the FTEP device than the inlet and outlet channels. Here, the electrodes 808 in this alternative aspect 840 of the device 800 are positioned in the electrode channels 816 perpendicular to the flow channel 806 such that fluid containing the cells and exogenous material flows from the inlet channel 812 through the flow channel 806 to the outlet channel 814. The cells and exogenous material in buffer flow into the electrode channels 816 to be in contact with both electrodes 808. In this aspect, the inlet channel and outlet channel originate from a different planar side of the device than do the electrodes and electrode channels.

Figure 8E:
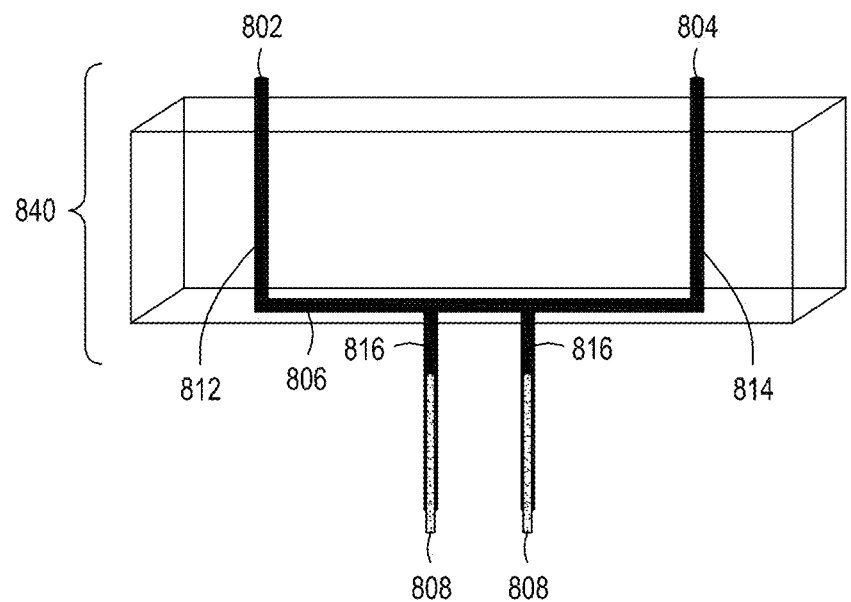
FIG. 8E is an illustration of a side view of a cross section of a variation of the aspect of the devices shown in FIGS. 8A-8D where here the electrodes are positioned on the bottom of the FTEP device.
Figure 9A:
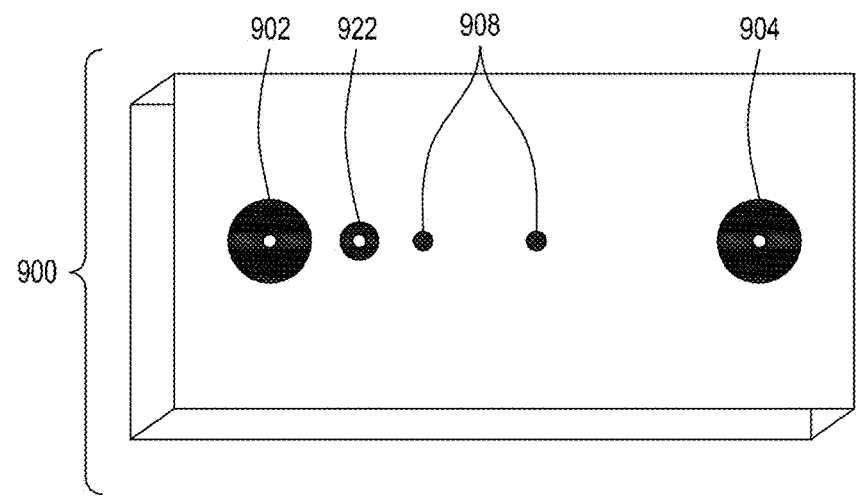
FIG. 9A is an illustration of a top view of yet another aspect of the FTEP devices of the disclosure.
Figure 9B:
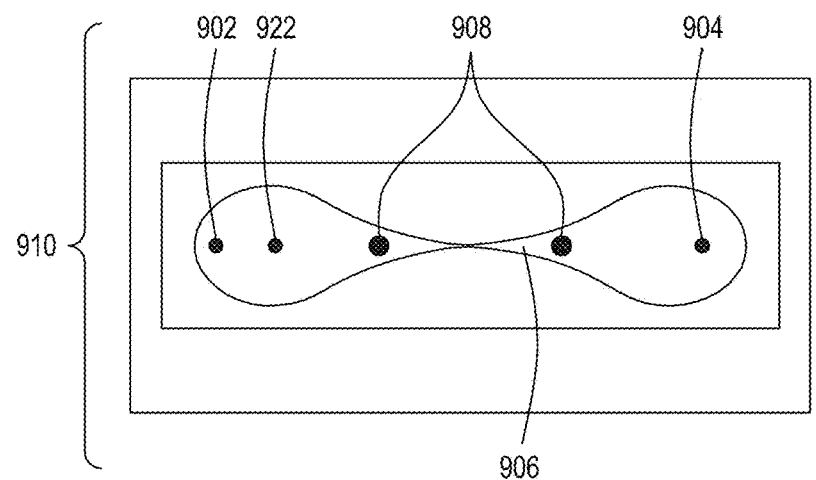
FIG. 9B an illustration of the top view of a cross section of the aspect of the device shown in FIG. 9A.
Figure 9C:
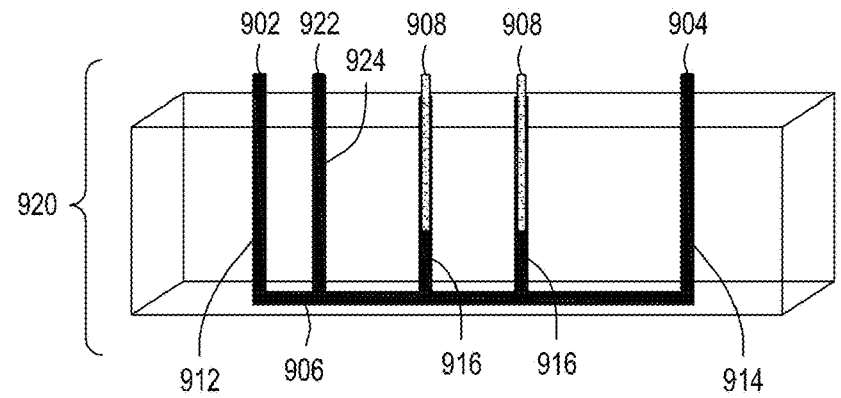
FIG. 9C is an illustration of a side view of a cross section of the aspect of the device shown in FIGS. 9A and 9B.

FIGS. 9A-9C illustrate yet another aspect of the FTEP devices of the disclosure. FIG. 9A shows a top planar view of an FTEP device 900 having a first inlet 902 for introducing a fluid containing cells into FTEP device 900 and an outlet 904 for removing the transformed cells from the FTEP device following electroporation. However, in this FTEP device, there is a second inlet 922 for introducing exogenous material to be electroporated to the cells. The electrodes 908 are introduced through channels (not shown) machined into the device. FIG. 9B shows a cutaway view 910 from the top of the FTEP device 900, with the first inlet 902, second inlet 922, outlet 904, and the electrodes 908 positioned with respect to the flow channel 906. FIG. 9C shows a side cutaway view 920 of the device 900 with the inlet 902 and inlet channel 912, and outlet 904 and outlet channel 914. The electrodes 908 are positioned in the electrode channels 916 so that they are in fluid communication with the flow channel 906, but not substantially in the path of the cells traveling through the flow channel 906. The electrodes 908 in this aspect of the FTEP device 920 are positioned in the electrode channels 916 where the electrode channels 916 are generally perpendicular to the flow channel 906 such that fluid containing the cells and fluid containing the exogenous materials flow from the inlets 902, 922 through the inlet channels 912, 924 into the flow channel 906 and through to the outlet channel 914, and in the process the cells and exogenous material in medium flows into the electrode channels 916 to be in contact with the electrodes 908. One of the two electrodes 908 and electrode channels 916 is positioned between inlets 902 and 922 and inlet channels 912 and 924 and the narrowed region (not shown) of flow channel 906, and the other electrode 908 and electrode channel 916 is positioned between the narrowed region (not shown) of flow channel 906 and the outlet channel 914 and outlet 904. In FIG. 9C, the inlet channel, outlet channel and electrode channels all originate from the same planar side of the device, although the electrodes (and inlets and outlet) can also be configured to originate from different planar sides of the FTEP device such as illustrated in FIG. 8E.

Figure 10A:
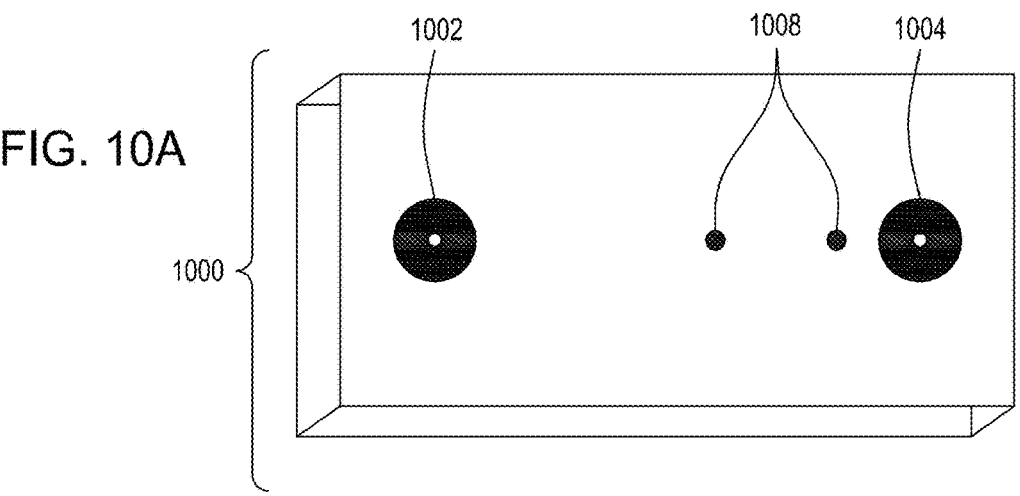
FIG. 10A is an illustration of a top view of an alternative aspect of the FTEP devices of the disclosure.
Figure 10B:
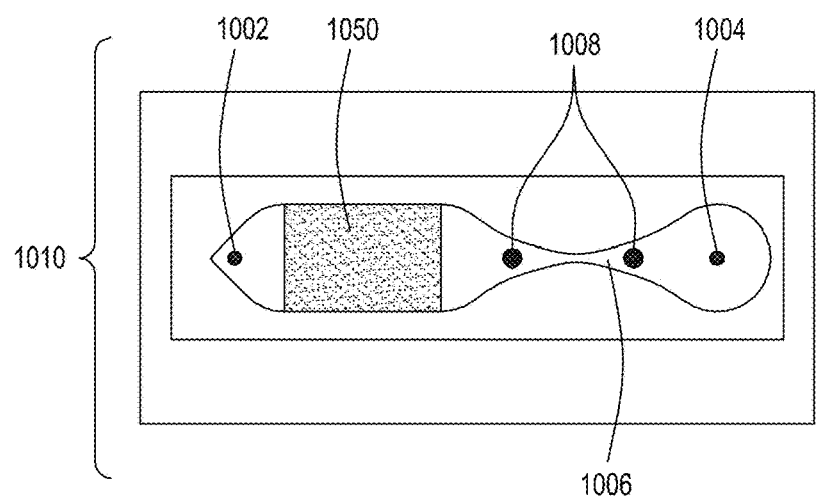
FIG. 10B is an illustration of the top view of a cross section of the aspect of the device shown in FIG. 10A.
Figure 10C:
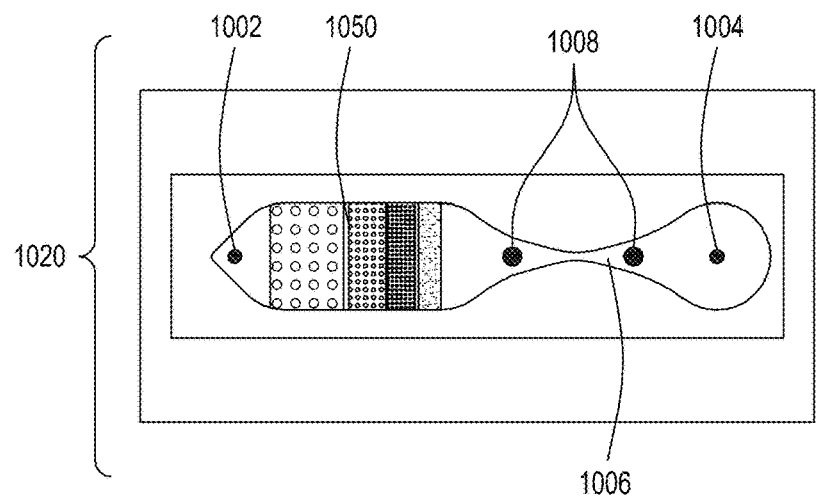
FIG. 10C is an illustration of the top view of a cross section of a variation of the aspect of the devices shown in FIGS. 10A and 10B.

FIGS. 10A-10E illustrate yet another aspect of the devices of the disclosure. FIG. 10A shows a top planar view of an electroporation device 1000 having an inlet 1002 for introducing a fluid containing cells and exogenous material into the FTEP device 1000 and an outlet 1004 for removal of the transformed cells from the FTEP device 1000 following electroporation. The electrodes 1008 are introduced through channels (not shown) machined into the device. FIG. 10B shows a cutaway view 1010 from the top of the device 1000, showing an inlet 1002, an outlet 1004, a filter of substantially uniform density 1050, and electrodes 1008 positioned with respect to the flow channel 1006. FIG. 10C shows a cutaway view 1020 from the top of an alternative configuration of the device 1000, with an inlet 1002, an outlet 1004, a filter of substantially increasing gradient density 1050, and electrodes 1008 positioned with respect to the flow channel 1006. In FIGS. 10A-E, like FIGS. 9A-9C, the first electrode is placed between the inlet and the narrowed region of the flow channel, and the second electrode is placed between the narrowed region of the flow channel and the outlet. In some embodiments such as those depicted in FIGS. 10A-10E, the FTEP devices comprise a filter disposed within the flow channel positioned in the flow channel after the inlet channel and before the first electrode channel. The filter may be substantially homogeneous in porosity (e.g., have a uniform density as in FIG. 10B); alternatively, the filter may increase in gradient density where the end of the filter proximal to the inlet is less dense, and the end of the filter proximal to the narrowed portion of the flow channel has greater gradient density (as shown in FIG. 10C). The filter may be fashioned from any suitable and preferably inexpensive material, including porous plastics, hydrophobic polyethylene, cotton, glass fibers, or the filter may be integral with and fabricated as part of the FTEP device body (see, e.g., FIG. 15E).

Figure 10D:
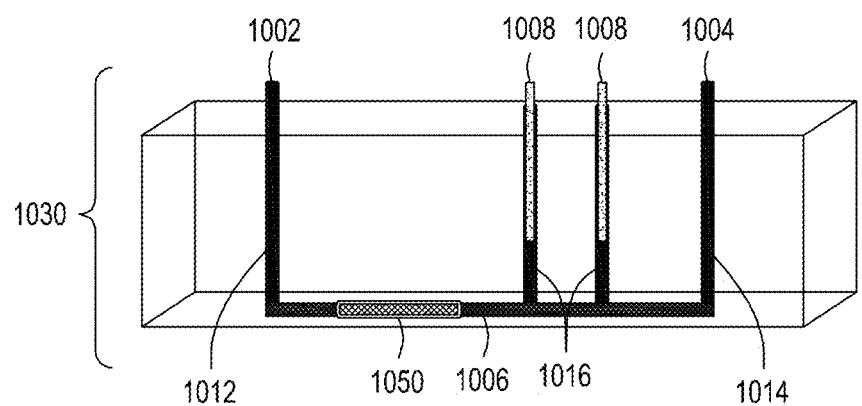
FIG. 10D is an illustration of a side view of a cross section of the aspects of the devices shown in FIGS. 10A-10C.
Figure 10E:
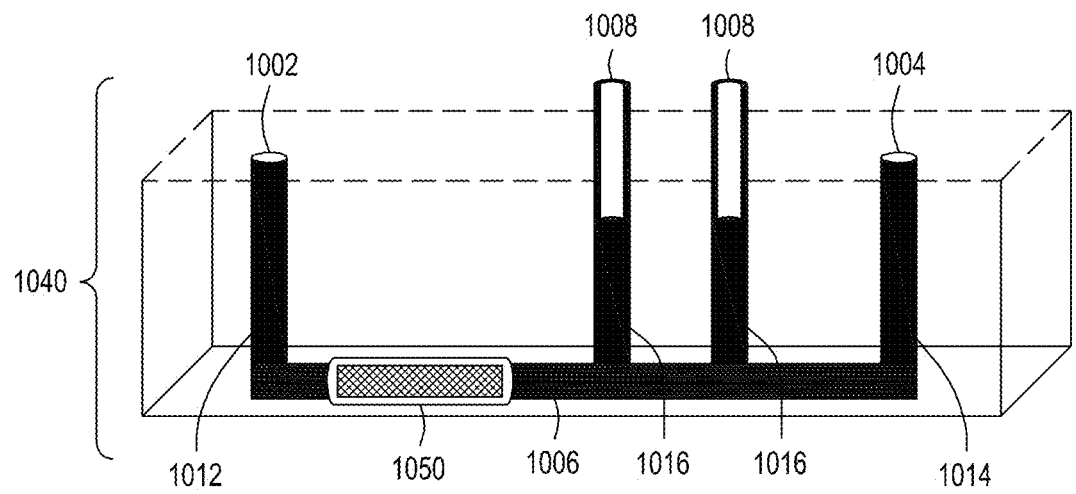
FIG. 10E is an illustration of a side view of a cross section of the bottom half of the aspects of the devices shown in FIGS. 10A-10D.

FIG. 10D shows a side cutaway view 1030 of the device 1000 with an inlet 1002 and an inlet channel 1012, and an outlet 1004 and an outlet channel 1014. The electrodes 1008 are positioned in the electrode channels 1016 so that they are in fluid communication with the flow channel 1006, but not directly in flow channel 1006. Note that filter 1050 is positioned between inlet 1002 and inlet channel 1012 and electrodes 1008 and electrode channels 1016. An expanded side cutaway view 1040 of the bottom portion of the FTEP device 1000 in FIG. 10E shows that the electrodes 1008 in this aspect of the FTEP device 1000 are positioned in the electrode channels 1016 and perpendicular to the flow channel 1006 such that fluid containing the cells and exogenous material flows from the inlet channel 1012 through the flow channel 1006 to the outlet channel 1014, and in the process fluid flows into the electrode channels 1016 to be in contact with both electrodes 1008. In FIGS. 10D and 10E, the inlet channel, outlet channel and electrode channels all originate from the same planar side of the device, although the electrodes (and the inlets and outlet) can also be configured to originate from a different planar side such as illustrated in FIG. 8E.

Figure 11A:
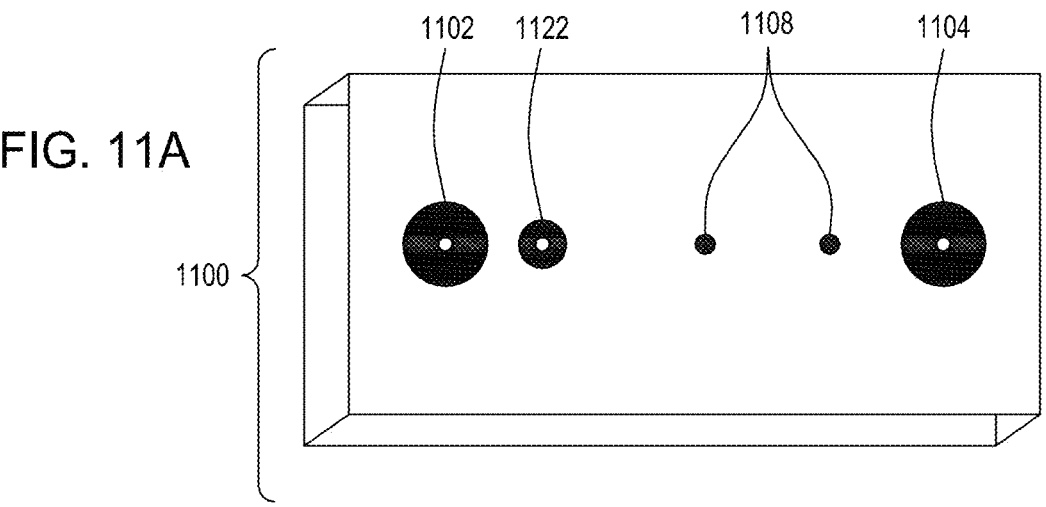
FIG. 11A is an illustration of a top view of yet another aspect of the FTEP devices of the disclosure.
Figure 11B:
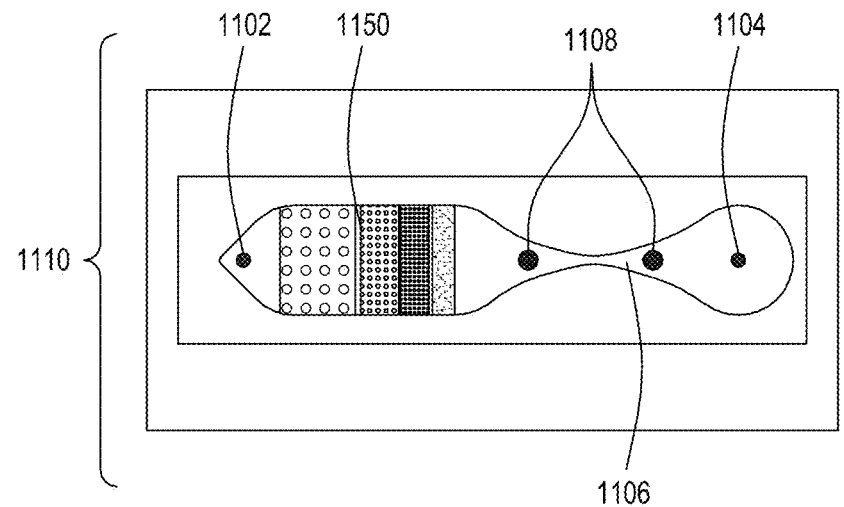
FIG. 11B is an illustration of the top view of a cross section of the aspect of the device shown in FIG. 11A.
Figure 11C:
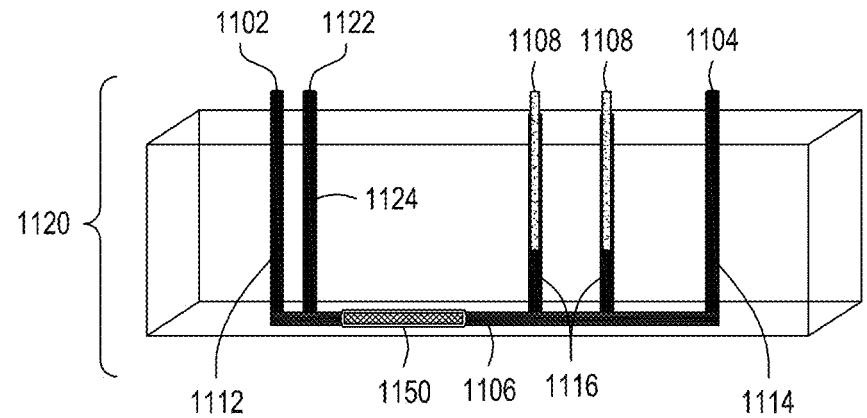
FIG. 11C is an illustration of a side view of a cross section of the aspect of the device of the disclosure shown in FIGS. 11A-11B.

FIGS. 11A-11E illustrate other aspects of the FTEP devices of the disclosure. FIG. 11A shows a top view of an FTEP device 1100 having a first inlet 1102 for introducing a fluid containing cells into the FTEP device and a second inlet 1122 for introducing a fluid containing exogenous materials to be introduced to the cells into the FTEP device, electrodes 1108 positioned in electrode channels (not shown), and an outlet 1104 for removal of the transformed cells following electroporation. FIG. 11B shows a cutaway view 1110 from the top of the device 1100, comprising a first inlet 1102, second inlet 1122, outlet 1104, filter 1150, and electrodes 1108 positioned with respect to the flow channel 1106. Again, note that the electrodes 1108 are positioned so that the first electrode is on the "inlet end" of the narrowed region in flow channel 1106 and the second electrode is on the "outlet end" of the narrowed region in flow channel 1106. FIG. 11C shows a first side cutaway view 1120 of a fifth aspect of the device 1100 with the first inlet 1102 and second inlet 1122 positioned as shown in FIG. 11A. The first inlet channel 1112 and second inlet channel 1124 meet separately with the flow channel 1106 prior to encountering filter 1150, and the liquid flows from the inlet channels 1112 and 1124 through the flow channel 1106 (and filter 1150) to the outlet channel 1114 and outlet 1104. The electrodes 1108 are positioned in the electrode channels 1116 so that they are in fluid communication with the flow channel 1106, but not directly in flow channel 1106. Note that in some embodiments, electrodes 1108 may be positioned in electrode channels 1116 such that electrodes 1108 are flush with the walls of flow channel 1106 (e.g., see FIG. 15F(iii)). Alternatively, electrodes 1108 may extend a minimal distance into flow channel 1106; however, in doing so electrodes 1108 do not extend into flow channel 1106 to the extent that the electrodes impede the flow of the cells through the flow channel.

Figure 11D:
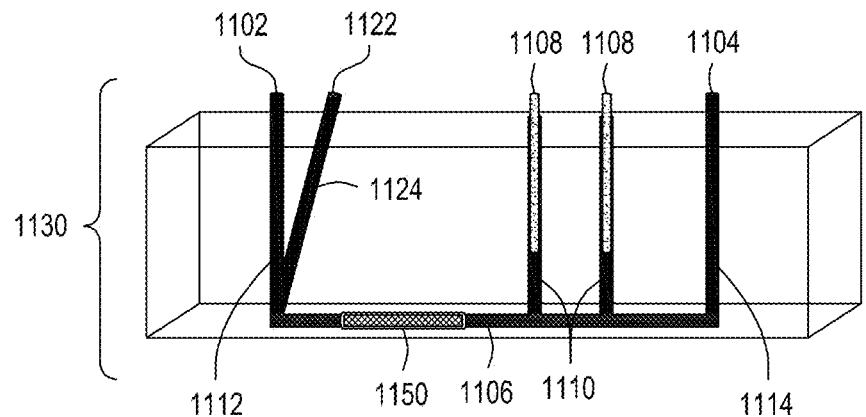
FIG. 11D is an illustration of a side view of a cross section of a variation on the aspect of the device shown in FIGS. 11A-11B.
Figure 11E:
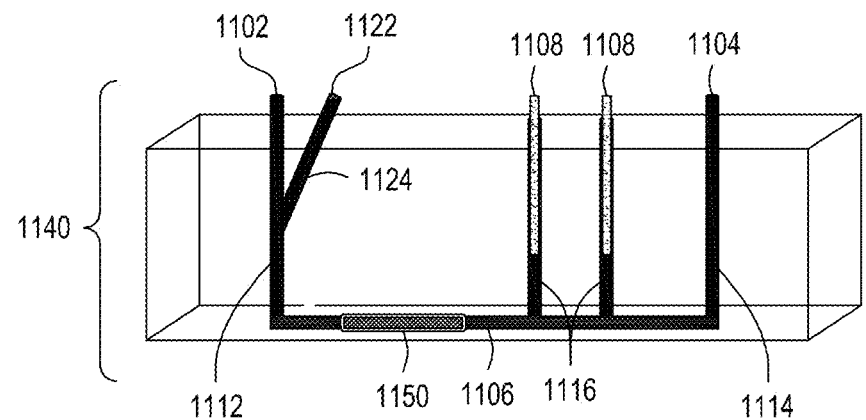
FIG. 11E is an illustration of a side view of a cross section of a variation on the aspect of the device shown in FIGS. 11A-11B.

FIG. 11D shows a side cutaway view 1130 of a variation of the aspect of the FTEP device 1100 shown in FIGS. 11A-11C with the first inlet 1102 and second inlet 1122 positioned as shown in FIG. 11A. The first inlet channel 1112 and second inlet channel 1124 intersect with flow channel 1106 at a three-way junction with flow channel 1106 and prior to encountering filter 1150. The liquid flows through the flow channel 1106 to the outlet channel 1114 and outlet 1104. The electrodes 1108 are positioned in the electrode channels 1116 so that they are in fluid communication with the flow channel 1106, but not directly in the flow channel 1106. Again, the electrodes 1108 are positioned so that the first electrode is on the "inlet end" of the narrowed region in flow channel 1106 and the second electrode is on the "outlet end" of the narrowed region in flow channel 1106. FIG. 11E shows a side cutaway view 1140 of yet another variation on the aspect of the FTEP device 1100 shown in FIGS. 11A-11C. The first inlet channel 1112 and second inlet channel 1126 intersect at a junction into a single channel prior to intersecting flow channel 1106. The fluids flow from the inlets 1102 and 1122, through the inlet channels 1112 and 1126, into and through flow channel 1106 and the filter 1150, into electrode channels 1116 (such that electrodes 1108 are in fluid communication with flow channel 1106) and continuing through flow channel 1106 to the outlet channel 1114 and finally to the outlet 1104 where the transformed cells are removed from the FTEP device 1100. The electrodes 1108 are positioned in the electrode channels 1116 so that they are in fluid communication with the flow channel 1106, but not directly in the flow path of the cells traveling through the flow channel 1106. Although each of FIGS. 11C-11E show the inlet channels, outlet channel and electrode channels originating from the same planar side of the device, all of the inlets, outlet and electrodes in each of these aspects can also be configured to originate from different planar sides of the FTEP device.

Figure 12A:
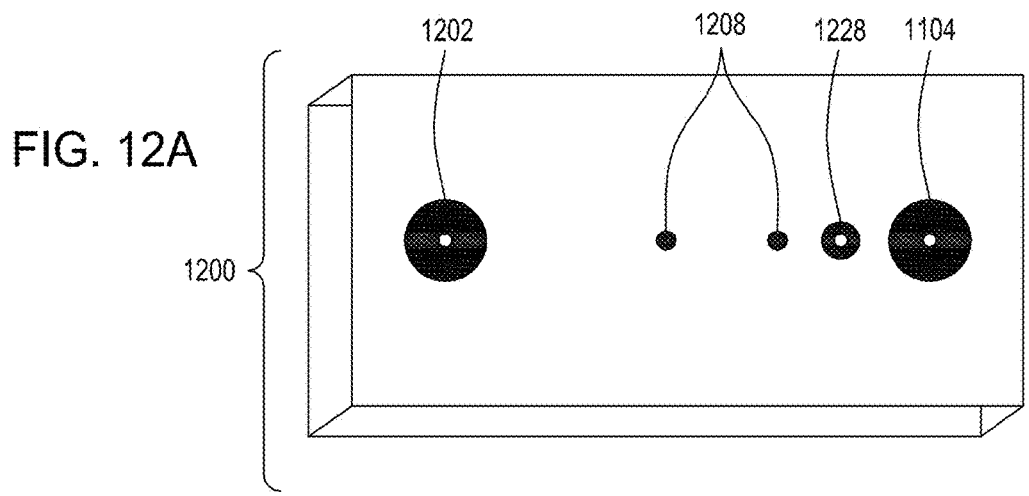
FIG. 12A is an illustration of the top view of a cross section of yet another aspect of the FTEP devices of the disclosure.
Figure 12B:
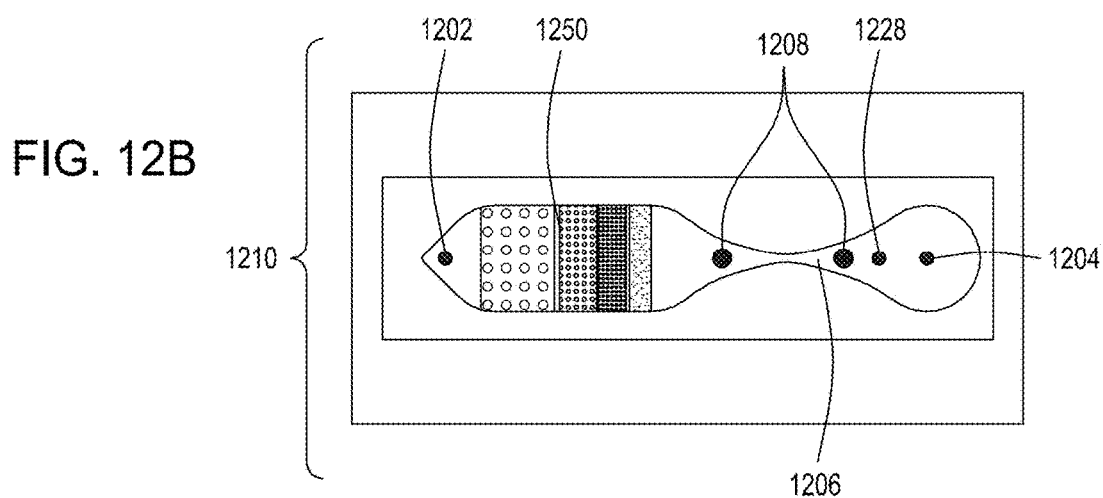
FIG. 12B is an illustration of the top view of a cross section of the aspect of the device shown in FIG. 12A.
Figure 12C:
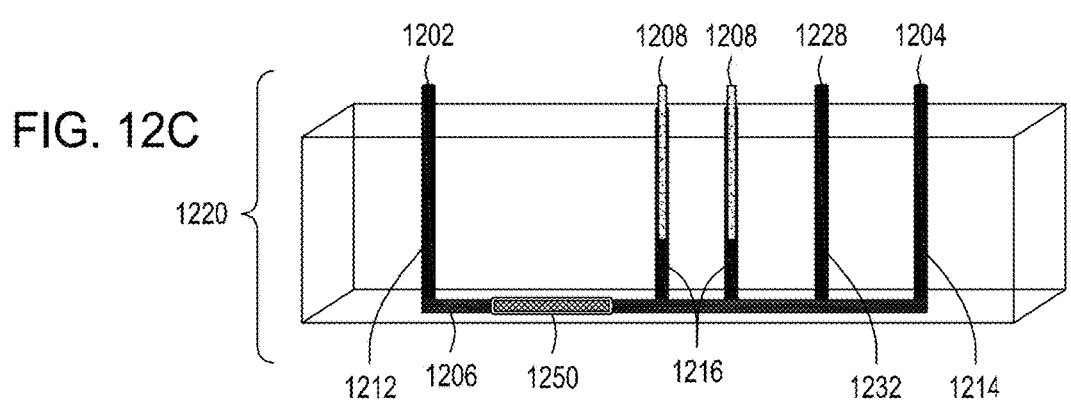
FIG. 12C is an illustration of a side view of a cross section of the aspect of the device shown in FIGS. 12A and 12B.

FIGS. 12A-12C illustrate another aspect of the FTEP devices of the disclosure. FIG. 12A shows a top view of an electroporation device 1200 having a first inlet 1202 for introducing a fluid containing cells into FTEP device 1200, a second inlet 1228 for introducing exogenous materials to be porated into the cells into FTEP device 1200, and an outlet 1204 for removing transformed cells from FTEP device 1200 following electroporation. The electrodes 1208 are introduced through channels (not shown) machined into the device and are positioned between the first inlet 1202 and the second inlet 1228. FIG. 12B shows a cutaway view 1210 from the top of the device 1200, with the first inlet 1202, second inlet 1228, outlet 1204, and the electrodes 1208 positioned with respect to the flow channel 1206. Additionally, the FTEP device depicted in FIG. 12B comprises a filter disposed between the first inlet 1202 and the first electrode 1208 and before the narrowed region of flow channel 1206. Filter 1250 in this embodiment has a gradient of pore sizes, from large to small. FIG. 12C shows a side cutaway view 1220 of FTEP device 1200 comprising a first inlet 1202 and first inlet channel 1212, a filter 1250, a second inlet 1228 and second inlet channel 1232, and an outlet 1204 and outlet channel 1214. The electrodes 1208 are positioned in the electrode channels 1216 perpendicular to flow channel 1206 and between the first and second inlets. The electrodes 1208 are in fluid communication with flow channel 1206, but not substantially in the flow path of the cells traveling through flow channel 1206. Exogenous materials are added to FTEP device 1200 via the second inlet 1228 and through the second inlet channel 1232 and encounter the cells after the cells are electroporated. In FIG. 12C, the inlet channels, outlet channel and electrode channels all originate from the same planar side of the device, although these features can also be configured to originate from different planar sides of FTEP device 1200.

Figure 13A:
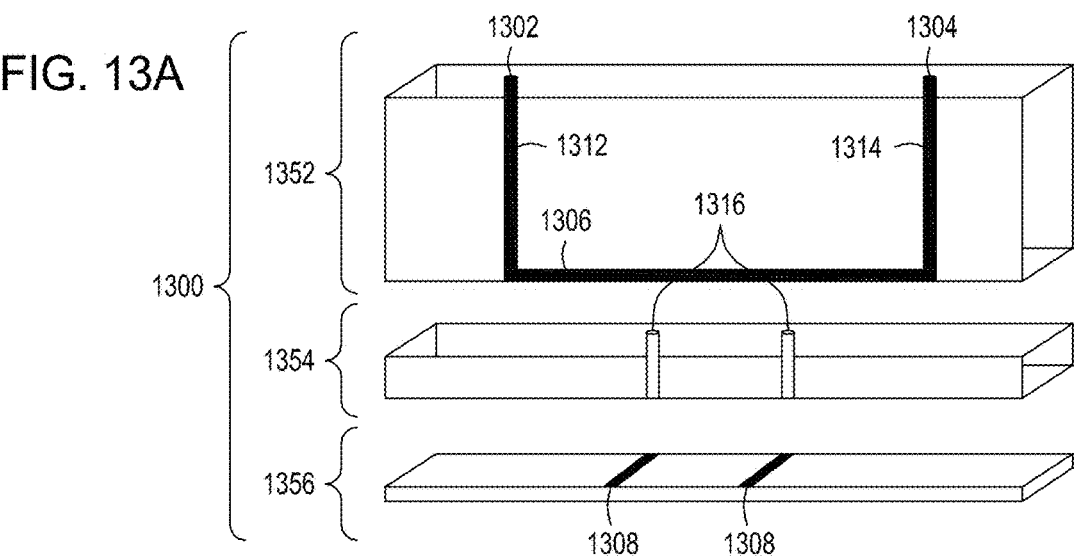
FIG. 13A is an illustration of a side view of a cross section of another aspect of the FTEP devices of the disclosure.
Figure 13B:
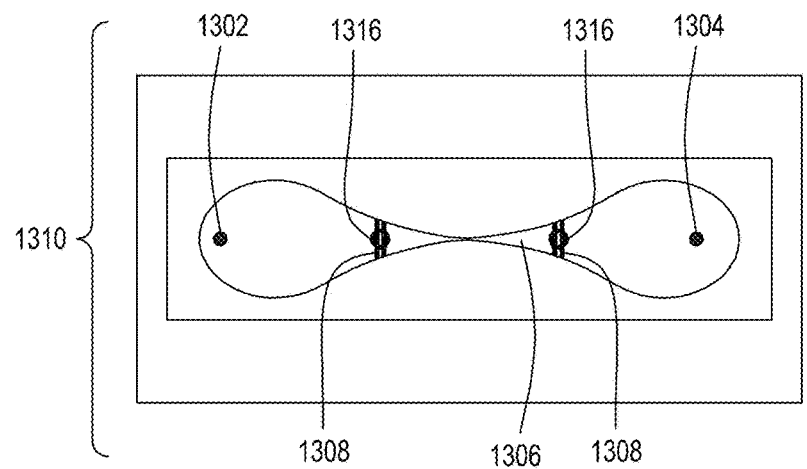
FIG. 13B is an illustration of the top view of a cross section of the aspect of the devices shown in FIG. 13A.

FIGS. 13A and 13B show the side and top cutaway views, respectively, of yet another aspect of the invention. FIG. 13A shows a multilayer device 1300 with a top layer 1352 having an inlet 1302 and an inlet channel 1312, a flow channel 1306, and outlet 1304 and an outlet channel 1314. The electrodes 1308 are on bottom layer 1356, e.g., provided as strips on a solid substrate. The middle layer 1354 is a solid substrate with electrode channels 1316 provided therein, and the electrode channels 1316 in this aspect provide fluid communication between the electrodes 1308 of bottom layer 1356 and flow channel 1306 of top layer 1352. The cells and exogenous materials in fluid are introduced to the FTEP device 1300 via inlet 1302 and flow through inlet channel 1312 and into flow channel 1306, and then to the outlet channel 1314. In the process, the fluid flows into electrode channels 1316 so that electrodes 1308 are in fluid contact with flow channel 1306. The cells are porated as they pass through flow channel 1306 between the two electrodes 1308. FIG. 13B shows the top view of a cutaway 1310 of this aspect of the FTEP device 1300 showing the position of the inlet 1302, outlet 1304, electrodes 1308 and electrode channels 1316 with respect to the flow channel 1306. Although the electrodes are shown here as strips, they may also be configured to be other shapes, e.g., round, cylindrical, asymmetric, rectangular, or square.

Figure 14:
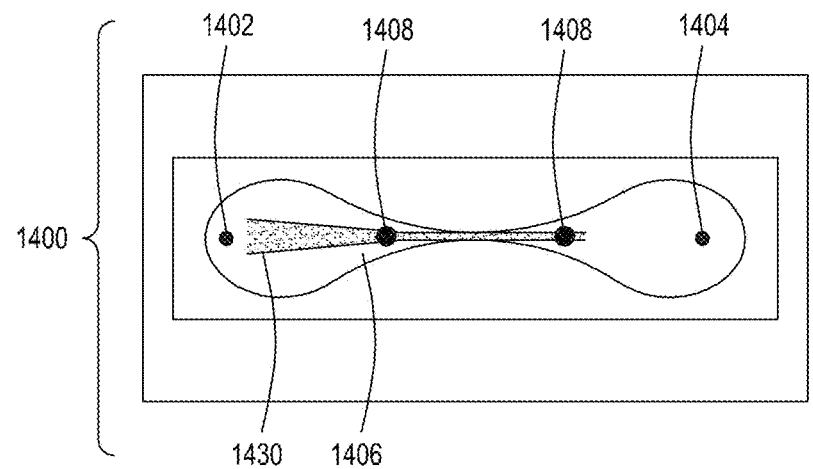
FIG. 14 is an illustration of a top view of a cross section of an aspect of an FTEP device with a flow focusing feature.

FIG. 14 illustrates an FTEP device in which flow focusing of the fluid introduced into the flow channel from the input channel(s) takes place, e.g., using an immiscible fluid such as an oil or using air to focus (narrow) the stream of the fluid containing the cells and exogenous materials as the fluid encounters the electrode channels, and the electrodes. FIG. 14 shows a cutaway view from the top of the device 1400, with the first inlet 1402, the flow focusing of the fluid after it exits the inlet channel and enters the flow channel 1406, and the electrodes 1408 positioned between the inlet 1402 and the outlet 1404, where the electrodes 1408 are positioned on either end of a narrowed portion of flow channel 1406.

Figure 15A:
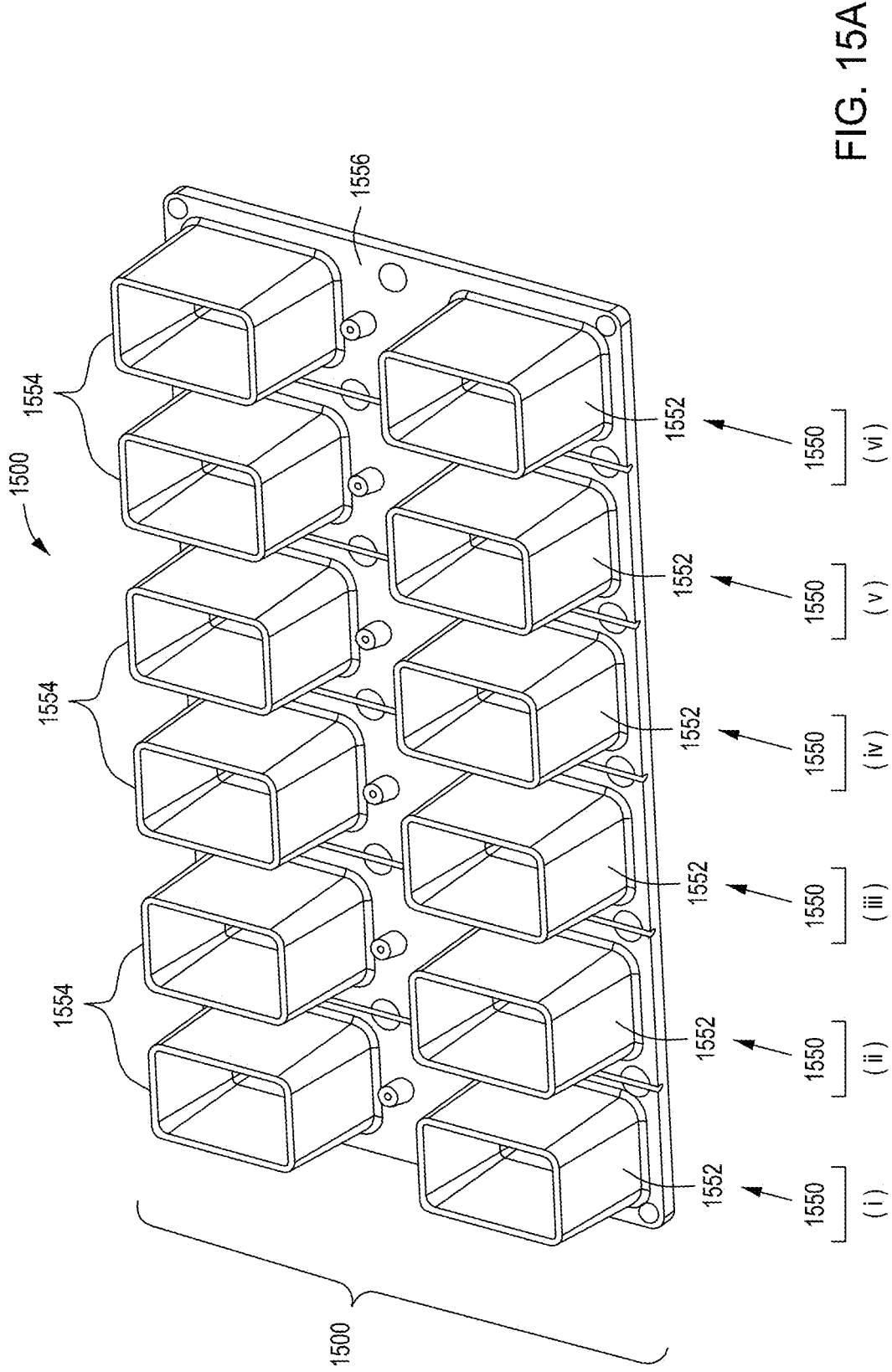
FIGS. 15A through 15C are top perspective, bottom perspective, and bottom views, respectively, of a flow-through electroporation device that may be part of a stand-alone FTEP module or as one module in an automated multi-module cell processing system.
Figure 15B:
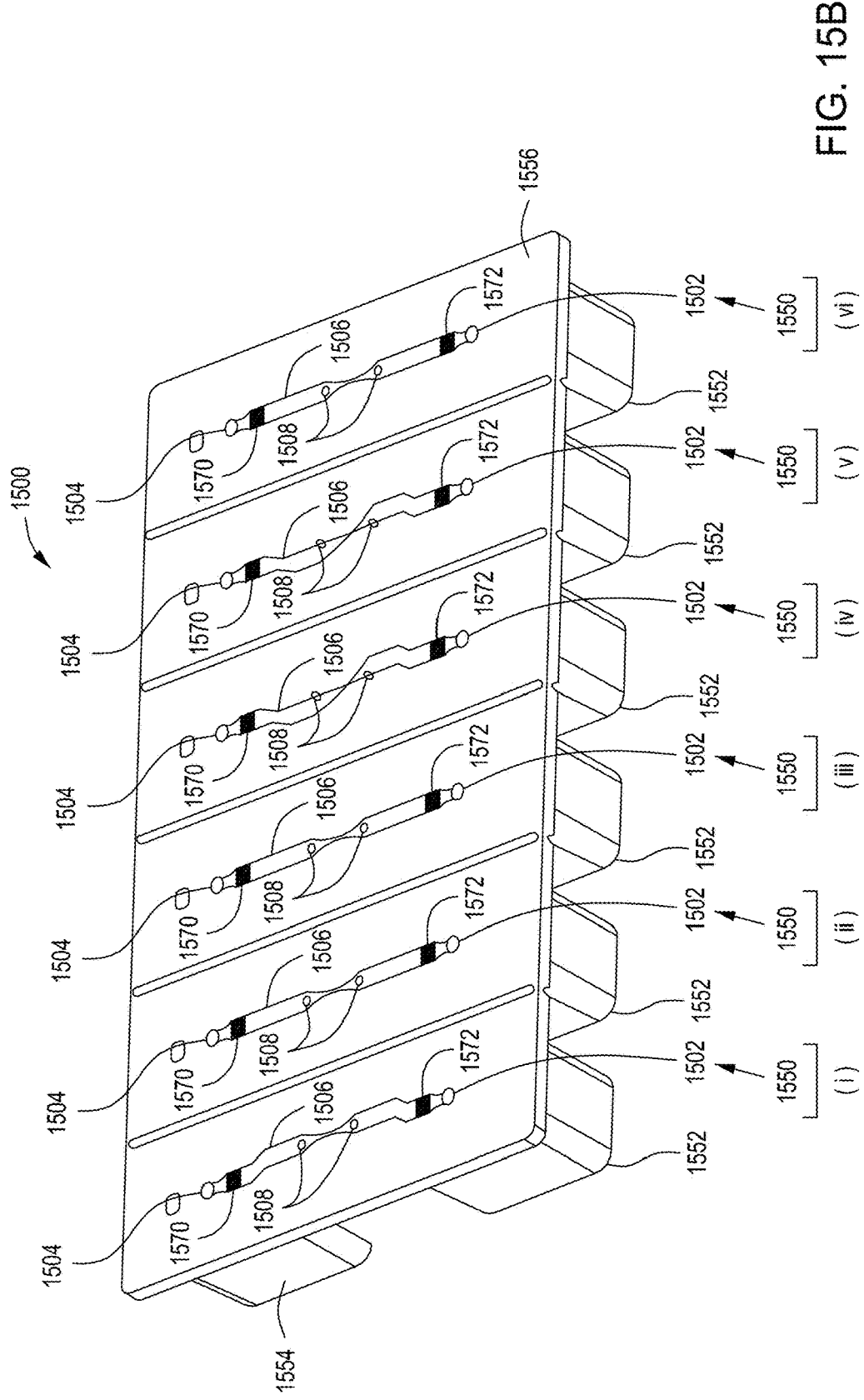
Figure 15C:
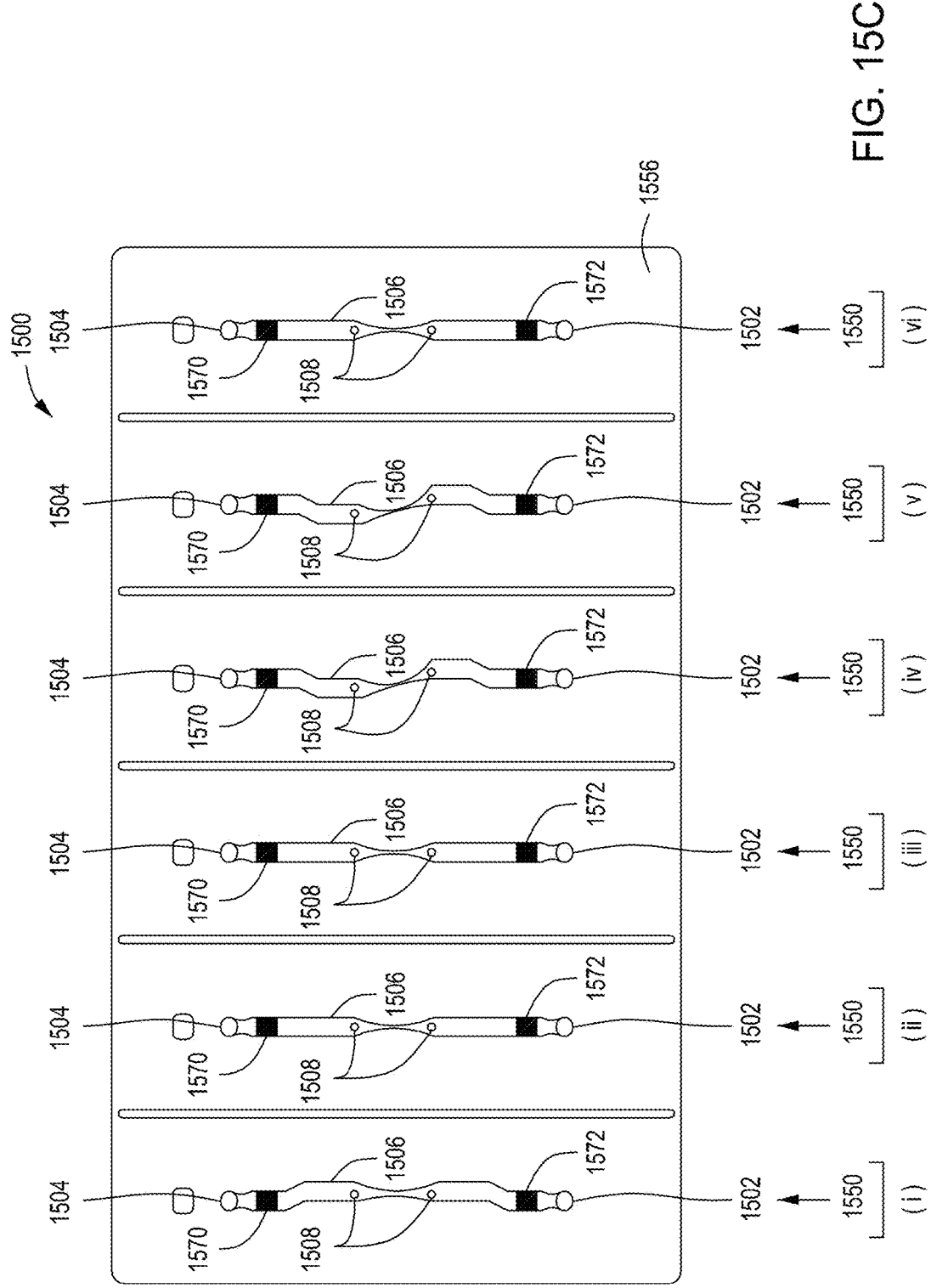
Figure 16A:
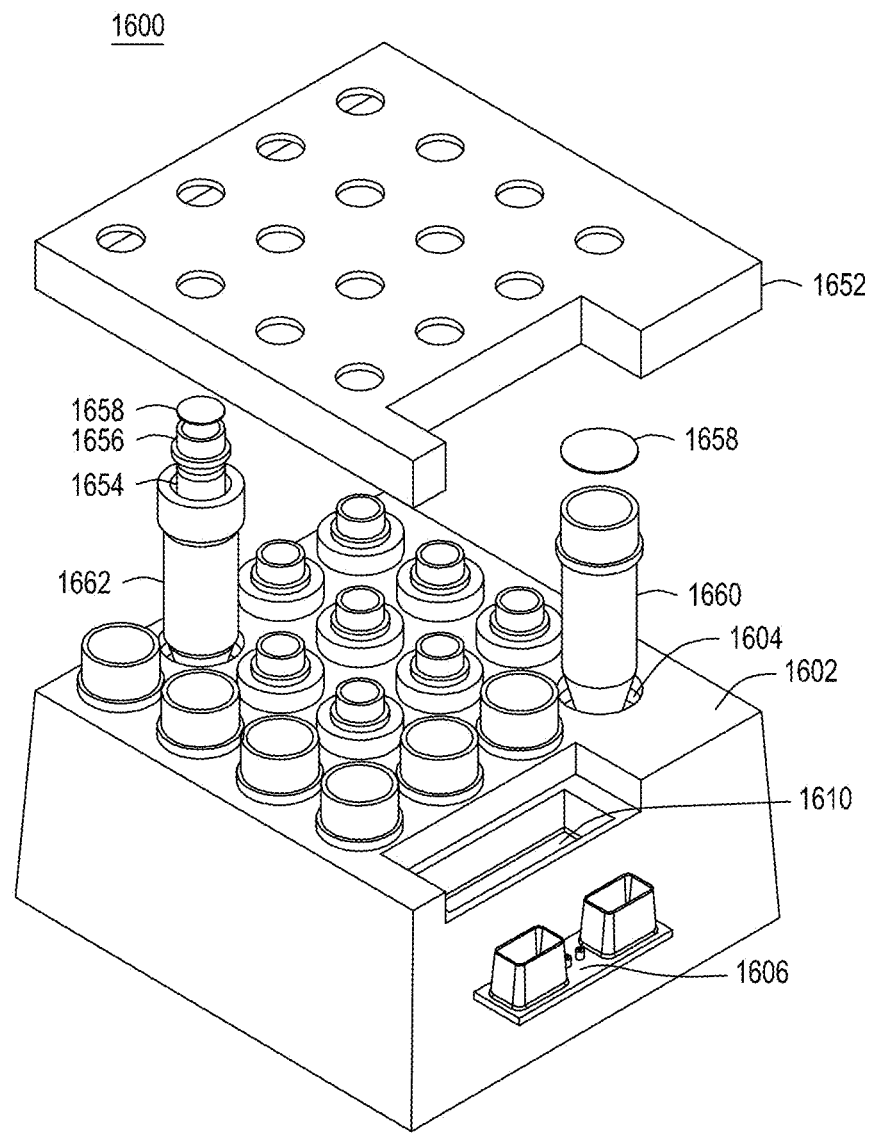
FIGS. 16A and 16B depict alternative embodiments of a combination reagent cartridge and electroporation device.
Figure 16B:
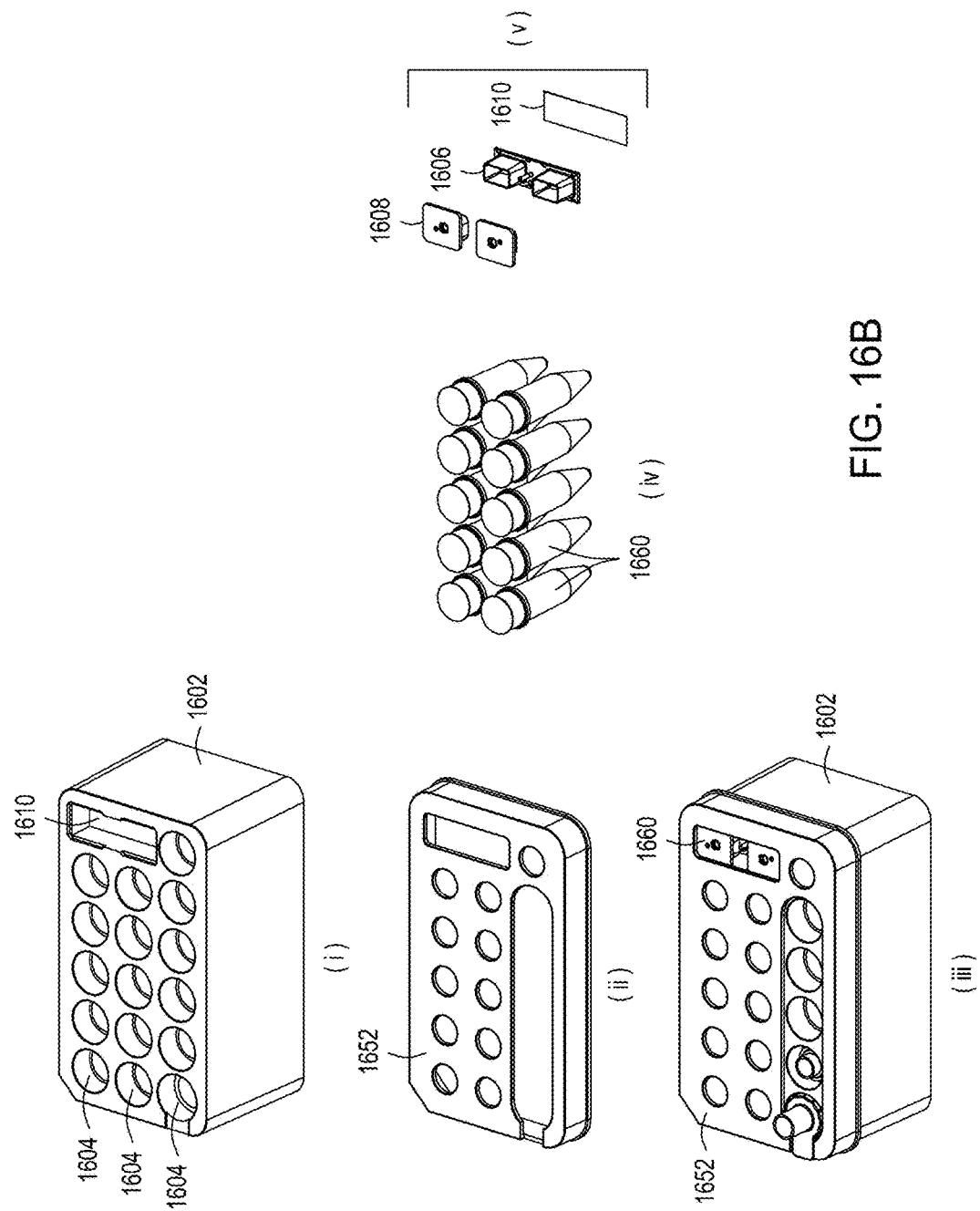

FIGS. 15A through 15C are top perspective, bottom perspective, and bottom views, respectively, of six co-joined FTEP devices 1550 that may be part of, e.g., reagent cartridge 1600 in FIGS. 16A and 16B infra (i.e., serve as FTEP 1606 in reagent cartridge 1600). FIG. 15A depicts six FTEP units 1550 arranged on a single, integrally-formed injection molded cyclic olefin copolymer (COC) substrate 1556. The channels 1506 shown in FIG. 15B are sealed with a COC film having a thickness of 50 microns to 1 mm (not shown). The COC film may be thermally bonded to the base of the assembly 1500 (the surface most prominently displayed in FIG. 15B). In FIGS. 15B and 15C, the co-joined FTEP devices have different channel architectures and electrode placements that may be advantageous in various applications. For instance, the curved channels of devices (i), (iv) and (v) take advantage of inertia to direct the cells in the fluid away from the electrodes. The electrodes may be positioned off center in the channel to further enhance cells flow and reduce the potential for damage to the cells. This may be particularly important for cells or materials that are particularly sensitive to electrolytic effects or local changes in pH proximate the electrodes. The electrodes may be at least partially embedded into the channel walls, as shown in embodiments (iii) and (iv), so as to further reduce these effects.

Each of the six FTEP units 1550 have wells 1552 that define cell sample inlets and wells 1554 that define cell sample outlets. FIG. 15B is a bottom perspective view of the six co-joined FTEP devices 1550 of FIG. 15A also depicting six FTEP units 1550 arranged on a single substrate 1556. Six inlet wells 1552 can be seen, one for each flow-through electroporation unit 1550, and one outlet well 1554 can be seen. Also seen in FIG. 15B for each FTEP unit 1550 are an inlet 1502, an outlet 1504, a flow channel 1506, and two electrodes 1508 on either end of a narrowed region in flow channel 1506. Filters 1570 and 1572 are included in the channels to prevent clogging of the channel, particularly at narrowed region of the flow channel. FIG. 15C is a bottom view of the six co-joined FTEP devices 1550 of FIGS. 15A and 15B. Depicted in FIG. 15C are six FTEP units 1550 arranged on a single substrate 1556, where each FTEP unit 1550 comprises an inlet 1502, outlet 1504, flow channel 1506 and two electrodes 1508 on either end of a narrowed region in flow channel 1506 in each FTEP unit 1550. Once the six FTEP units 1550 are fabricated, they can be separated from one another (e.g., "snapped apart") upon the depicted score lines and used one at a time as seen in the cartridge depicted in FIG. 16A or 16B; alternatively, the FTEP units may be used in embodiments where two or more FTEP units 1550 are used in parallel.

Figure 15D:
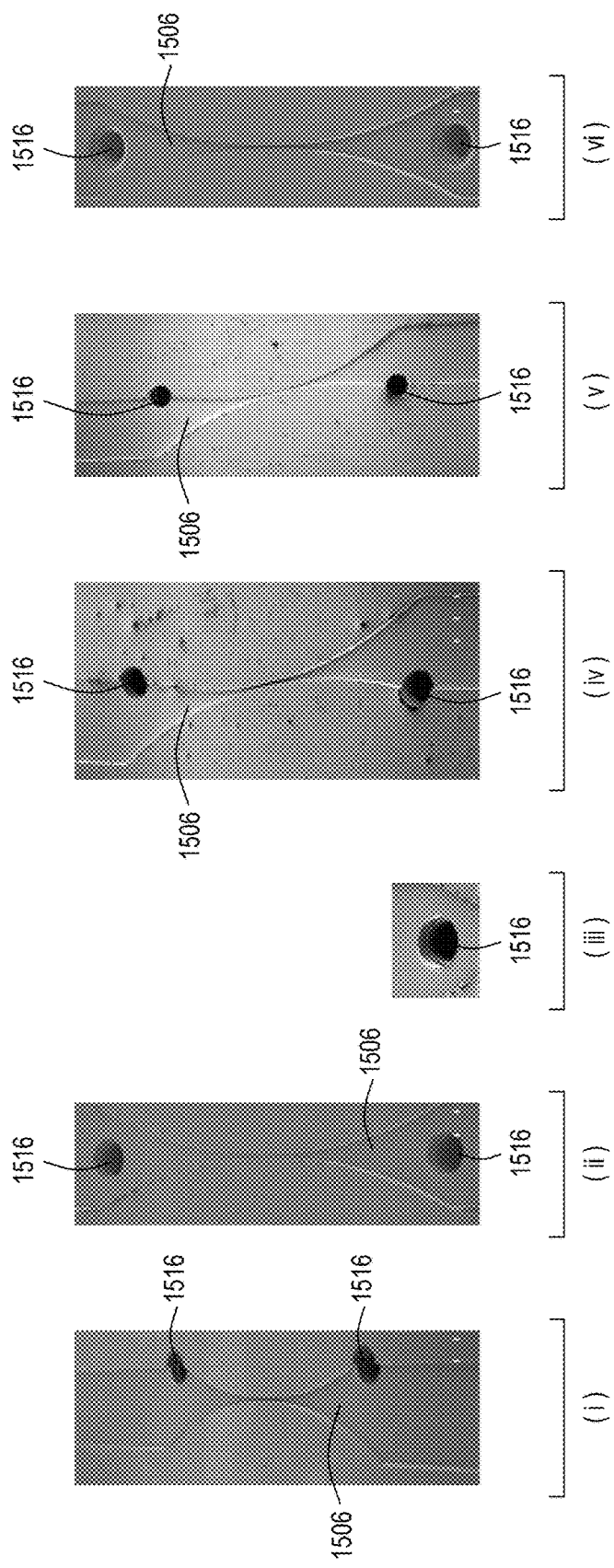
FIG. 15D shows scanning electromicrographs of the FTEP units depicted in FIG. 15C.

FIG. 15D shows scanning electromicrographs of the FTEP units depicted in FIG. 15C with the units (i), (ii), (iii), (iv), (v), and (vi) in FIG. 15D corresponding to units (i), (ii), (iii), (iv), (v), and (vi) in FIG. 15C. In FIG. 15D, for each unit both the electrode channels 1516 as well as the flow channel 1506 can be seen. The scale is 1 mm per hash mark as shown in the lower right-hand corner of each micrograph. It can be seen that in this embodiment the inlet apertures have a rounded edge, the advantages of which include resistance to air trapping, promotion of laminar flow, and reduction of risk of cell damage. The rounded edges may have a radius of curvature of about 10, 20, 30, 40, 50, 60, 70, 80, 90, 100, 150, 200 or 250 microns.

Figure 15E:
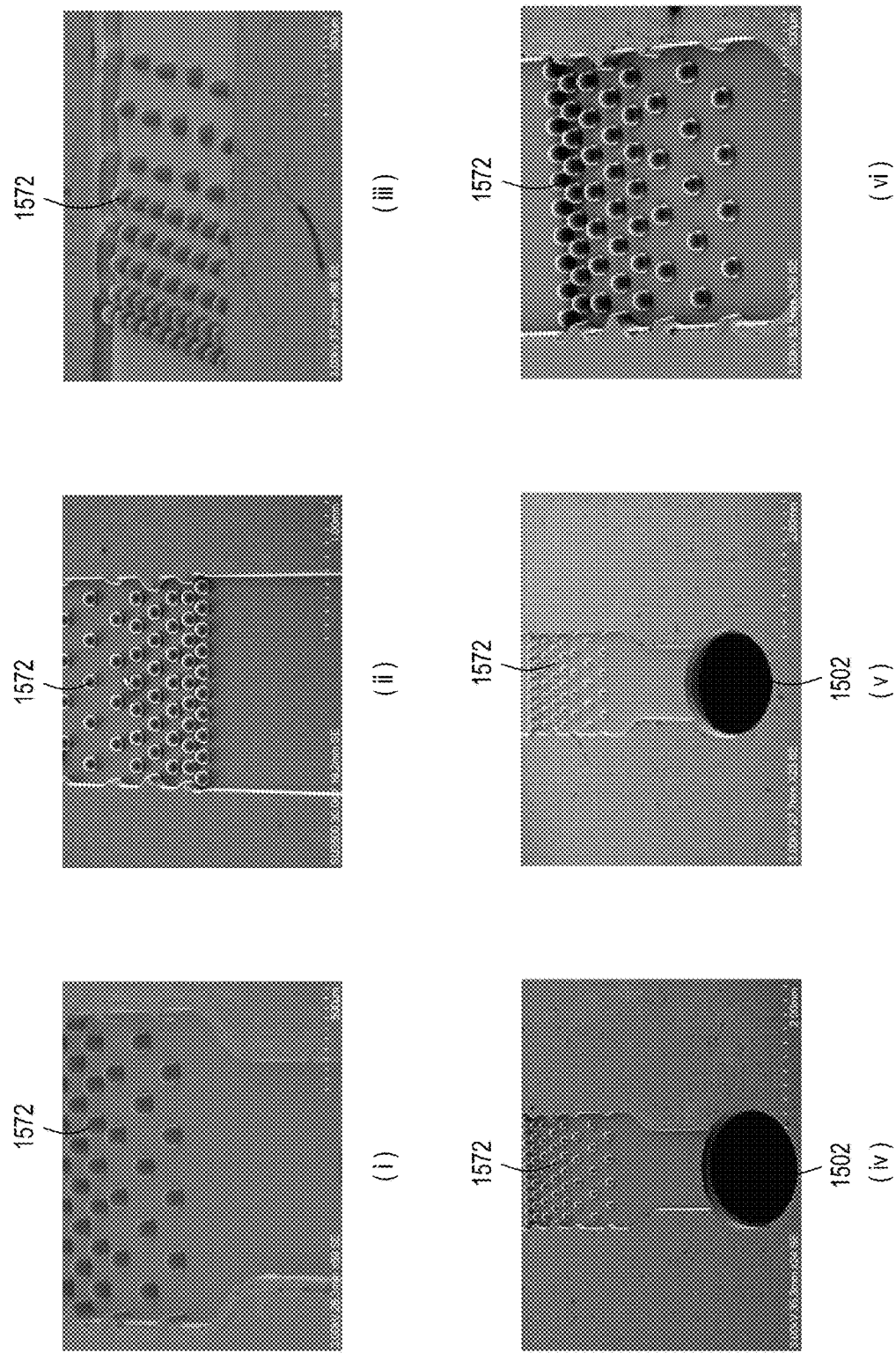
FIG. 15E shows scanning electromicrographs of filters 1570 and 1572 depicted as black bars in FIGS. 15B and 15C.

FIG. 15E shows scanning electromicrographs of the filters 1570 and 1572 depicted as black bars in FIGS. 15B and 15C. Note in this embodiment, the porosity of the filter 1572 varies from large pores (near the inlet 1502) to small pores toward the flow channel (not shown). In this embodiment, the channel optionally but not necessarily narrows. If a second filter is present, the second filter may also vary in porosity. In the case of a second filter between the second electrode and the outlet channel, the filter can vary from large pores (near the second electrode) to small pores toward the outlet channel. Scale information is shown in each micrograph.

In certain embodiments, the filter serves the purpose of filtering the fluid containing the cells and DNA before the fluid encounters the narrowed portion of the flow channel. The filter thus decreases the likelihood that cells or other matter do not clog the narrowed portion of the flow channel. Instead, if there is particulate matter that poses a threat to clogging the narrowed portion of the flow channel, the filter will catch the particulate matter leaving other pores through which the rest of the cell/DNA/fluid can move. The depicted construction (integral molding with the channel wall) is particularly advantageous because it reduces cost and complexity of the device while also reducing the risk that pieces of the filter itself may dislodge and clog the channel or otherwise interfere with device operation. Note that in this embodiment, the filter has a gradient pore size (from large pores proximate the inlet to smaller pores proximal the narrowed portion of the flow channel); however, in alternative embodiments the pores may be the same size or not gradient in size.

Further, in yet other embodiments, the flow channel may not narrow. In these specific embodiments, the pores themselves can serve to provide such a narrowing function for enhancing electroporation, and the flow channel walls do not constrict or constrict minimally as the fluid flows through the channel. These embodiments can allow control of the rate of flow of cells through the device to optimize introduction of exogenous material into various cell types.

Moreover, though the scanning electromicrographs in FIG. 15E shown the filter elements as rounded "pegs", it should be understood that the filter elements may be triangular-, square-, rectangular-, pentagonal-, hexagonal-, oval-, elliptical- or other faceted-shaped pegs.

Figure 15F:
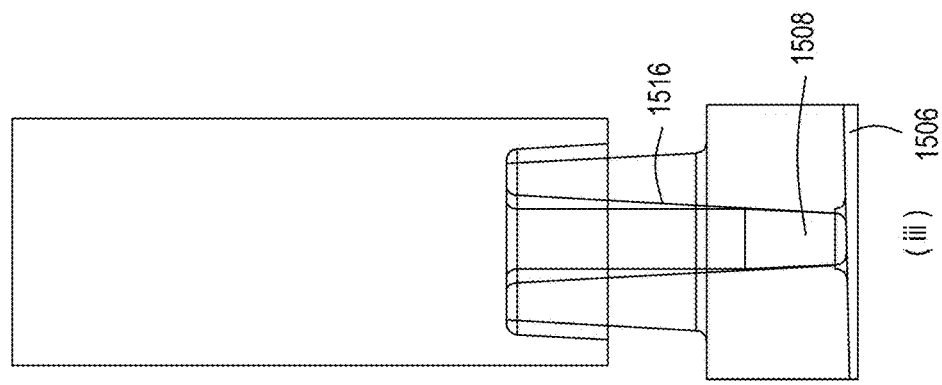
FIG. 15F depicts (i) the electrodes before insertion into the FTEP device; (ii) an electrode; and (iii) the electrode inserted into an electrode channel with the electrode and electrode channel adjacent to the flow channel.
Figure 15F:
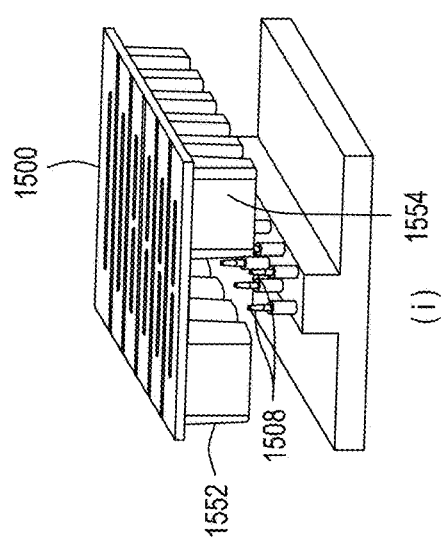

FIG. 15F depicts (i) the electrodes 1508 before insertion into the FTEP device 1500 (here, a six-unit FTEP device) having inlet reservoirs 1552 and outlet reservoirs 1554. In the preferred embodiment, the device 1500 is used in an orientation inverted relative to that shown in FIG. 15F (i). FIG. 15F (ii) depicts an electrode 1508 contained within and projecting from a sheath. FIG. 15F (iii) depicts the electrode 1508 inserted into an electrode channel 1516 with the electrode channel 1516 (and electrode 15080 adjacent to the flow channel 1506. In the embodiment shown in FIG. 15F (iii), the electrode is even with the walls of the flow channel; that is, the electrode is not in the path of the cells/DNA/fluid flowing through flow channel 1506, however, neither is the electrode recessed within the electrode channel 1516. Indeed, the electrode 1508 may be recessed within the electrode channel 1516, may be extend to the end of electrode channel 1516 and thus be even with the walls of flow channel 1506, or electrode 1508 may extend a minimal distance into flow channel 1506 so long as the electrode does not impede movement of the cells through the flow channel. The rounded or beveled edges of the aperture in the flow channel 1506 help prevent trapping air and reduce discontinuities in the electric field.

Figure 15G:
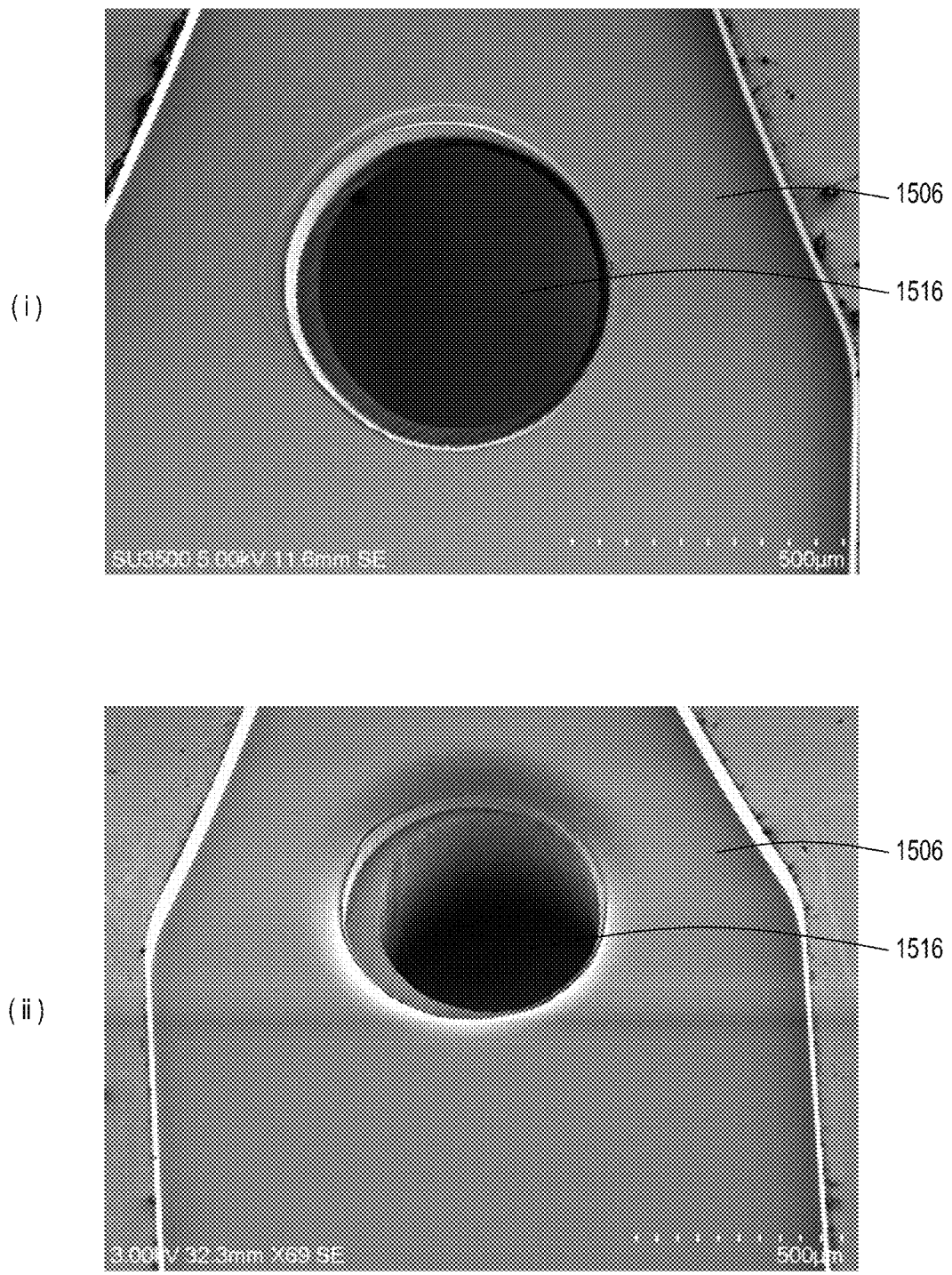
FIG. 15G shows two scanning electromicrographs of two different configurations of the aperture where the electrode channel meets the flow channel.

FIG. 15G presents two scanning electromicrographs of two different configurations of the aperture where electrode channel 1516 meets flow channel 1506. In FIG. 15G (i) (top), the edge of the junction of electrode channel 1516 and flow channel 1506 comprises a sharp edge. In contrast, in FIG. 15G (ii) (bottom), the edges of the junction of electrode channel 1516 and flow channel 1506 comprises a rounded edge. Both configurations were tested (data not shown), and it was found that the rounded-edge configuration decreases the likelihood that air will become trapped between flow channel 1506 and the electrode (not seen in this Figure) in electrode channel 1516. Indeed, the electrodes of the FTEP devices should be "wet"; that is, immersed in the fluid/cells/DNA.

Automated Multi-Module Cell Processing System(s) Comprising the FTEPs

FIG. 16A depicts an exemplary combination reagent cartridge and FTEP device 1600 ("cartridge") that may be used in an automated multi-module cell processing system. Cartridge 1600 comprises a body 1602, and reagent receptacles or reservoirs 1604. Additionally, cartridge 1600 comprises an FTEP device 1606, aspects of which are described in relation to FIGS. 1-6 and 8-15 (e.g., in this embodiment of the cartridge, there is a single FTEP device). Cartridge 1600 may be disposable or cartridge 1600 may be configured to be reused. Preferably, cartridge 1600 is disposable. Cartridge 1600 may be made from a variety of suitable materials, including stainless steel, aluminum, or plastics including polyvinyl chloride, polyethylene, polyamide, polyethylene, polypropylene, acrylonitrile butadiene, polycarbonate, polyetheretheketone (PEEK), poly(methyl methylacrylate) (PMMA), polysulfone, and polyurethane, and co-polymers of these and other polymers. If the cartridge is disposable, preferably it is made of plastic. Preferably the material used to fabricate the cartridge is thermally-conductive, as in certain embodiments the cartridge 1600 contacts a thermal device (not shown) that heats or cools reagents in the reagent receptacles or reservoirs 1604. In some embodiments, the thermal device is a Peltier device or thermoelectric cooler. Reagent receptacles or reservoirs 1604 may be receptacles into which individual tubes of reagents are inserted as shown in FIG. 16A, receptacles into which one or more multiple co-joined tubes are inserted (e.g., rows of five tubes that are co-joined are inserted into the reagent receptacles as seen in FIG. 16B (iv)), or the reagent receptacles may hold the reagents without inserted tubes. Additionally, the receptacles in a reagent cartridge may be configured for any combination of tubes, co-joined tubes, and direct-fill of reagents.

In one embodiment, the reagent receptacles or reservoirs 1604 of reagent cartridge 1600 are configured to hold various size tubes, including, e.g., 250 ml tubes, 25 ml tubes, 10 ml tubes, 5 ml tubes, and Eppendorf or microcentrifuge tubes. In yet another embodiment, all receptacles may be configured to hold the same size tube, e.g., 5 ml tubes, and reservoir inserts may be used to accommodate smaller tubes in the reagent reservoir. In yet another embodiment—particularly in an embodiment where the reagent cartridge is disposable—the reagent reservoirs hold reagents without inserted tubes. In this disposable embodiment, the reagent cartridge may be part of a kit, where the reagent cartridge is pre-filled with reagents and the receptacles or reservoirs sealed with, e.g., foil, heat seal acrylic or the like and presented to a consumer where the reagent cartridge can then be used in an automated multi-module cell processing system. The reagents contained in the reagent cartridge will vary depending on work flow; that is, the reagents will vary depending on the processes to which the cells are subjected in the automated multi-module cell processing system.

Further, FIG. 16A shows additional detail for an embodiment of a reagent cartridge and FTEP device where reagent receptacles or reservoirs 1604 are configured to accept tubes 1660 or thermal spacers 1662. In addition, within thermal spacer 1662 is a small tube 1654, such as an Eppendorf or microcentrifuge tube, useful when only small reagent volumes are required. Thermal spacer 1662 is thermally conductive assuring heat or cooling is transferred to reagents contained in small tubes, e.g., Eppendorf tubes 1654. As discussed above, in some embodiments the body of the reagent cartridge itself is thermally conductive and is in contact with a thermal device to warm or cool the reagents contain therein as desired by a user. Also seen in FIG. 16A are foil seals 1658 used to seal tubes 1660 and 1654. Alternatively, if the reagent cartridge is reusable, the reagent cartridge may comprise a thermal device to heat and cool reagents contained within, as opposed to contacting a thermal device.

In certain embodiments of reagent cartridge 1600 shown in FIG. 16A, the reagent cartridge comprises an optically readable code (e.g., barcode or Aztec code) or instructions/data stored in an onboard memory element (not shown) readable by complementary sensor of the automated system (see applications incorporated by reference) and transmitted to a processor of the automated system. The code, data, instructions, or script provide (or enable the retrieval of) instructions for dispensing by the automated system the reagents and controlling the electroporation device contained within reagent cartridge 1600. Also, the reagent cartridge 1600 as one component in an automated multi-module cell processing system may include a code, instructions or scripts specifying two, three, four, five, ten or more processes performed by the automated multi-module cell processing system, or even specify all processes performed by the automated multi-module cell processing system. In certain embodiments, the reagent cartridge is disposable and is pre-packaged with reagents tailored to performing specific cell processing protocols, e.g., genome editing or protein production. Because the reagent cartridge contents vary while components of the automated multi-module cell processing system may not, the script associated with a particular reagent cartridge matches the reagents used and cell processes performed. Thus, e.g., reagent cartridges may be pre-packaged with reagents for genome editing and a script that specifies the process steps for performing genome editing in an automated multi-module cell processing system.

FIG. 16B depicts an alternative embodiment of a combination reagent cartridge and electroporation device. At 16B (i), a body 1602 of a reagent cartridge is shown, as are reagent receptacles or reservoirs 1604, that may be configured to hold various size tubes, including, e.g., 250 ml tubes, 25 ml tubes, 10 ml tubes, 5 ml tubes, and Eppendorf or microcentrifuge tubes. Additionally, there is a recess 1610 into which an FTEP device (not shown) may be placed. FIG. 16B (ii) depicts a cover 1652 for the body 1602 of the reagent cartridge. FIG. 16B (iii) depicts the body 1602 and cover 1652 of the FTEP device assembled, with an assembled FTEP device 1660 placed within recess 1610 (seen in (i)). FIG. 16B (iv) shows co-joined tubes that may be placed within reagent receptacles or reservoirs 1604. FIG. 16B (v) is an exploded view of the FTEP cartridge 1606, covers 1608 with seals or gaskets (not shown) that mate with the inlet and outlet reservoirs, and film 1610, which is used to seal the bottom of the FTEP device. The covers and seals form an air-tight seal permitting the application of pneumatic pressure sufficient to drive the fluids in the FTEP device in the manner described above. Element 1610 corresponds to the COC film described above in connection with FIG. 15 which seals the channels in the underside of the cartridge 1606 and serves as the base or bottom of the FTEP device 1600.

Figure 17:
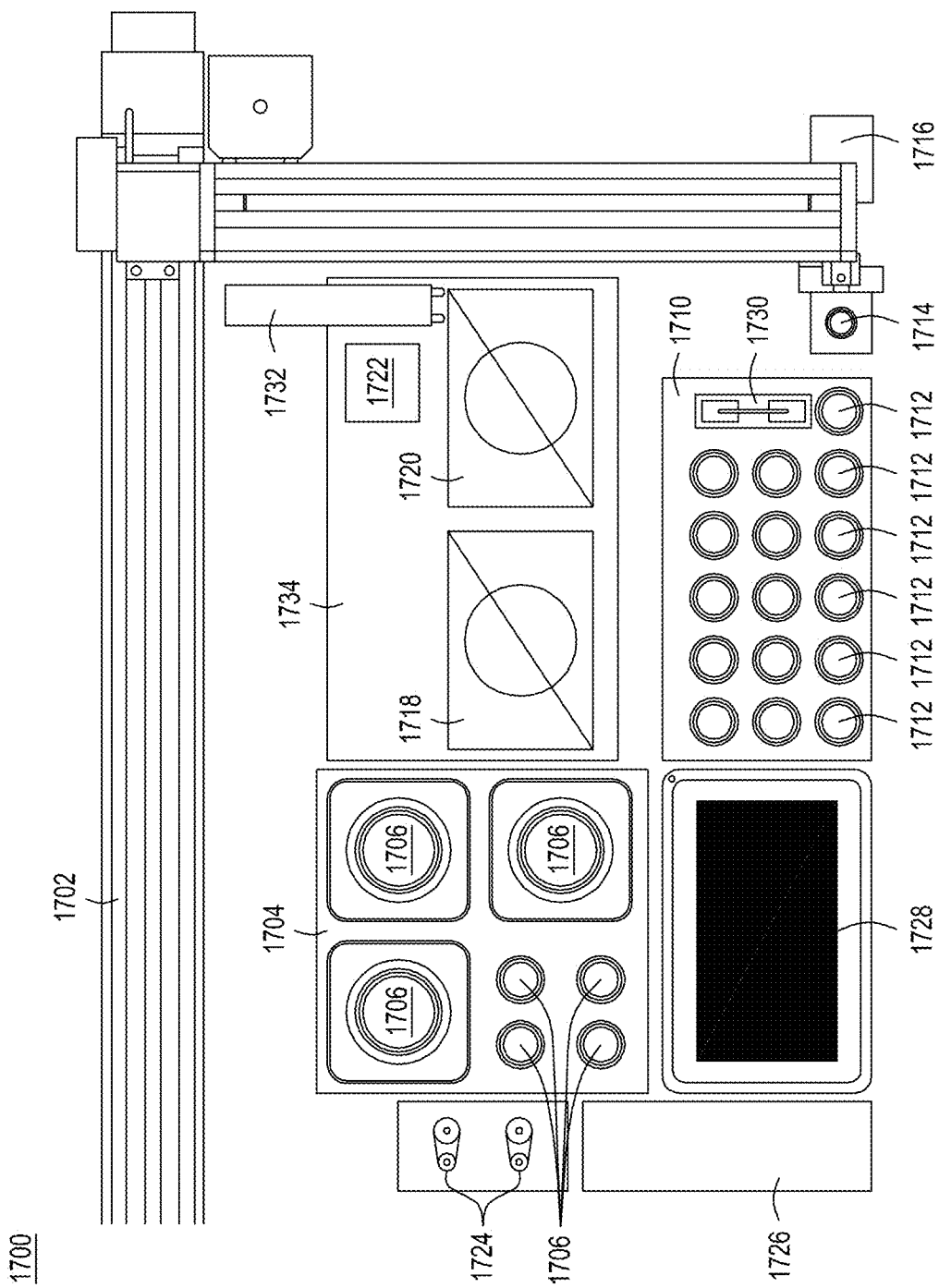
FIG. 17 depicts an exemplary automated multi-module cell processing system comprising an FTEP device and additional optional modules.

FIG. 17 depicts an exemplary automated multi-module cell processing instrument 1700 comprising an exemplary FTEP device 1730 as part of a reagent cartridge 1710 to, e.g., perform one of the exemplary workflows described below, as well as additional exemplary workflows. Illustrated is a gantry 1702, providing an automated mechanical motion system (actuator) (not shown) that supplies XYZ axis motion control to, e.g., modules of the automated multi-module cell processing instrument 1700, including, e.g., an air displacement pipette 1732. In some automated multi-module cell processing instruments, the air displacement pipettor is moved by a gantry and the various modules and reagent cartridges remain stationary; however, in other embodiments, the pipetting system may stay stationary while the various modules are moved. Also included in the automated multi-module cell processing instrument 1700 is wash or reagent cartridge 1704, comprising reservoirs 1706. Wash or reagent cartridge 1704 may be configured to accommodate large tubes, for example, wash solutions, or solutions that are used often throughout an iterative process. In one example, wash or reagent cartridge 1704 may be configured to remain in place when two or more reagent cartridges 1710 are sequentially used and replaced. Although reagent cartridge 1710 and wash or reagent cartridge 1704 are shown in FIG. 17 as separate cartridges, the contents of wash cartridge 304 may be incorporated into reagent cartridge 1710.

The exemplary automated multi-module cell processing instrument 1700 of FIG. 17 further comprises a cell growth module 1734. In the embodiment illustrated in FIG. 17, the cell growth module 1734 comprises two cell growth units 1718, 1720 as well as a cell concentration module 1722. In alternative embodiments, the cell concentration module 1722 may be separate from cell growth module 1734, e.g., in a separate, dedicated module. Also illustrated as part of the automated multi-module cell processing instrument 1700 of FIG. 17 is screening/selection module 1728, served by, e.g., air displacement pipettor 1732, and filtration module 1724. Also seen are a waste repository 1726, and a nucleic acid assembly/desalting module 1714 comprising a reaction chamber or tube receptacle (not shown) and further comprising a magnet 1716 to allow for purification of nucleic acids using, e.g., magnetic solid phase reversible immobilization (SPRI) beads (Applied Biological Materials Inc., Richmond, BC). The reagent cartridge, transformation module, and cell growth module are described in greater detail below.

Figure 18:
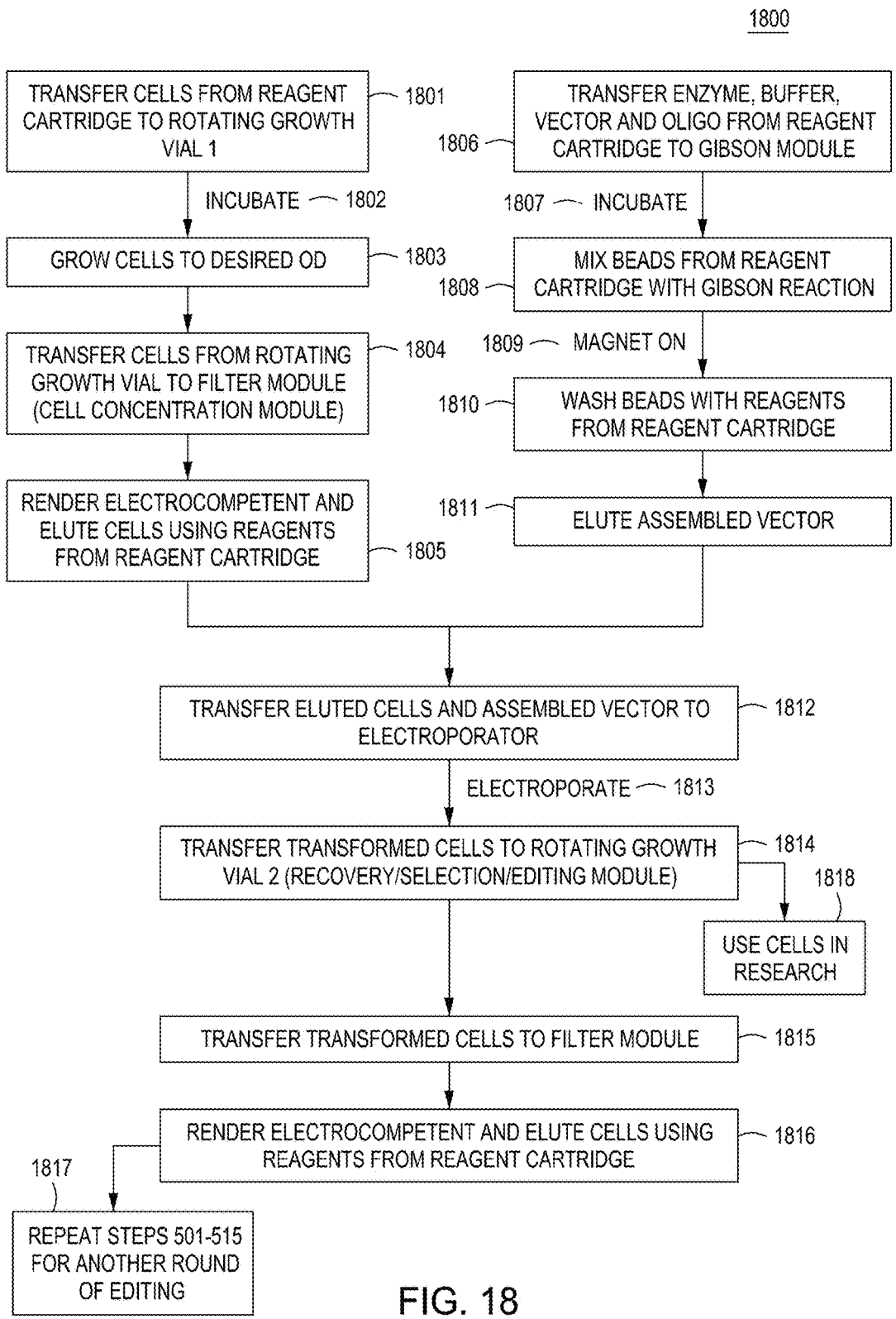
FIG. 18 is a block diagram of an embodiment of a method for using an automated multi-module cell processing system comprising an FTEP in a transformation module.

FIG. 18 is a block diagram of one embodiment of a method 1800 for using the automated multi-module cell processing system depicted in FIG. 17. In a first step, cells are transferred 1801 from reagent cartridge 1810 to growth vial 1818. The cells are incubated 1802, e.g., until they grow to a desired OD 1803. The cells are then transferred 1804 to filtration module 1822 to render the cells electrocompetent and to reduce the volume of the cell sample to a volume appropriate for electroporation, as well as to remove unwanted components, e.g., salts, from the cell sample. Once the cells have been rendered electrocompetent and suspended in an appropriate volume for transformation, the cell sample is transferred 1812 to FTEP device 1830 in reagent cartridge 1810.

While cells are being processed for electroporation, automated multi-module cell processing system may be preparing the nucleic acids to be electroporated into the cells. As a first step, a nucleic acid sample comprising vectors, a nucleic acid sample comprising oligonucleotides, and enzymes and other reaction components are transferred 1806 from reagent reservoirs of the reagent cartridge to a disposable tube in the nucleic acid assembly module, and the nucleic acid assembly mix (vectors+oligos+enzymes+reagents) is incubated 1807. Once sufficient time has elapsed for the nucleic acid assembly reaction to take place, the nucleic acid assembly mix is combined with magnetic beads 1808. The mix is incubated for sufficient time for the assembled vector and oligonucleotides to bind to the magnetic beads. The magnet is engaged 1809 so that the assembled vector and oligonucleotides can be washed 1810 and eluted 1811. Once the assembled vector has been eluted 1811, the assembled vector is transferred 1812 to the FTEP device in the reagent cartridge. The assembled vector and the cells are thus combined in an FTEP device and the FTEP device is engaged 1813.

After electroporation, the transformed cells optionally are transferred 1814 to a second growth vial to, e.g., recover from the transformation process, be submitted to selection, or for, in this particular example, genome editing. Once the transformed cells have recovered, been selected (e.g., by an antibiotic or other reagent added from the reagent cartridge or by, e.g., temperature), or genome editing has taken place, the cells may be removed from the instrument and used in further research 1818, or aspirated 1815 by the filtration module to be washed to remove dead cells and/or concentrated, rendered electrocompetent, and eluted 1816 using a wash solution dispensed through the filter from reagent reservoir in wash or reagent cartridge. The eluted cells may then be collected in an empty vessel in the wash cartridge. The air displacement pipettor may transfer media from the reagent cartridge to the eluted cells. All or some of steps 1801-1816 may be repeated for recursive rounds of genome editing 1817; alternatively, the transformed cells may be used in research 1818.

Figure 19:
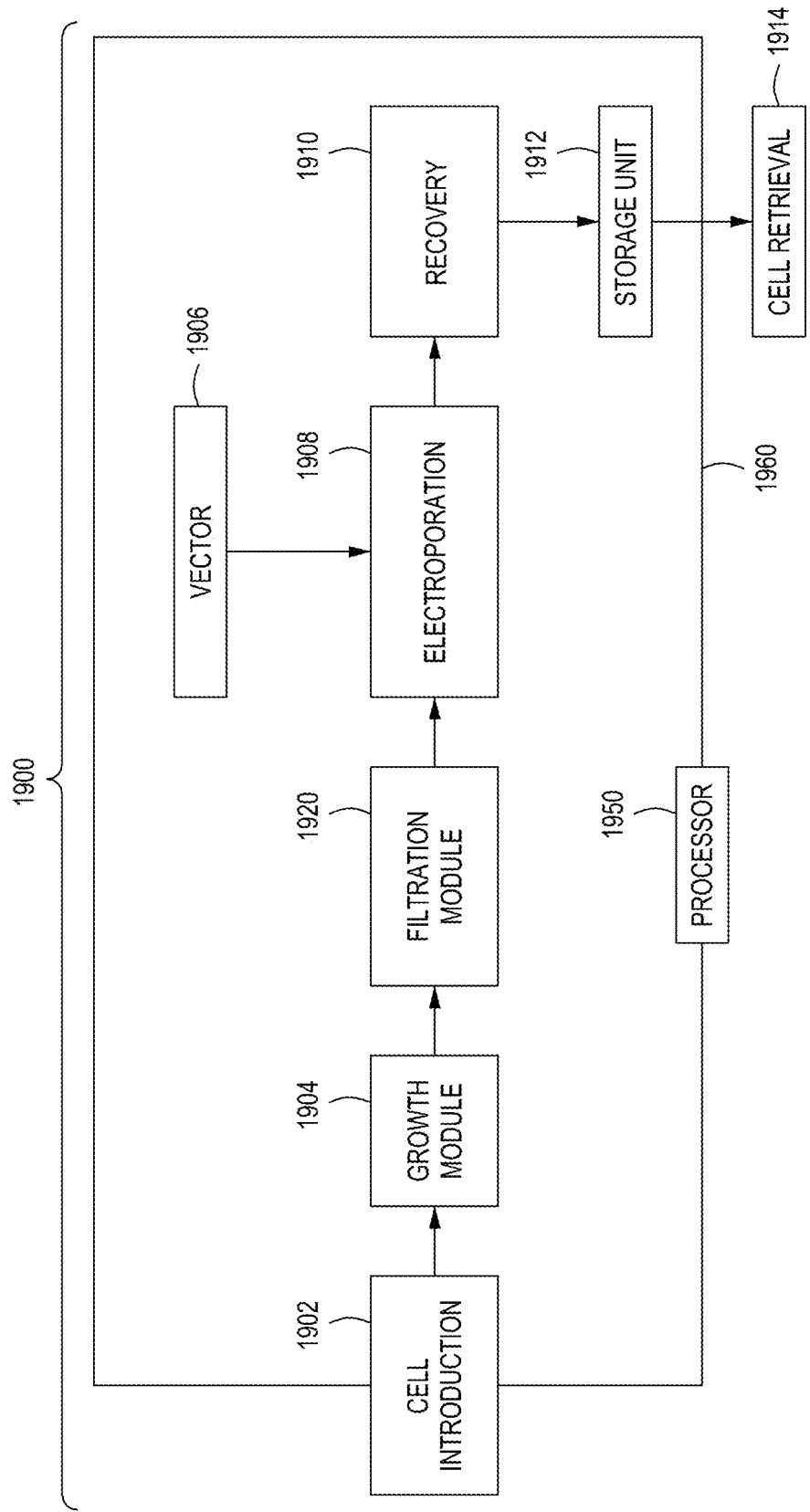
FIG. 19 is a simplified block diagram of an exemplary automated multi-module cell processing system in which one or more of the FTEP devices described herein may be used.

Use of the Reagent Cartridge(s) in Exemplary Automated Multi-Module Cell Processing Systems As described above, the FTEP devices may be used in stand-alone devices or used as a module in an automated multi-module processing system. A general exemplary embodiment of a multi-module cell processing system is shown in FIG. 19. In some embodiments, the cell processing system 1900 may include a housing 1960, a receptacle for introducing cells to be transformed or transfected 1902, and a growth module (a cell growth device) 1904. The cells to be transformed are transferred from a reagent cartridge to the growth module to be cultured until the cells hit a target OD. Once the cells hit the target OD, the growth module may cool or freeze the cells for later processing or transfer the cells to a filtration module 1920 where the cells are rendered electrocompetent and concentrated. The filtration module 1920 comprises e.g., a filter to treat the cells to make them electrocompetent and concentrate the electrocompetent cells. In one example, 20 ml of cells+growth media is concentrated to 400 µl cells in 10% glycerol. Once the electrocompetent cells have been concentrated, the cells are transferred to an electroporation device in the reagent cartridge to be transformed with a desired nucleic acid. In addition to the receptacle for receiving cells, the multi-module cell processing system includes a receptacle located in the reagent cartridge for storing the nucleic acids to be electroporated into the cells 1906. The nucleic acids are transferred to the electroporation device 1908 which already contains the concentrated electrocompetent cells grown to the specified OD, where the nucleic acids are introduced into the cells. Following electroporation, the transformed cells are transferred into, e.g., a recovery module 1910. Here, the cells are given the opportunity to recover from the electroporation procedure.

In some embodiments, after recovery the cells are transferred to a storage module 1912 to be stored at, e.g., 4° C. or frozen. The cells can then be retrieved from a retrieval module 1914 and used for further studies off-line. The automated multi-module cell processing system is controlled by a processor 1950 configured to operate the instrument based on user input or one or more scripts, where one or more may be associated with a reagent cartridge. The processor 1950 may control the timing, duration, temperature, and other operations (including, e.g., dispensing reagents) of the various modules of the system 1900 as specified by one or more scripts. In addition to or as an alternative to the one or more scripts, the processor may be programmed with standard protocol parameters from which a user may select; alternatively, a user may select one or all parameters manually. The script may specify, e.g., the wavelength at which OD is read in the cell growth module, the target OD to which the cells are grown, and the target time at which the cells will reach the target OD. The processor may notify the user (e.g., via an application to a smart phone or other device) that the cells have reached the target OD as well as update the user as to the progress of the cells in the cell growth module, electroporation device, filtration module, recovery module, etc. in the automated multi-module cell processing system.

Figure 20:
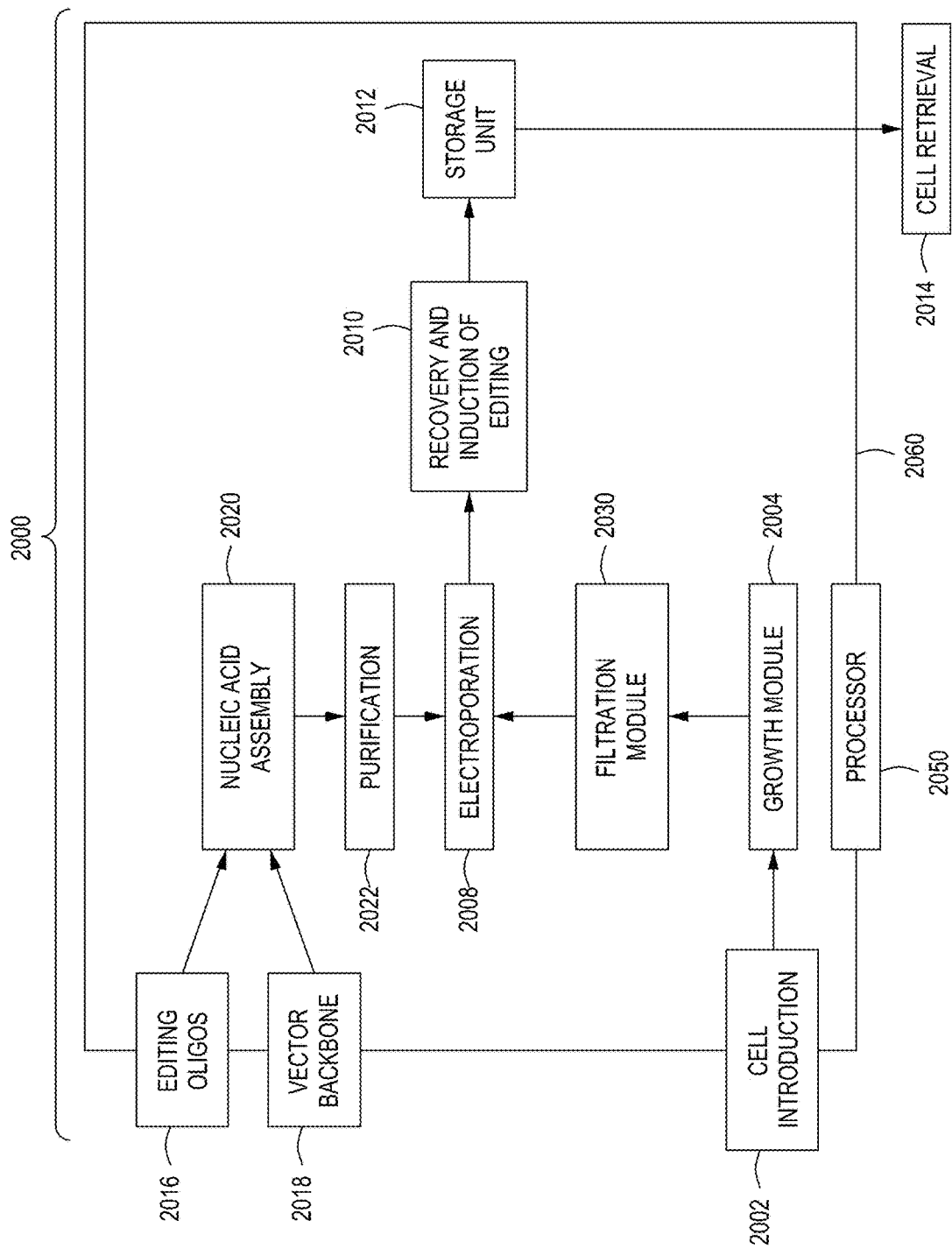
FIG. 20 is a simplified block diagram of a different embodiment of an exemplary automated multi-module cell processing system in which one or more of the FTEP devices described herein may be used.

A second embodiment of an automated multi-module cell processing system is shown in FIG. 20. As with the embodiment shown in FIG. 19, the cell processing system 2000 may include a housing 2060, a reservoir of cells in, e.g., the reagent cartridge, where the cells are to be transformed or transfected 2002, and a growth module (a cell growth device) 2004. The cells to be transformed are transferred from, e.g., a reservoir in the reagent cartridge to the growth module to be cultured until the cells hit a target OD. Once the cells hit the target OD, the growth module may cool or freeze the cells for later processing or transfer the cells to a filtration module 2030 where the cells are rendered electrocompetent and concentrated to a volume optimal for cell transformation as described above in relation to FIG. 19. Once concentrated, the cells are then transferred to the FTEP device 2008 for transformation.

In addition to the reservoir for storing the cells, the reagent cartridge may include a reservoir for storing editing oligonucleotides 2016 and a reservoir for storing an expression vector backbone 2018. Both the editing oligonucleotides and the expression vector backbone are transferred from, e.g., a reagent cartridge to a nucleic acid assembly module 2020 (such as the nucleic acid assembly module described above), where the editing oligonucleotides are inserted into the expression vector backbone. The assembled nucleic acids may be transferred into an optional purification module 2022 for desalting and/or other purification procedures needed to prepare the assembled nucleic acids for transformation. Once the processes carried out by the purification module 2022 are complete, the assembled nucleic acids are also transferred to the FTEP device in reagent cartridge 2008, which already contains the cell culture grown to a target OD, filtered and rendered electrocompetent. In FTEP device 2008, the nucleic acids are introduced into the cells. Following electroporation, the cells are transferred into a combined recovery and editing module 2010. As described above, in some embodiments the automated multi-module cell processing system 2000 is a system that performs gene editing such as an RNA-direct nuclease editing system. For example, see U.S. Ser. No. 16/024,816, filed 30 Jun. 2018; U.S. Ser. No. 16/024,831, filed 30 Jun. 2018; U.S. Ser. No. 62/566,688, filed 2 Oct. 2017; and U.S. Ser. No. 62/567,698, filed 3 Oct. 2017. In the recovery and editing module 2010, the cells are allowed to recover post-transformation, and the cells express the editing oligonucleotides that edit desired genes in the cells as described below.

Following editing, the cells are transferred to a storage module 2012, where the cells can be stored at, e.g., 4° C. until the cells are retrieved for further study. The multi-module cell processing system is controlled by a processor 2050 configured to operate the instrument based on user input, as directed by one or more scripts, or as a combination of user input or a script. The processor 2050 may control the timing, duration, temperature, and operations of the various modules of the system 2000 and the dispensing of reagents from, e.g., a reagent cartridge. The processor may be programmed with standard protocol parameters from which a user may select, a user may specify one or more parameters manually or one or more scripts associated with the reagent cartridge may specify one or more operations and/or reaction parameters. In addition, the processor may notify the user (e.g., via an application to a smart phone or other device) that the cells have reached the target OD as well as update the user as to the progress of the cells in the various modules in the multi-module system.

Certain embodiments of the multi-module processing system such as the system depicted in FIG. 20 include a nucleic acid assembly module (for example, an assembly module that promotes gap repair in yeast and/or a module that performs the Gibson Assembly™ reaction, polymerase chain reaction, ligation chain reaction, ligase detection reaction, ligation, circular polymerase extension cloning, or other assembly or cloning methods) 2020. The nucleic acid assembly module 2020 is configured to assemble the nucleic acids necessary to facilitate genome editing events. In a nuclease-directed genome editing system, a vector comprises one or more regulatory elements operably linked to a polynucleotide sequence encoding a nucleic acid-guided nuclease. Thus, the nucleic acid assembly module 2020 in these embodiments is configured to assemble the expression vector expressing a nucleic acid guided nuclease. The nucleic acid assembly module 2020 may be temperature controlled depending upon the type of nucleic acid assembly used in the instrument. For example, when a nucleic acid assembly protocol is utilized, the module is configured to have the ability to reach and hold 50° C. If PCR is performed as part of the automated multi-module cell processing system, the nucleic acid assembly module is configured to thermocycle between temperatures. The temperatures and duration for maintaining temperatures can be controlled by a preprogrammed set of parameters (as dictated by a script or programmed into the processor), or manually controlled by the user using the processor.

As described above, in one embodiment the automated multi-module cell processing system 2000 is a nuclease-directed genome editing system. Multiple nuclease-based systems exist for providing edits into a cell, and each can be used in either single editing systems as could be performed in the automated system 1900 of FIG. 19; sequential editing systems as could be performed in the automated system 2100 of FIG. 21 described below, e.g., using different nuclease-directed systems sequentially to provide two or more genome edits in a cell; and/or recursive editing systems as could be performed in the automated system 2100 of FIG. 21, e.g. utilizing a single nuclease-directed system to introduce two or more genome edits in a cell simultaneously and sequentially. Automated nuclease-directed processing systems use the nucleases to cleave the cell's genome, to introduce one or more edits into a target region of the cell's genome, or both. Nuclease-directed genome editing mechanisms include zinc-finger editing mechanisms (see Urnov et al., Nature Reviews Genetics, 11:636-64 (2010)), mega-nuclease editing mechanisms (see Epinat et al., Nucleic Acids Research, 31(11):2952-62 (2003); and Arnould et al., Journal of Molecular Biology, 371(1):49-65 (2007)), and RNA-guided editing mechanisms (see Jinek et al., Science, 337:816-21 (2012); and Mali et al, Science, 339:823-26 (2013)). In particular embodiments, the nuclease editing system is an inducible system that allows control of the timing of the editing (see Campbell, Biochem J., 473(17): 2573-2589 (2016); and Dow et al., Nature Biotechnology, 33390-94 (2015)). That is, when the cell or population of cells comprising a nucleic acid-guided nuclease encoding DNA is in the presence of the inducer molecule, expression of the nuclease can occur. The ability to modulate nuclease activity can reduce off-target cleavage and facilitate precise genome engineering.

Figure 21:
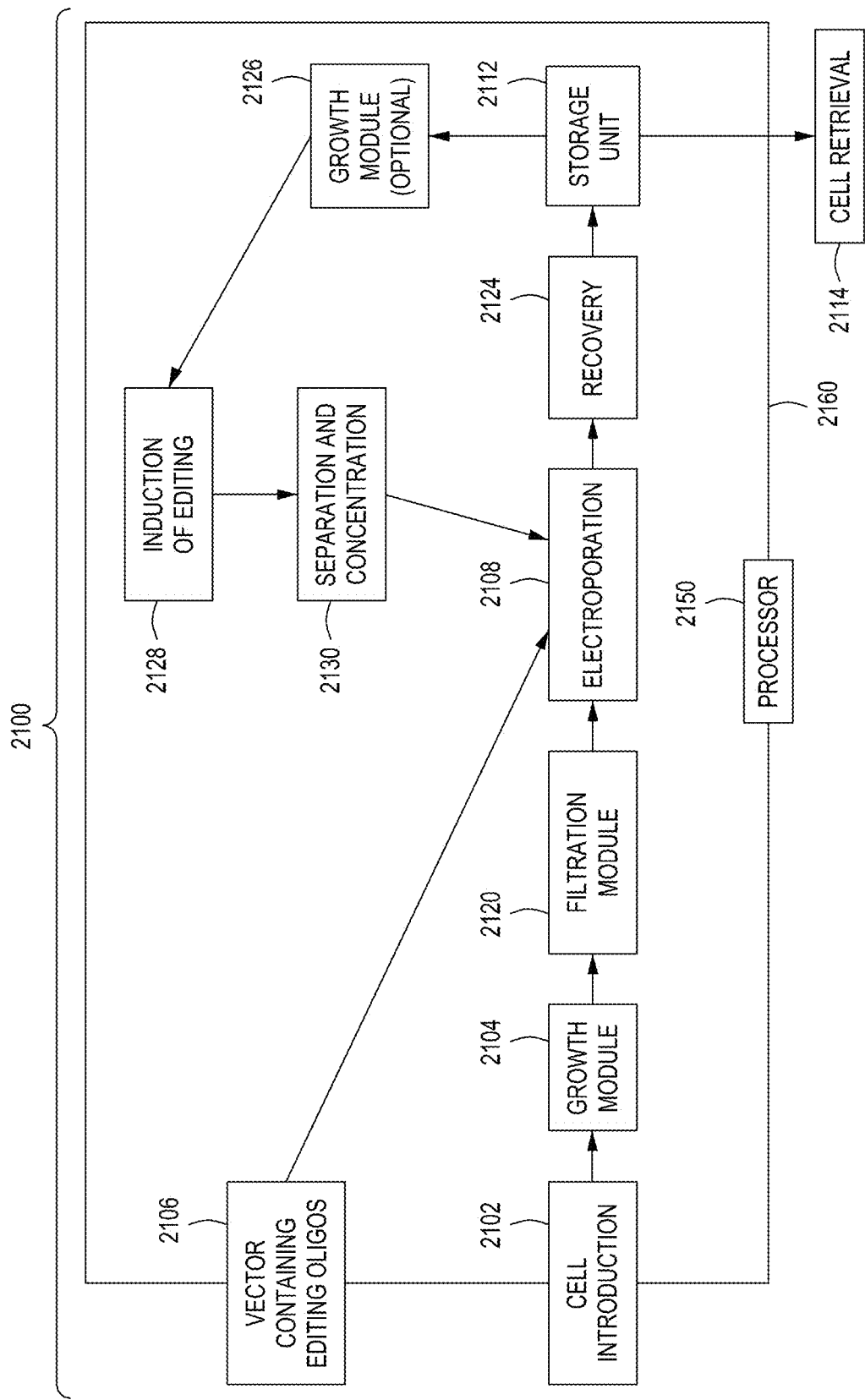
FIG. 21 is a simplified block diagram of yet another embodiment of an exemplary automated multi-module cell processing system in which one or more of the FTEP devices described herein may be used.

A third embodiment of a multi-module cell processing system is shown in FIG. 21. This embodiment depicts an exemplary system that performs recursive gene editing on a cell population. As with the embodiment shown in FIGS. 19 and 20, the cell processing system 2100 may include a housing 2160, a reservoir in, e.g., a reagent cartridge for storing cells to be transformed or transfected 2102, and a cell growth module (a cell growth device) 2104. The cells to be transformed are transferred from a reservoir in the reagent cartridge to the cell growth module to be cultured until the cells hit a target OD. Once the cells hit the target OD, the growth module may cool or freeze the cells for later processing or the growth module may transfer the cells to a filtration module 2120 where the cells are rendered electrocompetent, and the volume of the cells may be reduced substantially. Once the cells have been concentrated to an appropriate volume, the cells are transferred to FTEP device 2108 in the reagent cartridge. In addition to the reservoir for storing cells, the multi-module cell processing system includes a reservoir for storing the vector comprising editing oligonucleotides 2106 (that is, in this embodiment, the automated multi-module cell processing system does not comprise a nucleic acid assembly module; instead, the nucleic acids are provided pre-assembled). The assembled nucleic acids are transferred to the FTEP device 2108, which already contains the cell culture grown to a target OD. In the FTEP device 2108, the nucleic acids are electroporated into the cells. Following electroporation, the cells are transferred into a recovery module 2124. In the recovery module 2124, the transformed cells are allowed to recover post-transformation.

The cells are transferred to a storage module 2112, where the cells can be stored at, e.g., 4° C. until the cells are retrieved for further study, or the cells may be transferred to a second, optional, growth module 2126. Once the cells hit a target OD, the second growth module may cool or freeze the cells for later processing, or transfer the cells to, e.g., an editing module 2128 where, e.g., one or both of an inducible nuclease and an inducible guide nucleic acid is activated in the cells, e.g., by introduction of heat or the introduction of an inducer molecule for expression of the nuclease and/or guide nucleic acid. After editing, the cells are transferred to a separation and filtration module 2130 where the cells are separated and/or concentrated from the editing solution in preparation for transfer to FTEP device 2108.

In FTEP device 2108, the cells are transformed by a second set of editing oligos (or other type of oligos) and the cycle is repeated until the cells have been transformed and edited by a desired number of editing oligonucleotides. As discussed above in relation to FIGS. 19 and 20, the multi-module cell processing system is controlled by a processor 2150 configured to operate the instrument based on user input or is controlled by one or more scripts including at least one script associated with the reagent cartridge. The processor 2150 may control the timing, duration, and temperature of various processes, the dispensing of reagents, and other operations of the various modules of the system 2100. For example, a script or the processor may control the dispensing of cells, reagents, vectors, and editing oligonucleotides; which editing oligonucleotides are used for cell editing and in what order; the time, temperature and other conditions used in the recovery and expression module, the wavelength at which OD is read in the cell growth module, the target OD to which the cells are grown, and the target time at which the cells will reach the target OD. In addition, the processor may be programmed to notify a user (e.g., via an application) as to the progress of the cells in the automated multi-module cell processing system.

Figure 22:
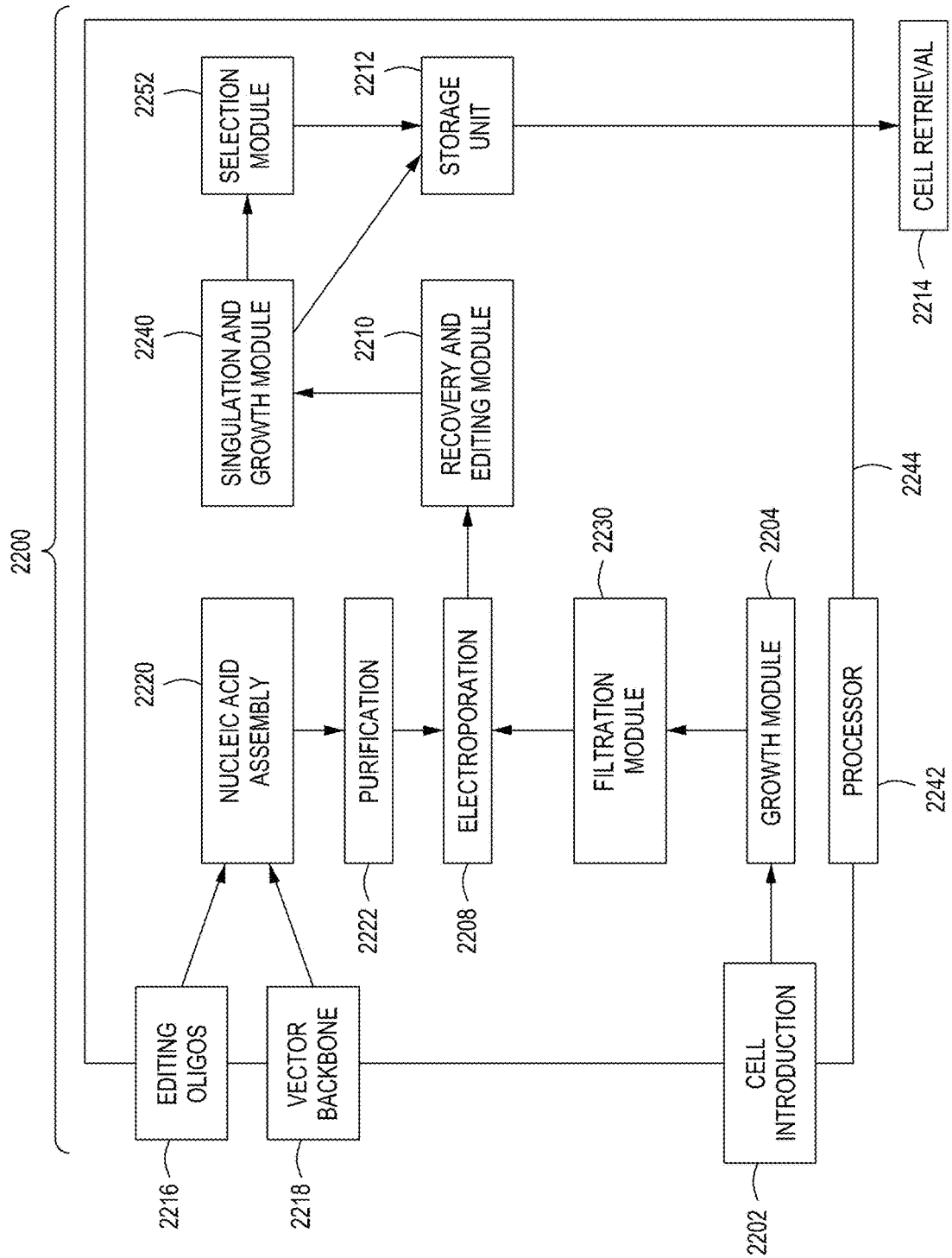
FIG. 22 is a simplified block diagram of an embodiment of an exemplary automated multi-module cell processing system in which one or more of the FTEP devices described herein may be used.

FIG. 22 is a simplified block diagram of an embodiment of an exemplary automated multi-module cell processing system comprising a singulation module for screening for edited cells. The cell processing system 2200 may include a housing 2260, a reservoir of cells to be transformed or transfected 2202, and a growth module (a cell growth device) 2204. The cells to be transformed are transferred from a reservoir to the growth module to be cultured until the cells hit a target OD. Once the cells hit the target OD, the growth module may cool or freeze the cells for later processing, or the cells may be transferred to an optional filtration module 2230 where the cells are rendered electrocompetent and concentrated to a volume optimal for cell transformation. Once concentrated, the cells are then transferred to FTEP device 2208 (transformation/transfection). Exemplary electroporation devices of use in the automated multi-module cell processing systems disclosed herein include those described in U.S. Ser. No. 62/566,374, filed 30 Sep. 2017; U.S. Ser. No. 62/556,375, filed 30 Sep. 2017; U.S. Ser. No. 62/657,651, filed 13 Apr. 2018; and U.S. Ser. No. 62/657,654, filed 13 Apr. 2018, all of which are herein incorporated by reference in their entirety.

In addition to the reservoir for storing the cells, the system 2200 may include a reservoir for storing editing oligonucleotides 2216 and a reservoir for storing an expression vector backbone 2218. Both the editing oligonucleotides and the expression vector backbone are transferred from, e.g., reservoirs in a reagent cartridge to a nucleic acid assembly module 2220, where the editing oligonucleotides are inserted into the expression vector backbone. The assembled nucleic acids may be transferred into an optional purification module 2222 for desalting and/or other purification procedures needed to prepare the assembled nucleic acids for transformation. Alternatively, pre-assembled nucleic acids, e.g., the editing vector, may be stored within reservoir 2216 or 2218. Once the processes carried out by the purification module 2222 are complete, the assembled nucleic acids are transferred to, e.g., FTEP device 2208, which already contains the cell culture grown to a target OD. In FTEP device 2208 the assembled nucleic acids are introduced into the cells. Following electroporation, the cells are transferred into a combined recovery, cell growth, and editing module 2210. In some embodiments the automated multi-module cell processing system 2200 is a system that performs gene editing such as an RNA-direct nuclease editing system. For example, see U.S. Ser. Nos. 16/024,816 and 16/024,831, filed 30 Jun. 2018; U.S. Ser. No. 62/566,688, filed 2 Oct. 2017; and U.S. Ser. No. 62/567,698, filed 3 Oct. 2017, all of which are herein incorporated by reference in their entirety. In the combined recovery, cell growth, and editing module 2210, the cells are allowed to recover post-transformation and editing commences.

Following editing, the cells are transferred to a singulation module 2240, where the cells are arrayed such that there is an average of one cell per compartment. In some embodiments, a compartment may be a well, in some embodiments the compartment may be a droplet, and in some embodiments the compartment may be an area, e.g., cells isolated from one another on an agar plate or arrayed on a functionalized substrate. Once singulated, the cells are allowed to grow and establish colonies which are grown to terminal size or saturation, limited by, e.g., nutrients or physical confinement. Once colonies are established, the colonies are pooled. Singulation overcomes growth bias from unedited cells and growth bias resulting from fitness effects of different edits.

Once the cell colonies are pooled, the cells may be stored, e.g., in a storage module 2212, where the cells can be kept at, e.g., 4° C. until the cells are retrieved for further study. Alternatively, the cells may be used in another round of editing. The multi-module cell processing system is controlled by a processor 2250 configured to operate the instrument based on user input, as directed by one or more scripts, or as a combination of user input or a script. The processor 2250 may control the timing, duration, temperature, and operations of the various modules of the system 2200 and the dispensing of reagents. For example, the processor 2250 may cool the cells post-transformation until editing is desired, upon which time the temperature may be raised to a temperature conducive of genome editing and cell growth. The processor may be programmed with standard protocol parameters from which a user may select, a user may specify one or more parameters manually or one or more scripts associated with the reagent cartridge may specify one or more operations and/or reaction parameters. In addition, the processor may notify the user (e.g., via an application to a smart phone or other device) that the cells have reached the target OD as well as update the user as to the progress of the cells in the various modules in the multi-module system.

The automated multi-module cell processing system 2200 is a nuclease-directed genome editing system and can be used in single editing systems. The system of FIG. 23, described below, is configured to perform sequential editing, e.g., using different nuclease-directed systems sequentially to provide two or more genome edits in a cell; and/or recursive editing, e.g. utilizing a single nuclease-directed system to introduce two or more genome edits in a cell.

Figure 23:
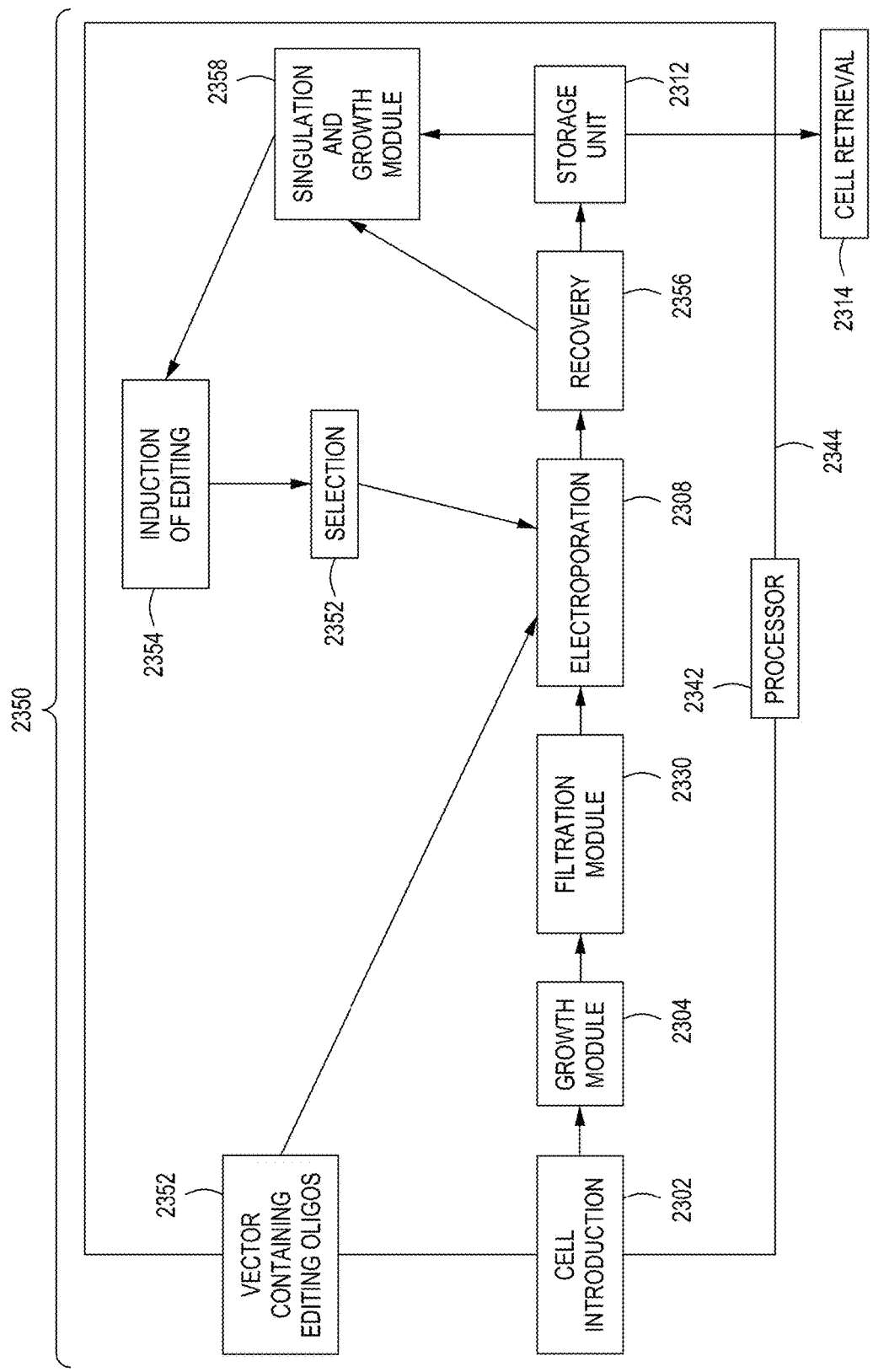
FIG. 23 is a simplified block diagram of an embodiment of an exemplary automated multi-module cell processing system in which one or more of the FTEP devices described herein may be used.

FIG. 23 illustrates another embodiment of a multi-module cell processing system. This embodiment depicts an exemplary system that 1) includes editing induction and cell selection in addition to screening, and 2) performs recursive gene editing on a cell population. As with the embodiment shown in FIG. 22, the cell processing system 2300 may include a housing 2360, a reservoir for storing cells to be transformed or transfected 2302, and a cell growth module (a cell growth device) 2304. The cells to be transformed are transferred from a reservoir to the cell growth module to be cultured until the cells hit a target OD. Once the cells hit the target OD, the growth module may cool or freeze the cells for later processing or transfer the cells to an optional filtration module 2330 where the cells are rendered electrocompetent, and the volume of the cells may be reduced substantially. Once the cells have been concentrated to an appropriate volume, the cells are transferred to FTEP device 2308. In addition to the reservoir for storing cells, the multi-module cell processing system includes a reservoir for storing the vector comprising editing oligonucleotides 2352. The assembled nucleic acids are transferred to FTEP device 2308, which already contains the cell culture grown to a target OD. In the FTEP device 2308, the nucleic acids are electroporated into the cells. Following electroporation, the cells are transferred into an optional recovery module 2342, where the cells are allowed to recover briefly post-transformation.

After recovery, the cells may be transferred to a storage module 2312, where the cells can be stored at, e.g., 4° C. until the cells are retrieved for further study, or the cells may be transferred to a singulation and growth module 2344. In the singulation module 2344, the cells are arrayed such that there is an average of one cell per compartment. In some embodiments, a compartment may be a well; a droplet; or an area, e.g., cells isolated from one another on an agar plate or arrayed on, e.g., a functionalized substrate. Once singulated, the cells are allowed to grow through several to many doublings and establish colonies. Once colonies are established, the substrate with the cell colonies is transferred to an induction module 2346, where conditions exist (temperature, addition of an inducing or repressing chemical) to induce editing. Once editing is initiated and allowed to proceed, the substrate is transferred to a selection module 2348, which may include, e.g., a colony measuring and picking device that selects small colonies of cells; a spectrophotometer configured to measure OD in wells or droplets and collect colonies of edited cells based on cell growth; or a spectrophotometer configured to measure other cellular characteristics in wells or droplets and collect colonies of edited cells based on cell characteristics that correlate with cell growth. Note that the singulation module and selection module may be linked. Once the putatively-edited cells are selected, they may be subjected to another round of editing, beginning with transformation by yet another donor nucleic acid in another editing cassette via the FTEP module 2308.

In FTEP device 2308, the cells selected from the first round of editing are transformed by a second set of editing oligos (or other type of oligos) and the cycle is repeated until the cells have been transformed and edited by a desired number of, e.g., donor nucleic acids. The multi-module cell processing system exemplified in FIG. 23 is controlled by a processor 2350 configured to operate the instrument based on user input, or is controlled by one or more scripts including at least one script associated with the reagent cartridge. The processor 2350 may control the timing, duration, and temperature of various processes, the dispensing of reagents, and other operations of the various modules of the system 2300. For example, a script or the processor may control the dispensing of cells, reagents, vectors, and editing oligonucleotides; which editing oligonucleotides are used for cell editing and in what order; the time, temperature and other conditions used in the recovery and expression module, the wavelength at which OD is read in the cell growth module, the target OD to which the cells are grown, and the target time at which the cells will reach the target OD. In addition, the processor may be programmed to notify a user (e.g., via an application) as to the progress of the cells in the automated multi-module cell processing system.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example 1: Production and Transformation of Electrocompetent E. coli

For testing transformation of the FTEP device, electrocompetent E. coli cells were created. To create a starter culture, 6 ml volumes of LB chlor-25 (LB with 25 μg/ml chloramphenicol) were transferred to 14 ml culture tubes. A 25 μl aliquot of E. coli was used to inoculate the LB chlor-25 tubes. Following inoculation, the tubes were placed at a 45° angle in the shaking incubator set to 250 RPM and 30° C. for overnight growth, between 12-16 hrs. The OD600 value should be between 2.0 and 4.0. A 1:100 inoculum volume of the 250 ml LB chlor-25 tubes were transferred to four sterile 500 ml baffled shake flasks, i.e., 2.5 ml per 250 ml volume shake flask. The flasks were placed in a shaking incubator set to 250 RPM and 30° C. The growth was monitored by measuring OD600 every 1 to 2 hr. When the OD600 of the culture was between 0.5-0.6 (approx. 3-4 hrs), the flasks were removed from the incubator. The cells were centrifuged at 4300 RPM, 10 min, 4° C. The supernatant was removed, and 100 ml of ice-cold 10% glycerol was transferred to each sample. The cells were gently resuspended, and the wash procedure performed three times, each time with the cells resuspended in 10% glycerol. After the fourth centrifugation, the cell resuspension was transferred to a 50 ml conical Falcon tube and additional ice-cold 10% glycerol added to bring the volume up to 30 ml. The cells were again centrifuged at 4300 RPM, 10 min, 4° C., the supernatant removed, and the cell pellet resuspended in 10 ml ice-cold glycerol. The cells are aliquoted in 1:100 dilutions of cell suspension and ice-cold glycerol.

Figure 24:
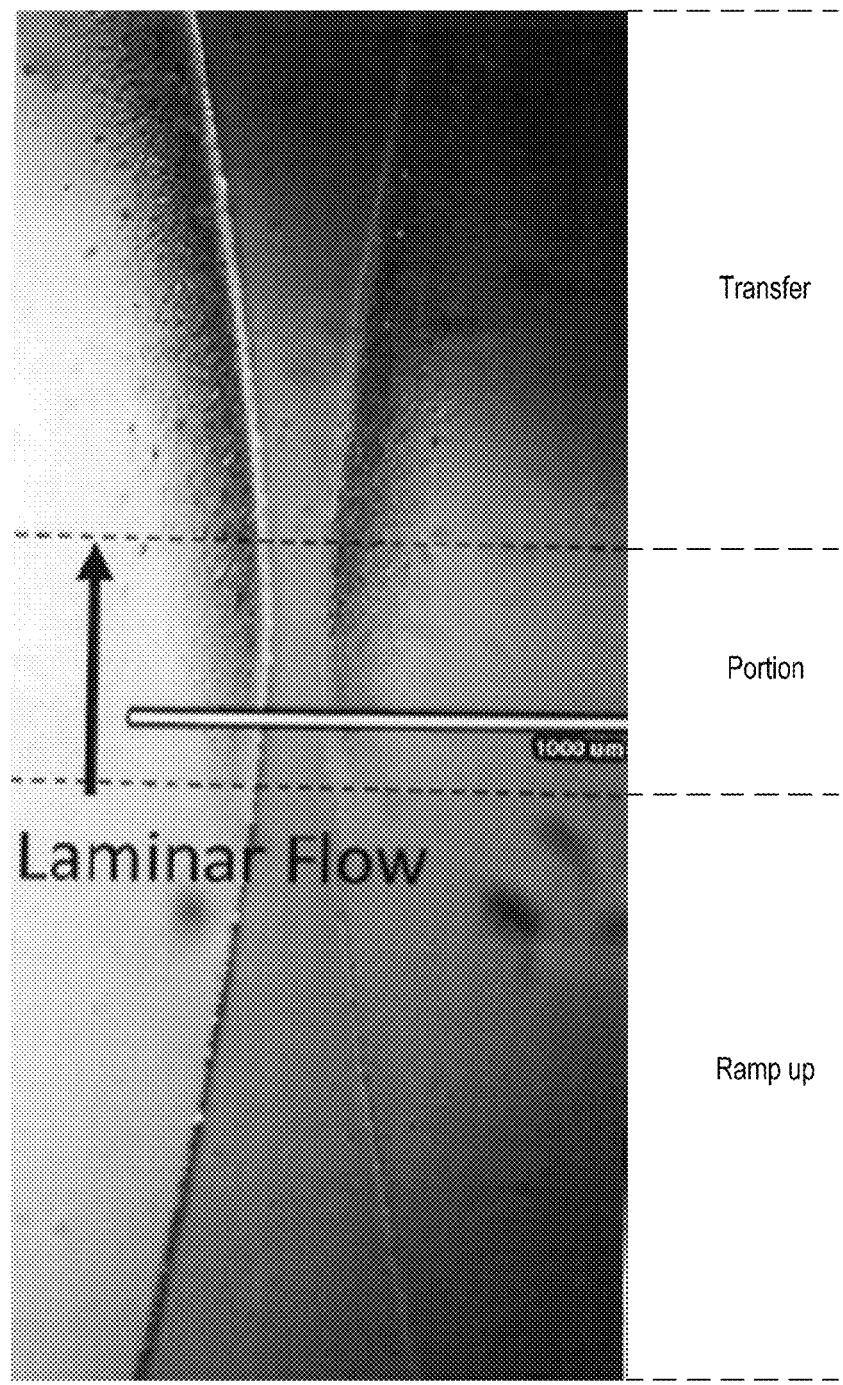
FIG. 24 is a photograph demonstrating laminar flow of cells and exogenous material in buffer through a flow channel of an FTEP device of the disclosure.

The comparative electroporation experiment was performed to determine the efficiency of transformation of the electrocompetent E. coli using the embodiment of the FTEP device shown at (ii), (iii), and (vi) of FIGS. 15B and 15C and (ii) and (vi) of FIG. 15D. (See FIG. 24 for a scanning electromicrograph demonstrating laminar flow of cells and exogenous material through the narrowed portion of the flow channel of an FTEP device). The flow rate was controlled with a pressure control system. The suspension of cells with DNA was loaded into the FTEP inlet reservoir. The transformed cells flowed directly from the inlet and inlet channel, through the flow channel, through the outlet channel, and into the outlet containing recovery medium. The cells were transferred into a tube containing additional recovery medium, placed in an incubator shaker at 30° C. shaking at 250 rpm for 3 hours. The cells were plated to determine the colony forming units (CFUs) that survived electroporation and failed to take up a plasmid and the CFUs that survived electroporation and took up a plasmid. Plates were incubated at 30° C.; E. coli colonies were counted after 24 hrs.

Figure 25A:
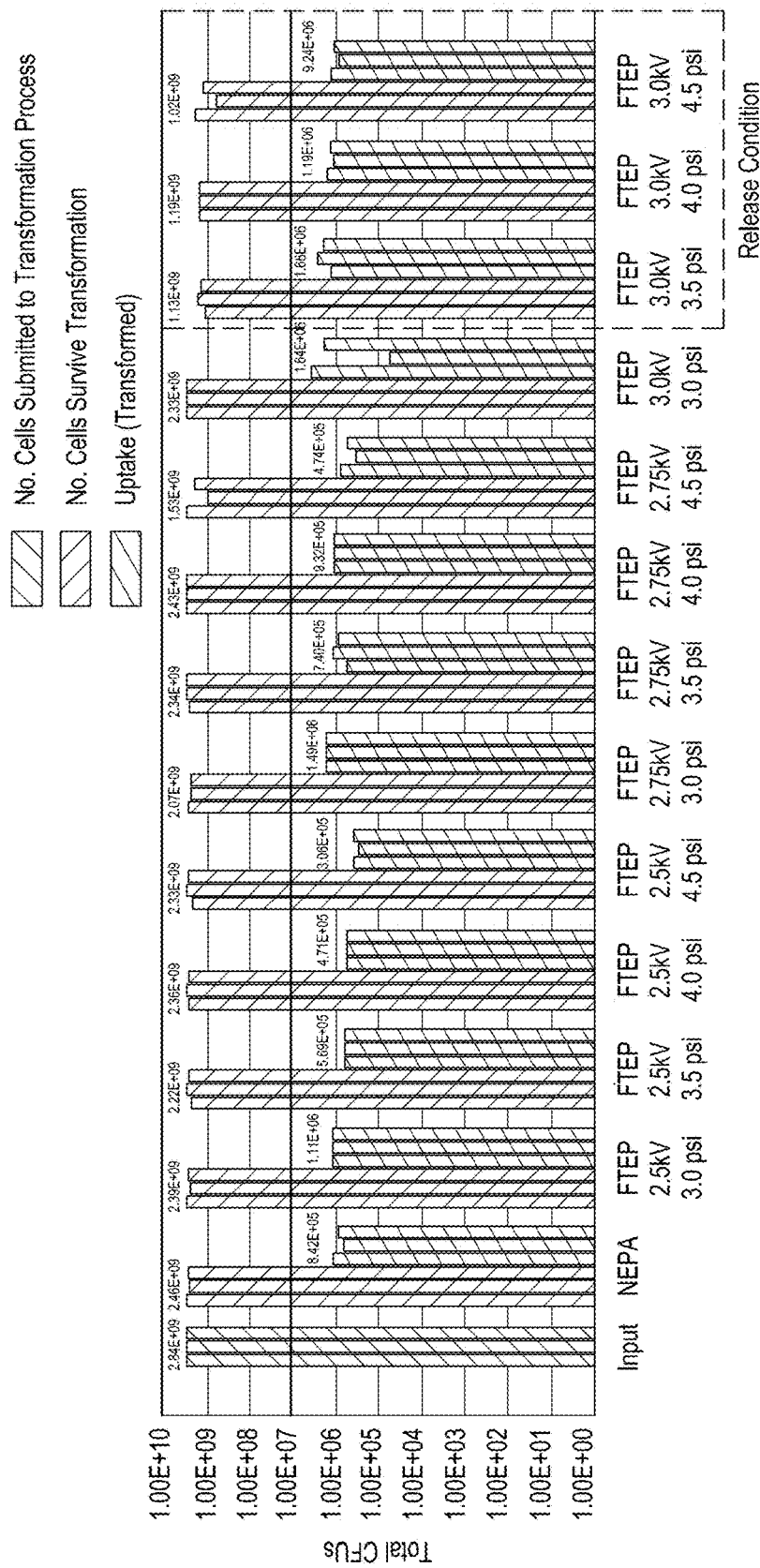
FIG. 25A is a bar graph showing the results of electroporation of *E. coli* using a device of the disclosure and a comparator electroporation device.

The flow-through electroporation experiments were benchmarked against 2 mm electroporation cuvettes (Bull dog Bio) using an in vitro high voltage electroporator (NEPAGENE™ ELEPO21). Stock tubes of cell suspensions with DNA were prepared and used for side-to-side experiments with the NEPAGENE™ and the flow-through electroporation. The results are shown in FIG. 25A. In FIG. 25A, the left-most bars hatched /// denote cell input, the bars to the left bars hatched \\\ denote the number of cells that survived transformation, and the right bars hatched /// denote the number of cells that were actually transformed. The FTEP device showed equivalent transformation of electrocompetent E. coli cells at various voltages as compared to the NEPAGENE™ electroporator. As can be seen, the transformation survival rate is at least 90% and in some embodiments is at least 95%, 96%, 97%, 98%, or 99%. The recovery ratio (the fraction of introduced cells which are successfully transformed and recovered) is in certain embodiments at least 0.001 and preferably between 0.00001 and 0.01. In FIG. 25A the recovery ratio is approximately 0.0001.

Figure 25B:
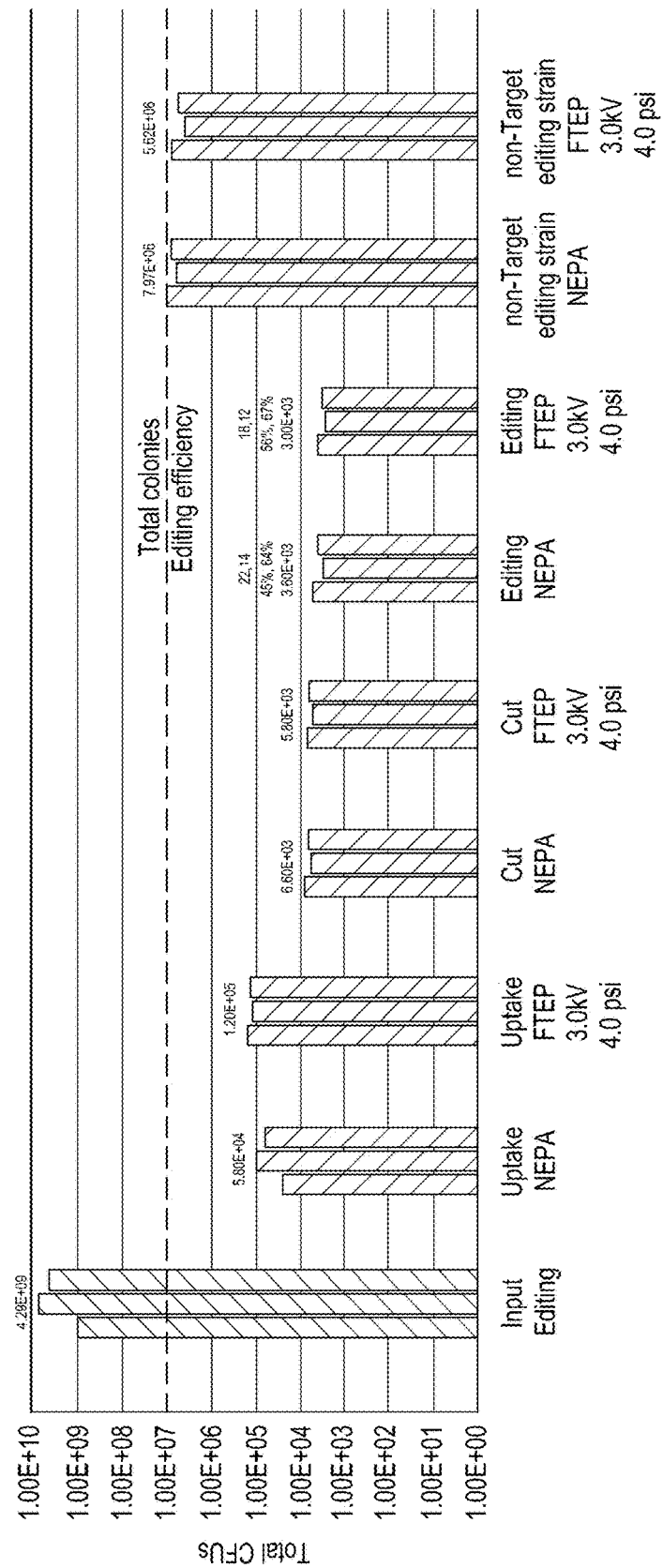
FIG. 25B is a bar graph showing uptake, cutting, and editing efficiencies of *E. coli* cells transformed via an FTEP as described herein benchmarked against a comparator electroporation device.

Additionally, a comparison of the NEPAGENE™ ELEPO21 and the FTEP device was made for efficiencies of transformation (uptake), cutting, and editing. In FIG. 25B, triplicate experiments were performed where the bars hatched /// denote the number of cells input for transformation, and the bars hatched \\\ denote the number of cells that were transformed (uptake), the number of cells where the genome of the cells was cut by a nuclease transcribed and translated from a vector transformed into the cells (cutting), and the number of cells where editing was effected (cutting and repair using a nuclease transcribed and translated from a vector transformed into the cells, and using a guide RNA and a donor DNA sequence both of which were transcribed from a vector transformed into the cells). Again, it can be seen that the FTEP showed equivalent transformation, cutting, and editing efficiencies as the NEPAGENE™ electroporator. The recovery rate in FIG. 25B for the FTEP is treater than 0.001.

Example 2: Production and Transformation of Electrocompetent S. Cerevisiae

For further testing transformation of the FTEP device, S. Cerevisiae cells were created using the methods as generally set forth in Bergkessel and Guthrie, Methods Enzymol., 529:311-20 (2013). Briefly, YFAP media was inoculated for overnight growth, with 3 ml inoculate to produce 100 ml of cells. Every 100 ml of culture processed resulted in approximately 1 ml of competent cells. Cells were incubated at 30° C. in a shaking incubator until they reached an OD600 of 1.5+/−0.1.

A conditioning buffer was prepared using 100 mM lithium acetate, 10 mM dithiothreitol, and 50 mL of buffer for every 100 mL of cells grown and kept at room temperature. Cells were harvested in 250 ml bottles at 4300 rpm for 3 minutes, and the supernatant removed. The cell pellets were suspended in 100 ml of cold 1 M sorbitol, spun at 4300 rpm for 3 minutes and the supernatant once again removed. The cells were suspended in conditioning buffer, then the suspension transferred into an appropriate flask and shaken at 200 RPM and 30° C. for 30 minutes. The suspensions were transferred to 50 ml conical vials and spun at 4300 rpm for 3 minutes. The supernatant was removed and the pellet resuspended in cold 1 M sorbitol. These steps were repeated three times for a total of three wash-spin-decant steps. The pellet was suspended in sorbitol to a final OD of 150+/−20.

A comparative electroporation experiment was performed to determine the efficiency of transformation of the electrocompetent S. Cerevisiae using the FTEP device. The flow rate was controlled with a syringe pump (Harvard apparatus PHD ULTRA™ 4400). The suspension of cells with DNA was loaded into a 1 mL glass syringe (Hamilton 81320 Syringe, PTFE Luer Lock) before mounting on the pump. The output from the function generator was turned on immediately after starting the flow. The processed cells flowed directly into a tube with 1M sorbitol with carbenicillin. Cells were collected until the same volume electroporated in the NEPAGENE™ had been processed, at which point the flow and the output from the function generator were stopped. After a 3-hour recovery in an incubator shaker at 30° C. and 250 rpm, cells were plated to determine the colony forming units (CFUs) that survived electroporation and failed to take up a plasmid and the CFUs that survived electroporation and took up a plasmid. Plates were incubated at 30° C. Yeast colonies are counted after 48-76 hrs.

Figure 26:
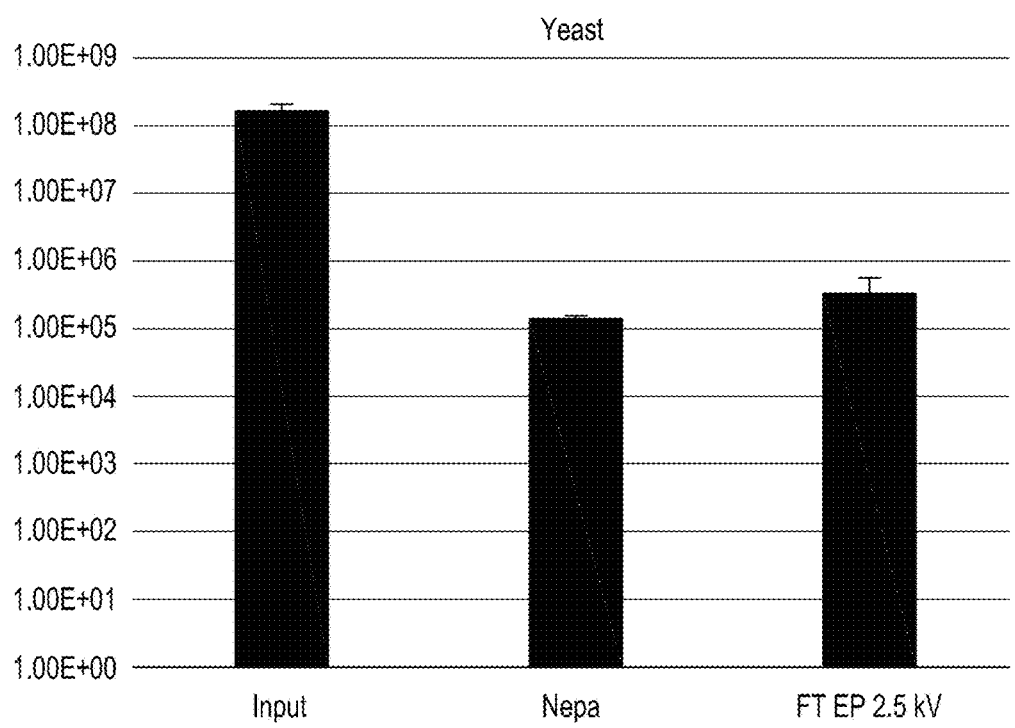
FIG. 26 is a bar graph showing the results of electroporation of *S. cerevisiae* using an FTEP device of the disclosure and a comparator electroporation method.

The flow-through electroporation experiments were benchmarked against 2 mm electroporation cuvettes (Bull dog Bio) using an in vitro high voltage electroporator (NEPAGENE™ ELEPO21). Stock tubes of cell suspensions with DNA were prepared and used for side-to-side experiments with the NEPAGENE™ and the flow-through electroporation. The results are shown in FIG. 26. The device showed better transformation and survival of electrocompetent S. Cerevisiae at 2.5 kV voltages as compared to the NEPAGENE™ method. Input is total number of cells that were processed.

Example 3: FTEP Pressure Sensing and Flow Rates

An inline flow sensor measurement was used to indicate when, after the liquid containing the cells and DNA flowed through the FTEP chip, where the inlet reservoir was emptied. Approximately 65 μL of liquid was loaded into the input reservoir and the automated FTEP module was powered on. Looking at the graph at the top of FIG. 27, it can be seen that after a few short startup transients, the flow rate shows about ~3 standard cubic centimeters per minute (SCCM) of flow for almost 8 seconds (8000 ms) until it jumps to 24 SCCM. This transition occurs at an end of run trigger, which is an indicator that the liquid containing the cells and DNA has been processed through the FTEP device and that air is not flowing through the FTEP device. That trigger may constitute detection of an increase flow rate or a sudden fluctuation (increase or decrease) in the pressure of the air (such as at a conduit leading from a syringe pump). In one preferred embodiment, the flow sensor in FIG. 27 detects an increase in air flow indicative of the fluid being completely drained from the input reservoir. At this point, pressure may be reversed to allow a multi-pass electroporation procedure; that is, cells to electroporated may be "pulled" from the inlet toward the outlet for one pass of electroporation, and once the inlet reservoir is emptied, the sensor may reverse the pressure where the liquid and cells/DNA is "pushed" from the outlet end of the flow-through FTEP device toward the inlet end to pass between the electrodes again for another pass of electroporation. This process may be repeated one to many times. Alternatively, the pressure may be stopped entirely and the transformed cells in the outlet retrieved.

Figure 27:
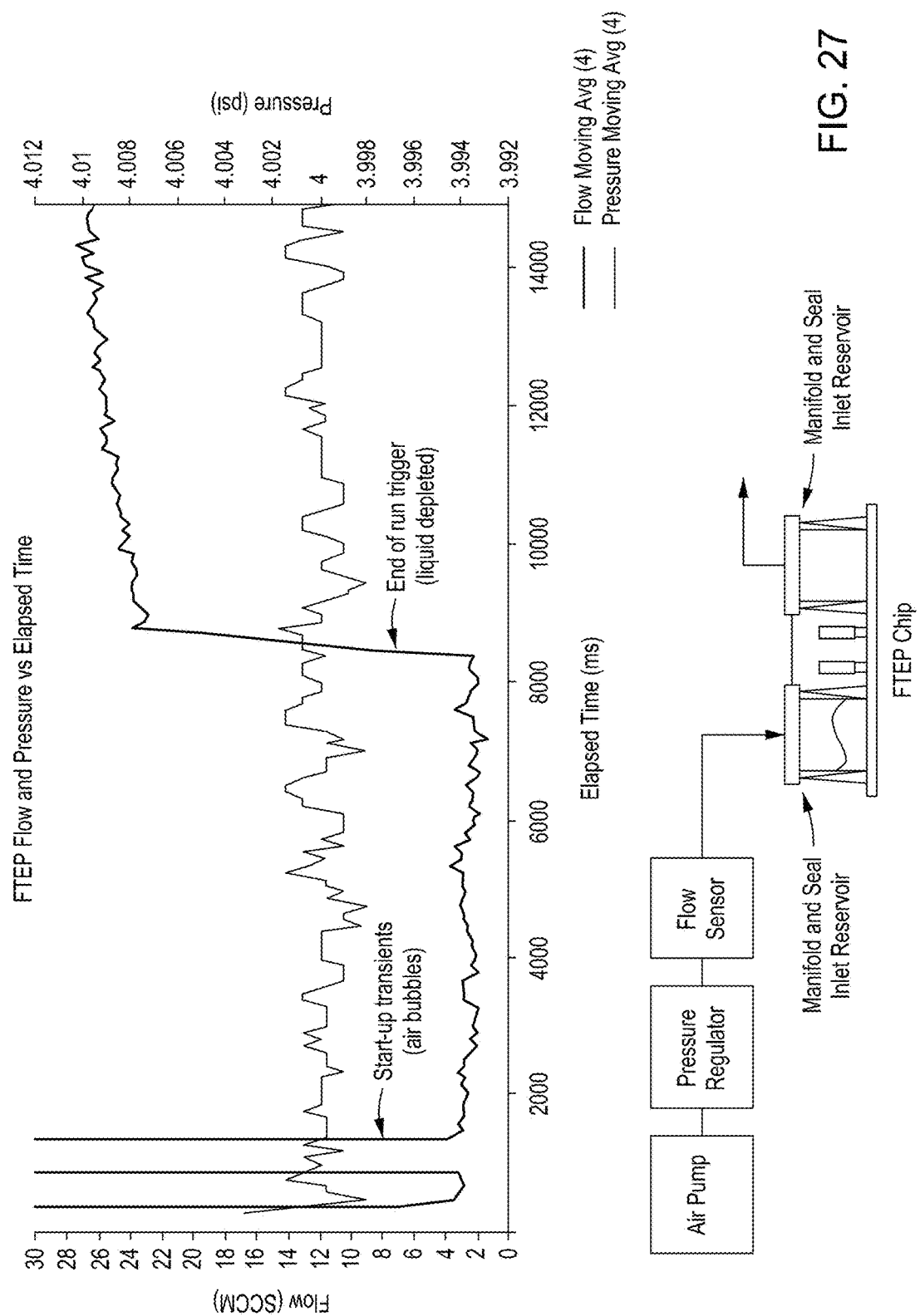
FIG. 27 shows a graph of FTEP flow and pressure versus elapsed time (top), as well as a simple depiction of the pressure system and FTEP (bottom).

The multi-cycle approach may be particularly advantageous in that it limits the dwell time of the cells and exogenous materials in the electric filed which may in turn prevent cell damage and increase survival rates. The back-and-forth process may be repeated 1, 2, 3, 4, 5, 6, 7, 8, 9, or 10 times. FIG. 27 at bottom shows a simple depiction of the pressure system and FTEP. The pressure manifold is mated to the upwardly-extending reservoirs via one or more complementary seals or gaskets disposed on the manifold or the reservoirs. The manifolds may take the form of the "lids" 1608 shown in FIG. 16B (v).

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

We claim:

1. A flow-through electroporation (FTEP) device for introducing an exogenous material into cells in a fluid, wherein the FTEP device has a top surface and a bottom surface, the FTEP device comprising:
   a. an inlet reservoir, an inlet, and a first inlet channel for receiving a fluid comprising cells and exogenous material into the FTEP device, wherein the inlet reservoir originates from the top surface of the FTEP device;
   b. an outlet reservoir, an outlet, and an outlet channel for removing a fluid comprising transformed cells and exogenous material from the FTEP device, wherein the outlet reservoir originates from the top surface of the FTEP device;
   c. a flow channel intersecting and positioned between the first inlet channel and the outlet channel, wherein the flow channel decreases in width to a dimension no smaller than at least 2× diameter of the cells being electroporated to form a constriction of the flow channel between the first inlet channel and the outlet channel;
   d. a first electrode and a second electrode each positioned in an electrode channel, wherein the electrode channels originate from the top surface of the FTEP device, wherein the first electrode is positioned between the first inlet channel and the constriction and wherein the second electrode is positioned between the constriction and the outlet channel; wherein the electrodes are in fluid and electrical communication with fluid in the flow channel but not directly in the path of the cells traveling through the flow channel; and wherein the electrodes apply one or more electric pulses to the cells in the fluid as they pass through the flow channel, thereby introducing exogenous material into the cells in the fluid; and
   e. a pressure source, a flow sensor measurement device and a processor, wherein the processor is programmed such that, the pressure source pushes flow of the cells and exogenous material between the inlet reservoir and the outlet reservoir, the flow sensor measurement device senses flow of the cells and exogenous material and, when the flow sensor measurement device detects an increase in air flow indicative of fluid being completely drained from the inlet reservoir, the flow sensor measurement device communicates with the processor to communicate with the pressure source to pull flow of the cells and exogenous material between the outlet reservoir and the inlet reservoir, thereby reversing the flow of the cells and exogenous material.

2. The FTEP device of claim 1, wherein the FTEP device comprises a second inlet and a second inlet channel and further comprises a reservoir connected to the second inlet for introducing exogenous material into the FTEP device.

3. The FTEP device of claim 2, wherein the second inlet and second inlet channel are located between the first inlet and first inlet channel and the first electrode.

4. The FTEP device of claim 2, wherein the second inlet and second inlet channel are located between the second electrode and the outlet channel.

5. The FTEP device of claim 1, wherein device is configured for use with bacterial, yeast and mammalian cells.

6. The FTEP device of claim 1, wherein the two electrodes are located from 1 mm to 10 mm from one another.

7. The FTEP device of claim 1, wherein the narrowest part of the channel width is from 10 μM to 5 mm.

8. The FTEP device of claim 1, wherein the device further comprises one or more filters between the first inlet channel and the outlet channel.

9. An automated multi-module cell processing system, comprising the FTEP device of claim 1.

* * * * *